United States Patent
Han et al.

(10) Patent No.: US 10,179,177 B2
(45) Date of Patent: Jan. 15, 2019

(54) COATED UP-CONVERSION NANOPARTICLES

(71) Applicant: University of Massachusetts Medical School, Boston, MA (US)

(72) Inventors: Gang Han, Shrewsbury, MA (US); Jie Shen, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/045,600

(22) Filed: Feb. 17, 2016

(65) Prior Publication Data

US 2016/0228578 A1    Aug. 11, 2016

Related U.S. Application Data

(63) Continuation of application No. 13/902,298, filed on May 24, 2013, now Pat. No. 9,333,271.

(60) Provisional application No. 61/653,406, filed on May 30, 2012, provisional application No. 61/675,019, filed on Jul. 24, 2012.

(51) Int. Cl.
| | |
|---|---|
| *A61K 49/00* | (2006.01) |
| *C09K 11/00* | (2006.01) |
| *A61K 41/00* | (2006.01) |
| *C01F 17/00* | (2006.01) |
| *C09K 11/02* | (2006.01) |
| *C09K 11/77* | (2006.01) |
| *B82Y 5/00* | (2011.01) |

(52) U.S. Cl.
CPC ........ *A61K 49/0019* (2013.01); *A61K 41/008* (2013.01); *A61K 49/0052* (2013.01); *A61K 49/0065* (2013.01); *A61K 49/0067* (2013.01); *A61K 49/0093* (2013.01); *C01F 17/0031* (2013.01); *C09K 11/025* (2013.01); *C09K 11/7773* (2013.01); *B82Y 5/00* (2013.01); *C01P 2002/72* (2013.01); *C01P 2002/84* (2013.01); *C01P 2004/02* (2013.01); *C01P 2004/04* (2013.01); *C01P 2004/64* (2013.01)

(58) Field of Classification Search
CPC ............................... A61K 49/00; C09K 11/00
See application file for complete search history.

(56) References Cited

PUBLICATIONS

Marcin Nyk et al., High Contrast in Vitro and in Vivo Photoluminescence Bioimaging Using Near Infrared to NEar Infrared Up-Conversion in Tm3+ and Yb3+ Doped Fluoride Nanophosphors, Nano Letters, 2008, vol. 8, 3834-3838.*
Liqin Xiong et al., Long-term in vivo biodistribution imaging and toxicity of polyacrylic acid-coated upconversion nanophosphors, Biomaterials, 2010, 31, 7078-7-85.*
Angang Dong et al., A Generalized Ligan-Exchange Strategy Enabling Sequential Surface Functionalization of Colloidal Nanocrystals, J. Am. Chem. Soc, 2011, 133, 998-1006.*
Zewei Quan et al., Uniform Colloidal Alkaline Eart Metal Fluoride Nanocrystals: Nonhydrolytic Synthesis and Luminescence Properties, Inorg. Chem, 2008, 47, 9509-9517.*
John-Christopher Boyer. Synthesis of Colloidal Upconverting NaYF4, Nanocrystals Doped with Er3+, Yb3+, and Tm3+, Yb3+ via Thermal Decompositin of Lanthanide Trifluoroacetate Precursors, J. Am. Chem. Soc., 128, 7444-7445 (Year: 2006).*
Guang-Shun Yi et al., Water-soluble NaYF4:Yb,Er (Tm)/NaYF4/Polymer Core/Shell/Shell Nanoparticles with Signicficant Enhancement of Upconversion Fluorescence, Chem. Mater, 19, 341-343 (Year: 2007).*
Guang-Shun Yi et al. Supporting Information (Year: 2007).*
Zewei Quan et al., Uniform Colloidal Alkaline Eart Metal Fluoride Nanocrystals: Nonhydrolytic Synthesis and Luminescence Properties, Inorg. Chem, 47, 9509-9517. (Year: 2008).*

\* cited by examiner

*Primary Examiner* — Michael G. Hartley
*Assistant Examiner* — Jagadishwar R Samala
(74) *Attorney, Agent, or Firm* — Milstein Zhang & Wu LLC

(57) ABSTRACT

The invention provides novel biocompatible upconversion nanoparticle (UCNP) that comprises a core of cubic nanocrystals (e.g., comprising α-Na $Ln_a$ $Ln_b$ $Ln_c$ $F_4$) and an epitaxial shell (e.g., formed from $CaF_2$; wherein $Ln_b$ is Yb), and related methods of preparation and uses thereof.

9 Claims, 38 Drawing Sheets

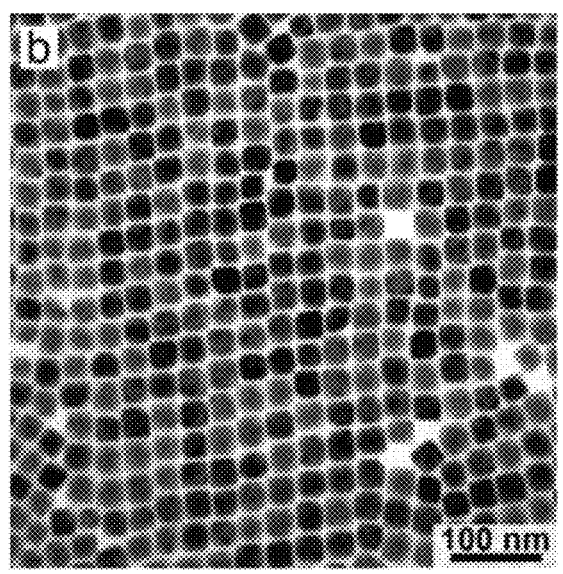
FIG. 2(b)
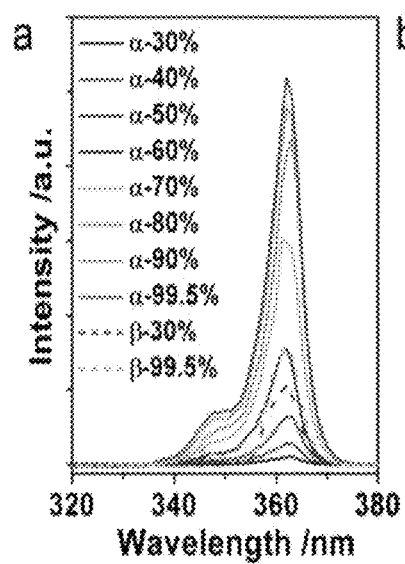
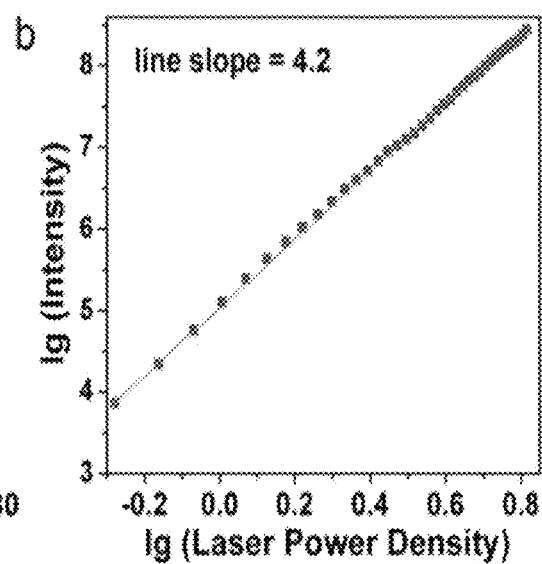
FIG. 3(a)                    FIG. 3(b)

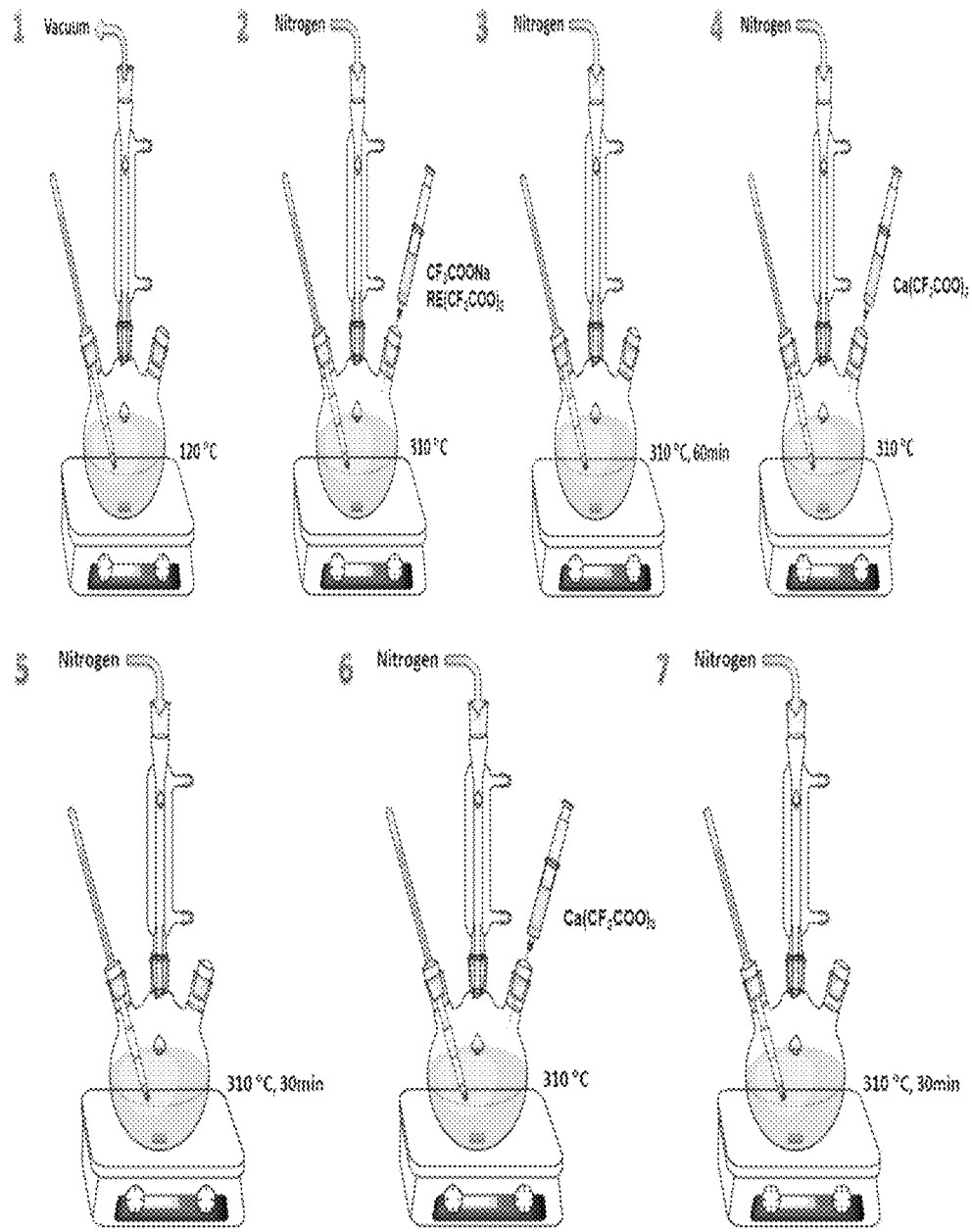
FIG. 18 (Con'd)

COATED UP-CONVERSION NANOPARTICLES

PRIORITY CLAIMS AND RELATED PATENT APPLICATIONS

This application is a continuation application of and claims priority to U.S. patent application Ser. No. 13/902,298, filed May 24, 2013, which claims the benefit of priority from U.S. Provisional Application Ser. No. 61/653,406, filed on May 30, 2012, and from U.S. Provisional Application Ser. No. 61/675,019, filed on Jul. 24, 2012, the entire content of each of which is incorporated herein by reference in its entirety for all purposes.

TECHNICAL FIELD OF THE INVENTION

The present invention generally relates to upconversion luminescence nano-structured material(s) and methods for preparation and uses thereof. More particularly, the invention relates to a novel biocompatible upconversion nanoparticle (UCNP) comprising a core of cubic nanocrystals (e.g., comprising α-Na $Ln_a$ $Ln_b$ $Ln_c$ $F_4$) and an epitaxial shell (e.g., formed from $CaF_2$; wherein $Ln_b$ is Yb).

BACKGROUND OF THE INVENTION

Upconversion nanoparticles (UCNPs) have recently emerged as a new class of materials with potential applications in a wide-range of fields, such as biosensing, chemical sensing, in vivo imaging, drug delivery, photodynamic therapy and photoactivation. (Zhan, et al. 2011 *Acs Nano* 5, 3744; Wang, et al. 2005 *Angew Chem Int Edit* 44, 6054; Achatz, et al. 2011 *Angew Chem Int Edit* 50, 260; Liu, et al. 2011 *Acs Nano* 5, 8040; Liu, et al. 2011 *J Am Chem Soc* 133, 17122; Chen, et al. 2012 *Acs Nano* 6, 8280; Lim, et al. 2006 *Nano Lett* 6, 169; Wang, et al. 2011 *Biomaterials* 32, 1110; Hou, et al. 2011 *Adv Funct Mater* 21, 2356; Tian, et al. 2012 *Adv Mater* 24, 1226; Shan, et al. 2011 *Adv Funct Mater* 21, 2488; Zhang, et al. 2007 *J Am Chem Soc* 129, 4526; Jayakumar, et al. 2012 *Natl Acad Sci USA* 109, 8483; Yang, et al. 2012 *Angew Chem Int Edit* 51, 3125; Yan, et al. 2012 *J Am Chem Soc* 134, 16558; U.S. Pat. No. 7,332,344; U.S. Pat. No. 7,790,392; U.S. Pat. No. 7,501,092; U.S. Pat. No. 8,088,631.)

Upconverting luminescence refers to an anti-Stokes type process in which the sequential absorption of two or more photons leads to the emission of light at shorter wavelength (e.g., ultraviolet, visible, and near-infrared) than the excitation wavelength. For instance, Lanthanide ion ($Ln^{3+}$) doped UCNPs are able to absorb near-infrared (NIR) photons and convert such low energy into shorter wavelength emissions. (Haase, et al. 2011 *Angew Chem Int Edit* 50, 5808.) Utilizing long-lived, ladder-like energy levels of $Ln^{3+}$, the intensity of anti-Stokes luminescence of UCNPs is orders of magnitude more potent compared with those of conventional synthetic dyes or quantum dots (QDs). (Wang, et al. 2009 *Chem Soc Rev* 38, 976-989.)

In the past decade, $NaYF_4$ based upconversion nanoparticles have been widely studied as optical bio-probes based on their advantages like low photo-degradation, non-photo-bleaching, deep tissue penetration and weak auto-fluorescence. (Chatterjee, et al. 2010 *Small* 6, 2781-2795.)

NIR emitting UCNPs have several additional advantages over more traditional fluorescent probes. For example, UCNPs are excited with a biocompatible NIR wavelength (980 nm), which is then upconverted to a higher energy for emission at a shorter NIR wavelength (800 nm). This $NIR_{in}$-$NIR_{out}$ property permits less light scattering and greater tissue penetration for in vivo imaging because both excitation and emission wavelength are within the biological NIR optical transmission window (700-1000 nm). Moreover, the longer wavelength NIR light minimizes photo-induced damage. In addition, the spectral overlap with endogenous cellular fluorophores is significantly minimized, providing virtually zero auto-fluorescent background, which significantly enhances the signal-to-noise ratio. The nanoparticles are extremely photostable, making them ideal for longitude tracking experiments. UCNPs do not contain toxic elements of Class A (cadmium [Cd], mercury [Hg], lead [Pb]) and Class B (selenium [Se], arsenic [As]), offering great potential as biocompatible imaging probes for clinical applications. Finally, UCNPs can be made into dual optical/MRI probes by doping the same nanoparticle matrix containing lanthanide with the conventional MRI contrast element, gadolinium (Gd), thus synergizing the advantages of light- and magnetic resonance-imaging modalities.

Most photosensitizers are excited by visible or UV light, which has limited penetration depth due to the light absorption and scattering by biological tissues, resulting in ineffective diagnostic and therapeutic effects to internal or large tumors. UCNPs have the ability to convert NIR light to UV and visible photons, which can active photosensitizers adsorbed on nanoparticles via resonance energy transfer to generate reactive oxygen species (ROS) to kill cancer cells. It would provide a promising alternative to overcome hurdles of current photodynamic therapies.

However, UCNPs are hindered by the potential toxicity of the lanthanides. Moreover, most current protocols for synthesizing such UCNPs are not reliable and are not amenable to large-scale productions due to their inconvenient precursor pretreatments, multi-step phase-transitions, and/or long aging processes.

Wang et al. reported that a $CaF_2$ shell can improve the upconversion luminescence of α-$NaLnF_4$ UCNPs using a two-step reaction. (Wang, et al. 2012 *Chem. Eur. J.* 18, 5558-5564.) Yet, the byproduct of a water molecule from their high temperature reaction with the mixture of oleic acid and oleyl amine solvents lead to intense explosive boiling, and limiting the reproducibility of the synthesis and uniformity of the nanoparticle products. In addition, such a complicated two-step approach also hinders the further development of UCNPs in a high throughput manner.

Accordingly, there is an ongoing need for novel UCNPs and improved methods of syntheses and applications thereof, especially those that require biocompatibility.

SUMMARY OF THE INVENTION

The invention is based in part on the discovery of novel biocompatible UCNPs, methods of syntheses and applications thereof. The UCNP of the invention includes a core of cubic nanocrystals comprising α-Na $Ln_a$ $Ln_b$ $Ln_c$ $F_4$; and an epitaxial shell formed from $CaF_2$, wherein $Ln_b$ is Yb.

In certain embodiments, the invention provides a biocompatible UCNP that includes: a core of cubic nanocrystals comprising α-Na (Y, Yb, Tm)$F_4$; an epitaxial shell formed from $CaF_2$; and an outer layer of an organic acid that covers the epitaxial shell, wherein the molar ratio of Tm/(Y+Yb+Tm) is a about 0.5±0.02%; and the molar ratio of Yb/(Y+Yb+Tm) is greater than about 30%.

The invention also provides a method for synthesizing UCNPs in a single reactor vessel. The method includes: heating a solvent mixture comprising an organic acid and an organic alkene in the reaction vessel to an elevated temperature; injecting a core precursor solution comprising a mixture of rare earths into the reaction vessel; injecting a shell precursor solution into the reaction vessel; and collecting the UCNPs.

The invention also provides a method of whole body imaging of an animal. The method includes: injecting the animal with the UCNPs; exciting the UCNP with a laser having a wavelength from about 900 nm to about 1064 nm; and recording the emission luminescence at a wavelength of from about 600 nm to about 1000 nm.

The invention also provides a photochemical method comprising: administering to a cell an UCNP coated with a light sensitive molecule; exciting the UCNP with a laser having a wavelength from about 900 nm to about 1064 nm; causing the UCNP to emit a luminescence at a wavelength of from about 340 nm to about 380 nm; and activating the light sensitive molecule.

In certain preferred embodiments, the excitation wavelength is about 980 nm, and the emission luminescence of the UCNP is about 365 nm. The UCNP includes a core of cubic nanocrystals comprising α-Na (Y, Yb, Tm)$F_4$; an epitaxial shell formed from $CaF_2$; and an outer layer of an organic acid that covers the epitaxial shell, wherein the molar ratio of Tm/(Y+Yb+Tm) is a about 0.5±0.02%; and, the molar ratio of Yb/(Y+Yb+Tm) is greater than about 30%.

In certain preferred embodiments, the light sensitive molecule is activated at from about 340 nm to about 380 nm.

The light sensitive molecule preferably is a derivative of the 2-nitrobenzyl groups, 7-nitroindolinyl groups, coumarin moieties and their protected biological active macromolecules (e.g., caged organic dyes, photoactivable AMP, photoactivable GMP, caged DNA, caged RNA, caged proteins, and caged peptides.)

A variety of applications can benefit from the present invention, including remotely controlled in vivo drug delivery and gene therapy, and other in vitro and in vivo UV-mediated photochemistry.

BRIEF DESCRIPTION OF THE DRAWINGS

FIG. 2(a)-FIG. 2(b) show an exemplary transmission electron microscopy images of FIG. 2(a) a-NaYbF$_4$:Tm and FIG. 2(b) α-NaYbF$_4$:Tm@CaF$_2$ UCNPs.

FIG. 3(a)-3(c) show exemplary emission spectra: FIG. 3(a) UV emission spectra of α-NaYF$_4$:Yb,Tm@CaF$_2$ (solid line) and β-NaYF$_4$:Yb,Tm (dashed line) UCNPs with different $Yb^{3+}$-levels. FIG. 3(b) UV emission power dependence of α-NaYbF$_4$:Tm@CaF$_2$ UCNPs. FIG. 3 (c) $Yb^{3+}$-dependent UV emissions under 2.6 W/cm$^2$ 975-nm laser excitation (normalized to the total $Ln^{3+}$ concentration).

FIG. 8(c) The corresponding XRD patterns and index XRD data for β-NaYbF$_4$.

FIG. 14(b) the zeta potential of citric-UCNPs (−21.0 mV), PEI-UCNPs (24.4 mV), and cF-UCNPs (19.7 mV).

FIG. 21(a) Upconversion luminescence spectra, FIG. 21(b) photographic images, FIG. 21(c) PL decays at 805 nm in α-$NaYbF_4$: 0.5% Tm core and α-$NaYbF_4$:0.5% Tm@$CaF_2$ core/shell UCNPs diluted in hexane, and FIG. 21(d) contrasting upconversion luminescence spectra of 27-nm α-$NaYbF_4$:0.5% Tm@$CaF_2$ core/shell nanoparticles and 100-nm β-$NaYbF_4$: 0.5% Tm (hexagonal) UCNPs when excited by a 975-nm CW diode laser at power density of ~0.3 W/cm$^2$. The insets in FIGS. 2a and d show the absorption spectra of UCNPs normalized to 975-nm for the $^2F_{7/2} \rightarrow ^2F_{5/2}$ transition of Yb$^{3+}$ ions.

FIG. 23(a), FIG. 23(d) PL images; FIG. 23(b), FIG. 23(e) bright-field images; and FIG. 23(c), FIG. 23(d) superimposed images (bright-field and spectrally unmixed PL images) of unshaven mouse belly (upper panel) and shaved mouse back (lower panel). Inset in FIG. 23(f) shows the spectra of the NIR UC PL signals with background taken from the circled area.

FIG. 24(b) Bright-field image of the hind leg from a sacrificed rat (left) and PL image (right) of the deeply embedded UCNP-stained synthetic mesh around the rat femur. Scale bar: 2 cm.

DEFINITIONS

Figure 1:
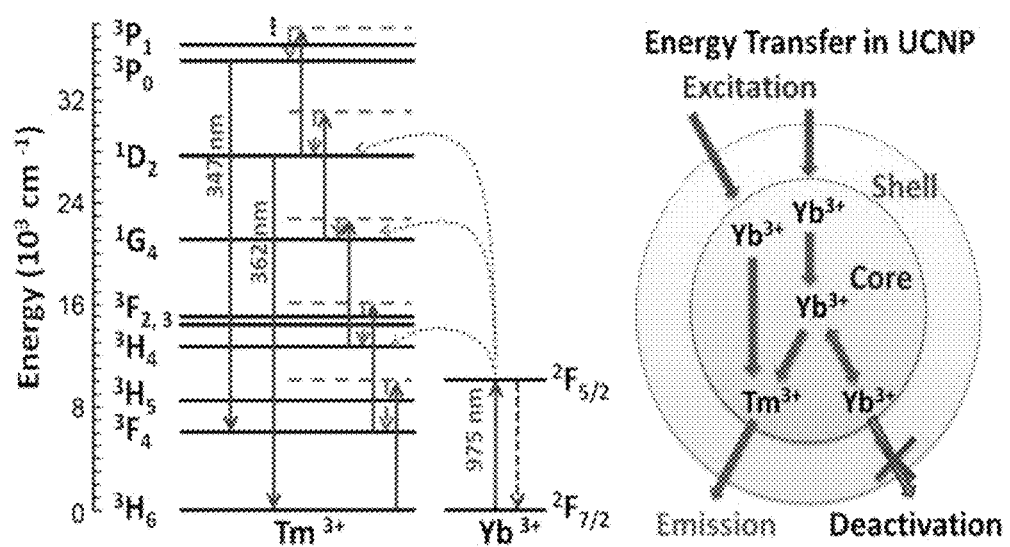
FIG. 1 shows an exemplary energy-level diagram of the $Yb^{3+}$-$Tm^{3+}$ upconverting system (left) and an energy transfer scheme of the core/shell UCNP (right).

Unless defined otherwise, all technical and scientific terms used herein have the same meaning as commonly understood by one of ordinary skill in the art to which this invention belongs.

As used herein, a "nanoparticle" refers to a particle between about 100 nm and about 1 nm.

As used herein, "biocompatible" describes a material that elicits an appropriate host response without any adverse effects, and is compatible with living cells, tissues, organs, or systems, and posing no risk of injury, toxicity, or rejection by the immune system.

As used herein, "upconversion" refers to a process in which the sequential absorption of two or more photons leads to the emission of light at shorter wavelength than the excitation wavelength.

As used herein, "UCNP" refers to upconversion nanoparticle.

DETAILED DESCRIPTION OF THE INVENTION

The invention is based in part on the discovery of novel biocompatible UCNPs, methods of syntheses and applications thereof.

In an exemplary embodiment, the invention provides a novel core/shell α-$NaYbF_4$:0.5% Tm@$CaF_2$ nanoparticle with efficient NIR$_{in}$-NIR$_{out}$ UC PL for high-contrast in vivo bioimaging in deep tissue. An epitaxial hetero-shell $CaF_2$ enhances the PL intensity of α-$NaYbF_4$:0.5% Tm nanoparticles 35 times, for a quantum yield of 0.6% under low-energy excitation of 0.3 W/cm$^2$. Whole-body imaging of a BALB/c mouse intravenously injected with aqueous core/shell nanoparticles (700 pmol/kg) showed a SNR of 310, about 10-fold higher than that previously reported for in vivo imaging by UCNPs. The retention of NIR$_{in}$-NIR$_{out}$ $NaYbF_4$:Tm@$CaF_2$ nanoparticles on synthetic scaffolds surrounding the centimeter-deep femur of a rat was successfully visualized, demonstrating these particles' potential for tissue engineering applications. Furthermore, upconverted photoluminescent emissions of $NaYbF_4$:Tm@$CaF_2$ nanoparticles in a cuvette were clearly imaged with high contrast against the light-scattering background, even with through a 3.2-cm pork tissue between the laser source and cuvette. These capabilities of engineered NIR$_{in}$-NIR$_{out}$ UC PL nanoprobes promise their widespread use in biomedical and clinical applications.

Core/Shell UCNPs

Ultraviolet (UV) radiation-mediated photochemical reactions are extremely important in materials science, advanced imaging, chemical biology and drug-delivery systems. For biomedical applications, UV photons can manipulate the functions of biomolecules or mediate on-demand drug release in live systems via effective photoactivation. However, commonly used UV lamps or lasers produce an excessively large area of UV radiation and have major drawbacks, such as severe phototoxicity and significantly limited tissue penetrability. Thus, an in-situ generation of UV light utilizing nanoparticles with a biocompatible low-energy excitation is quite desirable since it can spatiotemporally restrict photochemical reactions in the nanometer region with minimal photo-damage and significantly enhanced light penetration depth.

When excited by high-peak power (~$10^8$ W/cm$^2$) pulsed lasers, organic luminophores and semiconductor nanocrystals can produce two- or three-photon excited luminescence in the visible region. Yet, upconversion from NIR to UV via this direct multi-photon excitation is inefficient, requiring extremely high pulse energy. An excellent alternative is the lanthanide (Ln)-doped UCNP.

Because Ln$^{3+}$ dopants have long lifetimes and a ladder-like hierarchy of excited states, UCNPs can absorb NIR light from a continuous wave (CW) light source and emit photons at shorter wavelengths that extend to the UV region. In addition, such an upconversion process requires much lower photo-excitation power (1-10$^3$ W/cm$^2$) and is significantly more efficient than the conventional, multi-photon-absorption-based processes. An inexpensive CW NIR laser can effectively excite UCNPs for UV-mediated photoreactions. However, the application of UV-emitting UCNPs for biological systems has been extremely challenging due to the severe quenching that is induced by high-frequency hydroxyl (OH) vibrations of water molecules and intracellular biomolecules. Thus, a new synthetic strategy is required in order to significantly improve UV emission output. Disclosed herein is on a direct observation and mechanistic understanding of sensitizer concentration dependent four-photon induced NIR to UV upconversion enhancement in CaF$_2$-coated α-NaYF$_4$:Yb, Tm core/shell UCNPs. It is demonstrated that UV output of UCNPs can be systematically enhanced by increasing the Yb$^{3+}$ concentration in UCNP cores. It is also shown that the optimized UV-emitting UCNPs (α-NaYbF$_4$:Tm@CaF$_2$) can rapidly activate nonfluorescent caged fluorescein to a fluorescent state inside live cells, validating the applicability of such enhanced UV-emitting UCNPs for biocompatible photoactivation. In a typical UV-emitting UCNP system, the sensitizer Yb$^{3+}$ absorbs one 975-nm photon at a time and transfers the energy to a neighboring Tm$^{3+}$, which has an electron that is sequentially pumped to the UV emission level. In regard to photochemical reactions, 362 nm is the most commonly used wavelength and its corresponding upconverting process can be ascribed to the $^1D_2$-$^3H_6$ transition which can, in turn, be attributed to a four-photon upconversion process (FIG. 1). The population of the $^1D_2$ state can be denoted by a simplified steady-state approximate equation, such as in equation (a), as follows.

$$N_4 = \frac{W_3 W_2 W_1 W_0 (N_{YbO})^4}{B_4 B_3 B_2 B_1} (\sigma I)^4 N_0 \quad (a)$$

In this equation, the subscripts i=0-4 correspond to different intermediate states of Tm$^{3+}$ ($^3H_6$, $^3F_4$, $^3H_4$, $^1G_4$, and $^1D_2$, respectively), $B_i$ is the non-radiative rate of excited Tm$^{3+}$, $W_i$ is the energy-transfer rate from excited Yb$^{3+}$ to Tm$^{3+}$, c is the cross-section of Yb$^{3+}$ absorption at 975 nm (the constant), I is the laser power density, $N_0$ and $N_{YbO}$ are the ground state populations of Tm$^{3+}$ and Yb$^{3+}$, respectively, and $N_4$ represents the population of the $^1D_2$ state (see Examples details).

Since the 362-nm UV emission intensity is proportional to the population of the $^1D_2$ state (i.e., $N_4$), one can conclude that the variables in this equation ($N_0$, $B_i$, $W_i$ and $N_{YbO}$) can be optimized to obtain enhanced UV emission under a fixed laser intensity (I). However, $N_0$ and $B_i$ are determined by the concentration of Tm$^{3+}$. To minimize $B_i$, the optimal doping ratio of Tm$^{3+}$ must be less than 2%. Additionally, since lower concentrations of Tm$^{3+}$ favor energy transfer to higher energy excited levels ($^1D_2$), in our study the Tm$^{3+}$ ratio was fixed at 0.5%. Consequently, the only two tunable variables in equation (a) are $W_i$ and $N_{YbO}$. In principle, both of these variables are proportional to the Yb$^{3+}$ concentration, since elevating the Yb$^{3+}$ doping concentration not only increases the energy transfer factor $W_i$ by reducing the distance between Yb$^{3+}$ and Tm$^{3+}$, it also increases the ground state population of Yb$^{3+}$ ($N_{YbO}$).

Thus, although higher concentrations of Yb$^{3+}$ should lead to stronger UV emissions, such an increase can also lead to elevated levels of surface Yb$^{3+}$ ions that are deactivated by surface quenchers. This deactivation effect becomes particularly severe in the case of a high-order multi-photon upconversion process. Thus, the optimal Yb$^{3+}$ doping ratio in non-core/shell UCNPs has been suggested to be 20-30%.

A unique core/shell structure is disclosed herein that effectively eliminates energy quenching effects. Thus, the UV output of core/shell UCNPs can be exclusively controlled by the Yb$^{3+}$ doping level of UCNP cores (FIG. 1).

Also disclosed herein is a convenient one-pot synthesis of a family of CaF$_2$-coated α-NaYF$_4$:Yb,Tm (i.e., α-NaYF$_4$:Yb,Tm@CaF$_2$) core/shell UCNPs with varying Yb$^{3+}$ content. α-NaLnF$_4$ UCNPs were chosen as cores due to their high maneuverability and controllability. CaF$_2$ was chosen as the epitaxial shell because of its ideal optical transparency, high crystallizability and negligible lattice mismatch with α-NaLnF$_4$ (for α-NaYF$_4$, a=5.448 Å; for CaF$_2$, a=5.451 Å), all desirable properties for forming a homogenous core/shell interface to minimize quenching sites from the α-NaLnF$_4$ cores. In addition, a CaF$_2$ shell is likely to be more biocompatible than the widely used NaLnF$_4$ shell, as CaF$_2$ is an endogenous component in living systems.

Figure 2A:
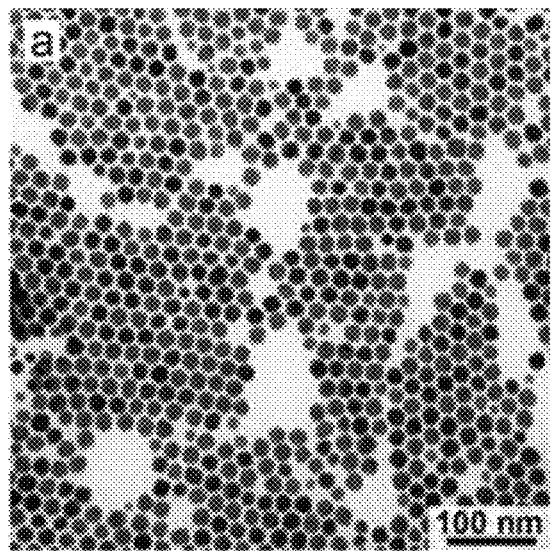

In the synthesis procedure, the trifluoroacetate precursors of Na$^+$ and Ln$^{3+}$ (i.e., Y$^{3+}$, Yb$^{3+}$, Tm$^{3+}$) in corresponding concentrations are mixed into a high temperature thermolysis pot (i.e., about 310° C.) to first form the intermediate α-NaLnF$_4$ core UCNPs with a monodisperse size of about 22±3 nm (FIG. 2a). The calcium trifluoroacetate precursor is then injected to initiate an epitaxial growth of the CaF$_2$ shell. This stepwise injection strategy efficiently modulates the thermolysis of different precursors, while the continuous reaction preserves sufficiently activated growth sites on the intermediate UCNPs. These advantages result in high quality α-NaLnF$_4$@CaF$_2$ UCNPs with a uniform cubic shape and a mean edge length of about 27 nm±2 nm (FIG. 2b). Since both α-NaLnF$_4$ and CaF$_2$ are cubic phase crystals, the nanocubic morphology indicates a high UCNP crystallinity level. The Ca:Ln ratio in the UCNPs estimated from the geometric volume of core and shell structures from TEM is 5.06, and this is quite close to the atomic emission spectroscopy elemental analysis result of 4.55 (see Examples).

Figure 3C:
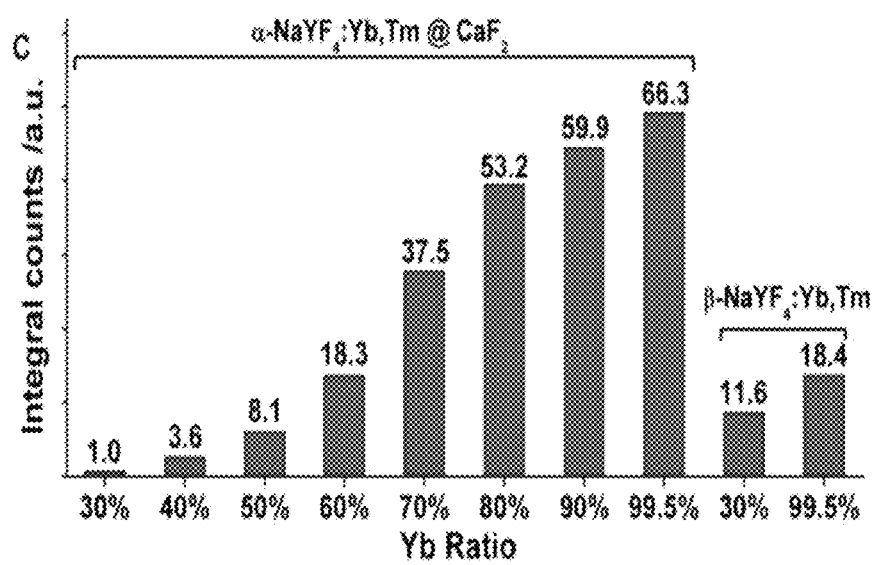
Figure 10:
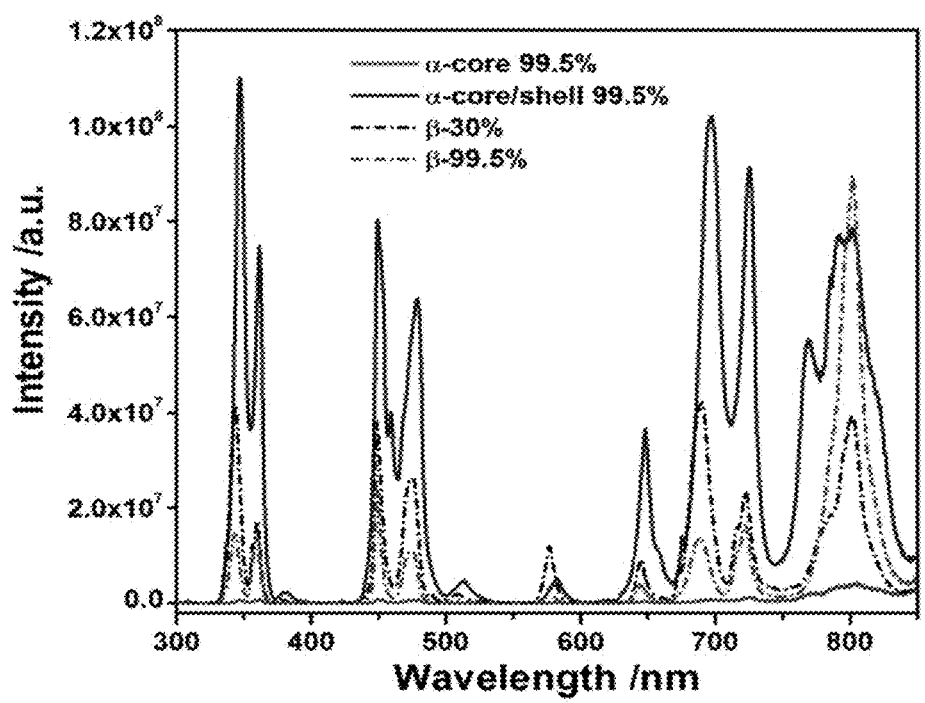
FIG. 10 shows exemplary upconverting emission spectra of α-NaYbF$_4$:Tm, α-NaYbF$_4$:Tm@CaF$_2$, β-NaYF$_4$:30% Yb, 0.5% Tm, and β-NaYbF$_4$:0.5% Tm UCNPs, measured under 10$^3$ W/cm$^2$ of 975-nm excitation (the $Yb^{3+}$ absorptions of these UCNPs were normalized to that of 30 nm β-NaYF$_4$:20% Yb, 2% Er@β-NaYF$_4$ UCNPs).
Figure 11:
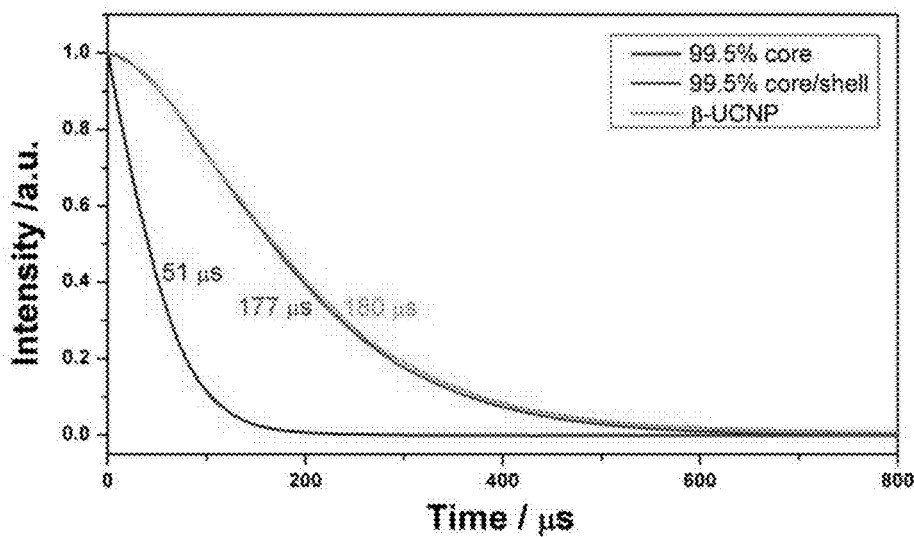
FIG. 11 shows exemplary upconverting lifetimes of $^1D_2$-$^3H_6$ emissions (362 nm) in α-NaYbF$_4$:Tm (core), α-NaYbF$_4$:Tm@CaF$_2$ (core/shell), and β-NaYbF$_4$:Tm UCNPs.

The upconversion emission spectra of UCNPs were measured under CW excitation at 975 nm with a power density of 10 W/cm$^2$, and were normalized to the total Ln$^{3+}$ concentration. FIG. 3 shows a prominent enhancement of the UV emission peak at 362 nm; as the inner core Yb$^{3+}$-content is increased its intensity grows. The α-NaYbF$_4$:Tm@CaF$_2$ UCNPs (a maximum doping of Yb$^3$) demonstrated the most intense UV emission, 66 times greater than that of 30% Yb$^{3+}$-doped core/shell UCNPs. A quartic dependence on the laser power illustrates that the emission at 362 nm is indeed a four-photon process.

β-phase NaLnF$_4$ has been suggested to be a much more efficient host lattice for upconverting materials than its α-phase allotrope. In addition, large UCNPs are considered to be much brighter than their smaller counterparts. For this reason, UV emission of the optimized α-NaYbF$_4$:Tm@CaF$_2$ UCNPs is compared with those of β-NaYbF$_4$: 0.5% Tm (ca. 90 nm) and β-NaYF$_4$:30% Yb, 0.5% Tm (ca. 140 nm) UCNPs. It was observed that the UV emissions of small α-NaYbF$_4$:Tm@CaF$_2$ UCNPs are even stronger than those of much larger β-NaYbF$_4$:Tm and β-NaYF$_4$:30% Yb, Tm UCNPs (FIG. 3c). The quantum yield of UV emission from α-NaYbF$_4$:Tm@CaF$_2$ UCNPs is measured to be 0.1%, which is about 7.5 times higher than that of 99.5% Yb$^{3+}$-doped β-UCNPs (FIG. 10). The core/shell α-UCNPs and large β-UCNPs were also characterized by quite similar lifetimes of $^1D_2$-$^3H_6$ emission (~180 μs) (FIG. 11). These facts suggest that the CaF$_2$ shell effectively blocked the non-radiative deactivation route for those excited Yb$^{3+}$ that were on the surface, thus allowing W$_i$ and N$_{Yb0}$ to increase in equation (a) and to enhance UV upconversion emission output. It was found that Yb$^{3+}$ concentration dependent visible and NIR emission increase from α-NaYF$_4$:Yb,Tm@CaF$_2$ UCNPs, but with smaller slopes, as their corresponding population density equations have a lower power dependence on N$_{Yb0}$ (FIG. 9).

Caged fluorescein can recover fluorescence activity upon removing a photosensitive group (e.g., o-nitrobenzyl group) via brief irradiation with UV light. This ability to recover fluorescence is important for analyzing cell lineages and probing cellular protein dynamics. However, such photolysis reactions cannot be achieved under irradiation with a low-power NIR CW laser.

Figure 4:
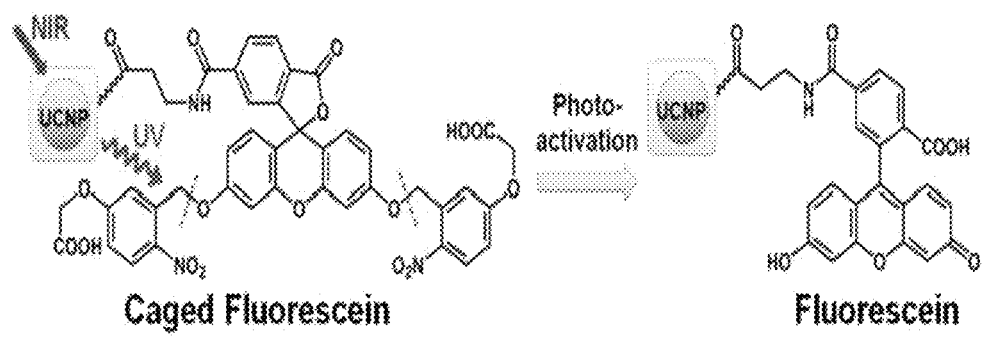
FIG. 4 illustrates photo-activation of caged fluorescein conjugated UV-enhanced UCNPs (cF-UCNPs).

To validate the applicability of NIR absorbing and UV emitting UCNPs for biocompatible photo-activation, α-NaYbF$_4$:Tm@CaF$_2$ UCNPs was conjugated with a commercially available caged fluorescein, and probed its photolysis reaction in live cells via irradiation at 975-nm with NIR CW laser (FIG. 4). The preferable conjugation protocol employed 1-Ethyl-3-(3-dimethylaminopropyl) carbodiimide hydrochloride (EDC.HCl) and N-hydroxysulfosuccinimide sodium salt (sulfo-NHS) to catalyze the covalent binding of amino and carboxyl groups. The reaction is preferably incubated in PBS buffer.

Figure 12:
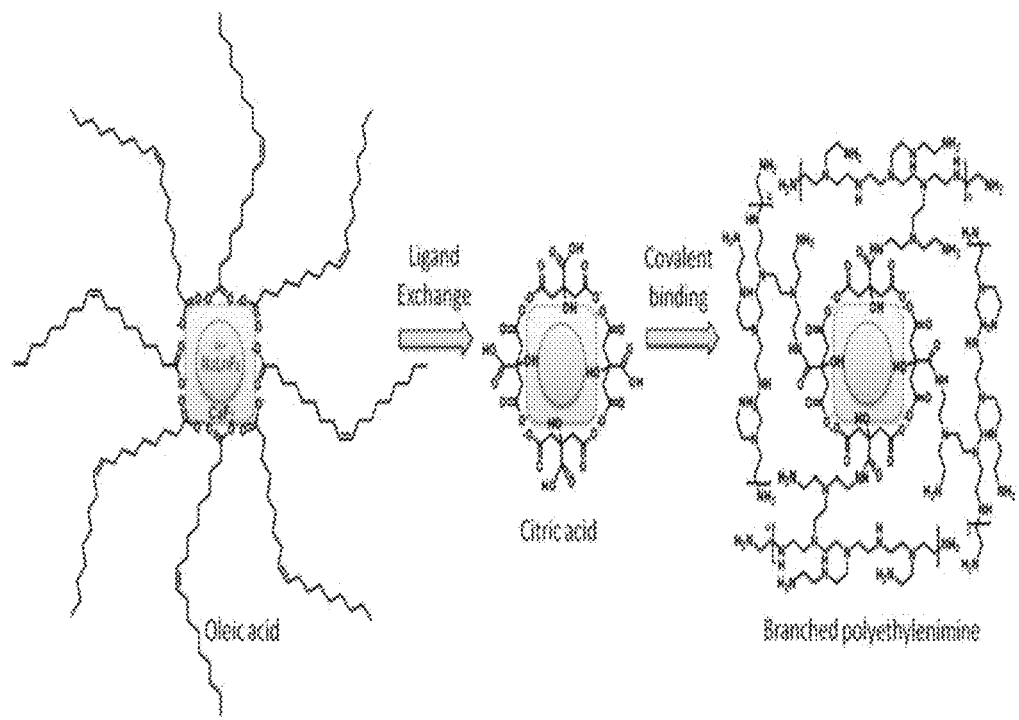
FIG. 12 shows exemplary surface modification scheme for α-NaLnF$_4$@CaF$_2$ UCNPs.
Figure 13:
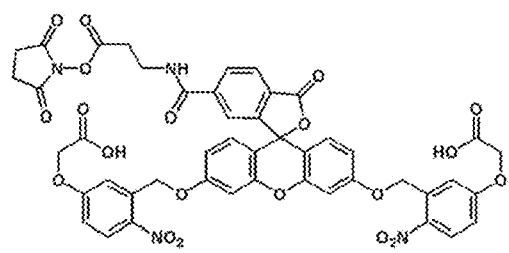
FIG. 13 shows the molecule structure of 5-carboxyfluorescein-bis-(5-carboxymethoxy-2-nitrobenzyl) ether, β-alanine-carboxamide, succinimidyl ester.
Figure 14A:
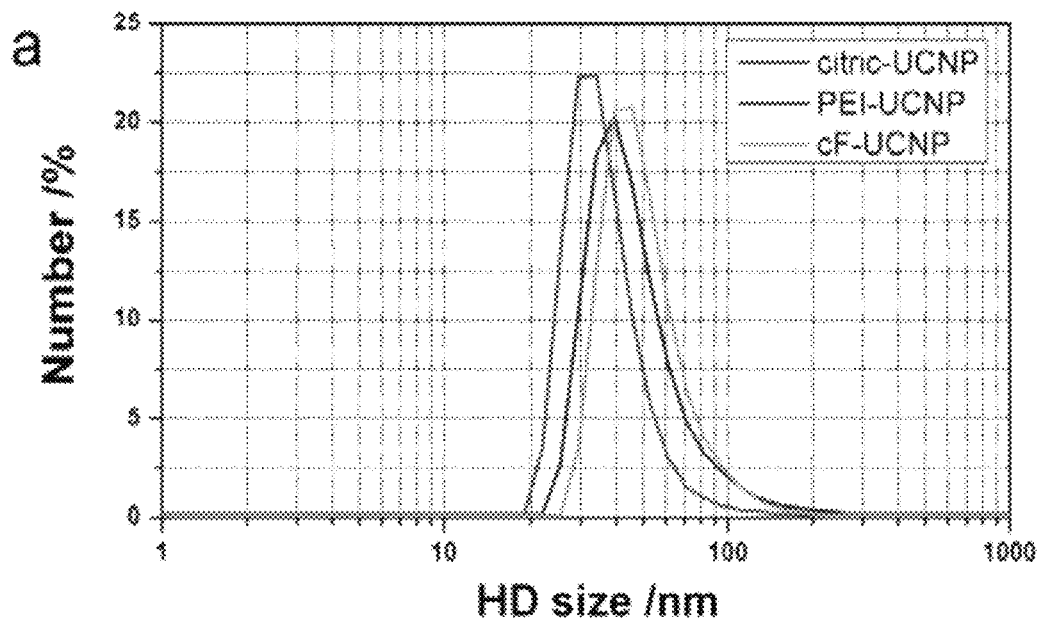
FIG. 14(a)-FIG. 14(b) show FIG. 14(a) the hydrodynamic (HD) size distributions of citric-UCNPs, PEI-UCNPs, and cF-UCNPs with peak values of 37.9 nm, 48.4 nm, and 52.0 nm, respectively.
Figure 14B:
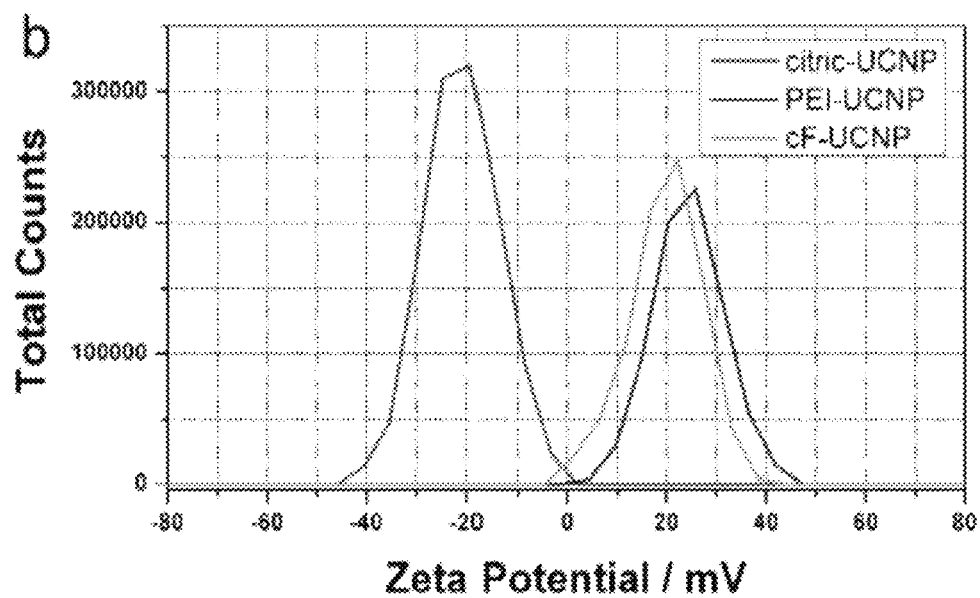
Figure 15:
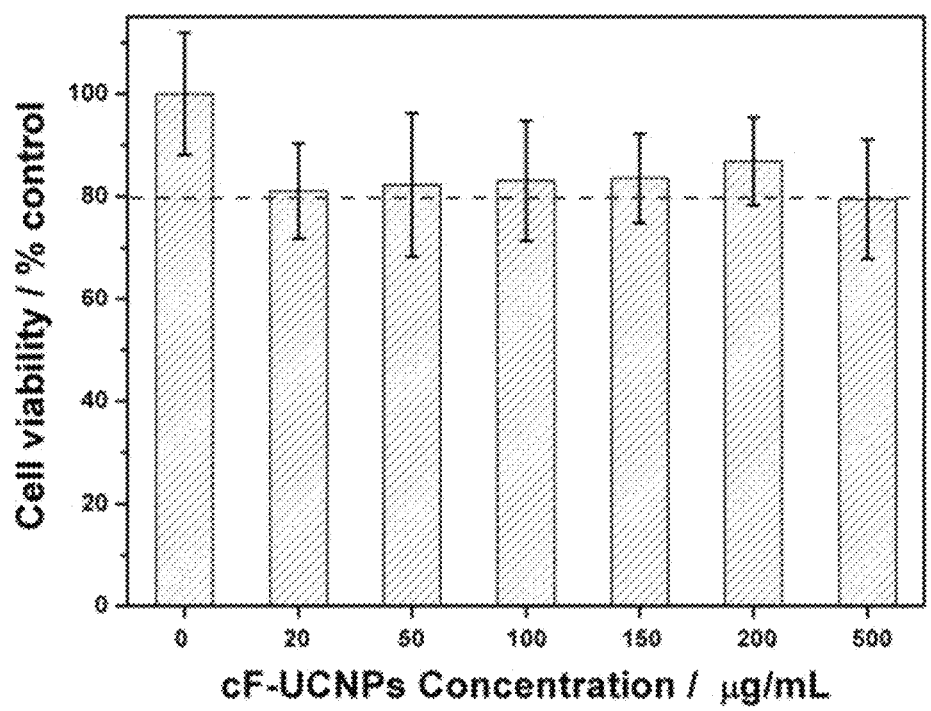
FIG. 15 shows exemplary HeLa cell viabilities after incubating for 24 h with different concentrations of cF-UCNPs.

In this study, α-NaYbF$_4$:Tm@CaF$_2$ UCNPs were first transferred to water via a ligand exchange with citric acid. Second, branched polyethylenimine (PEI) was conjugated with citric acid-coated UCNPs, which were further linked to succinimidyl ester-derivatized caged fluorescein (FIGS. 12 and 13). The caged fluorescein-labeled UCNPs (cF-UCNPs) have a mean hydrodynamic size of 52 nm and their potential value is 19.7 mV, allowing cellular uptake of cF-UCNPs to occur. The HeLa cell viability test of cF-UCNPs showed no evident cytotoxicity up to 500 μg/mL (FIG. 15). Due to their unique CaF$_2$ shell, these water-dispersed UCNPs were able to maintain 37% of their original UV emission intensity in hexane.

Figure 5:
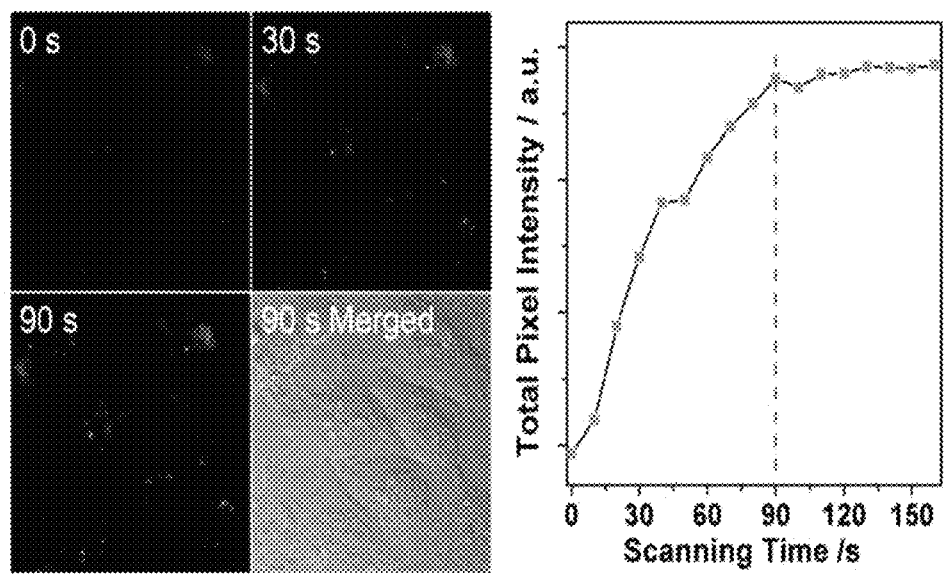
FIG. 5 shows exemplary photoactivation of cF-UCNPs in live HeLa cells by 975-nm laser confocal microscope scanning. The evolution of fluorescein emission intensity indicates that uncaging is completed at 90 s.
Figure 6A:
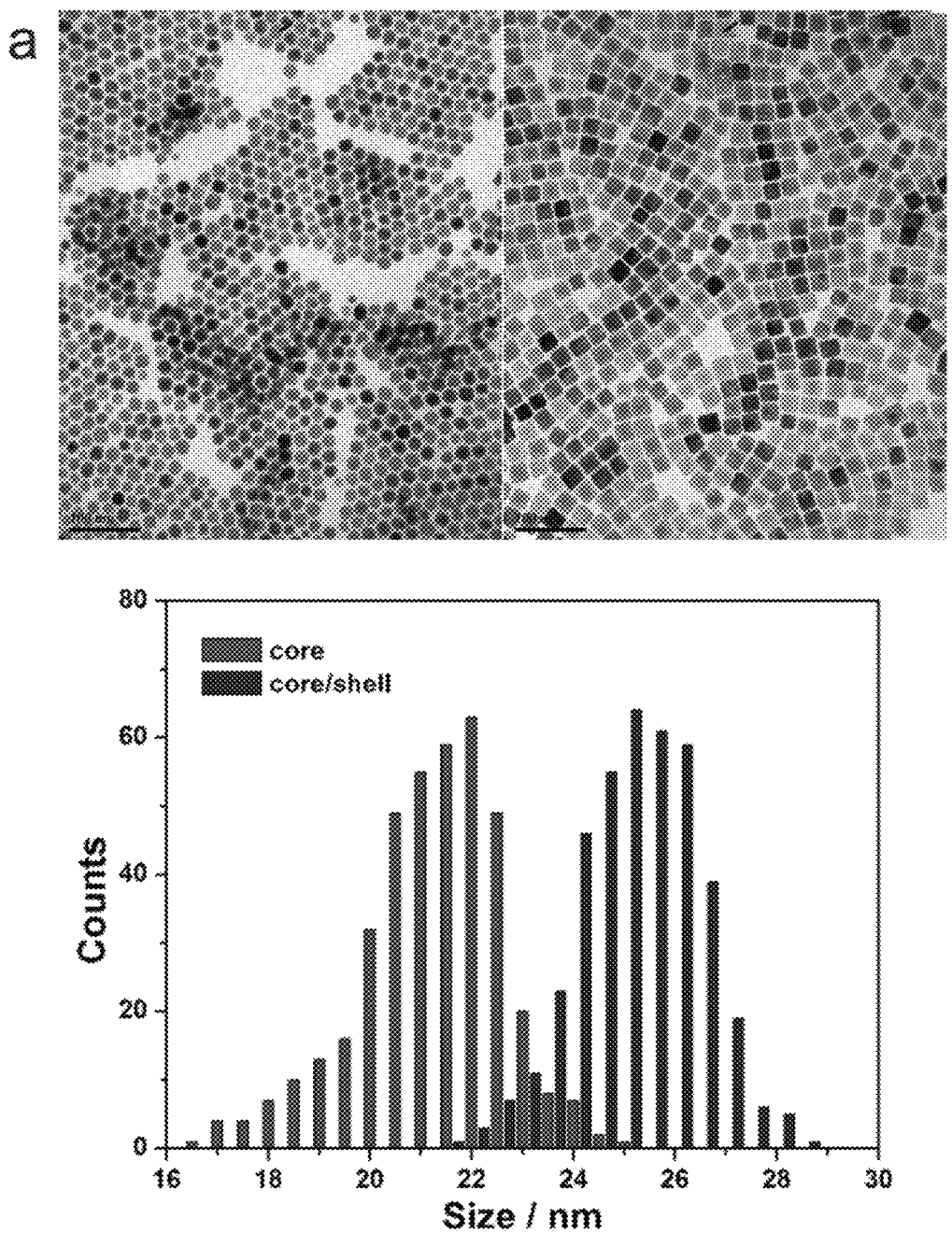
FIG. 6(a)-FIG. 6(h) show exemplary TEM images of α-NaLnF$_4$ core (left), α-NaLnF$_4$@CaF$_2$ core/shell (middle) UCNPs, and their corresponding size distributions (right). The $Yb^{3+}$ doping level was FIG. 6(a) 30%, FIG. 6(b) 40%, FIG. 6(c) 50%, FIG. 6(d) 60%, FIG. 6(e) 70%, FIG. 6(f) 80%, FIG. 6(g) 90%, and FIG. 6(h) 99.5%, respectively.
Figure 6B:
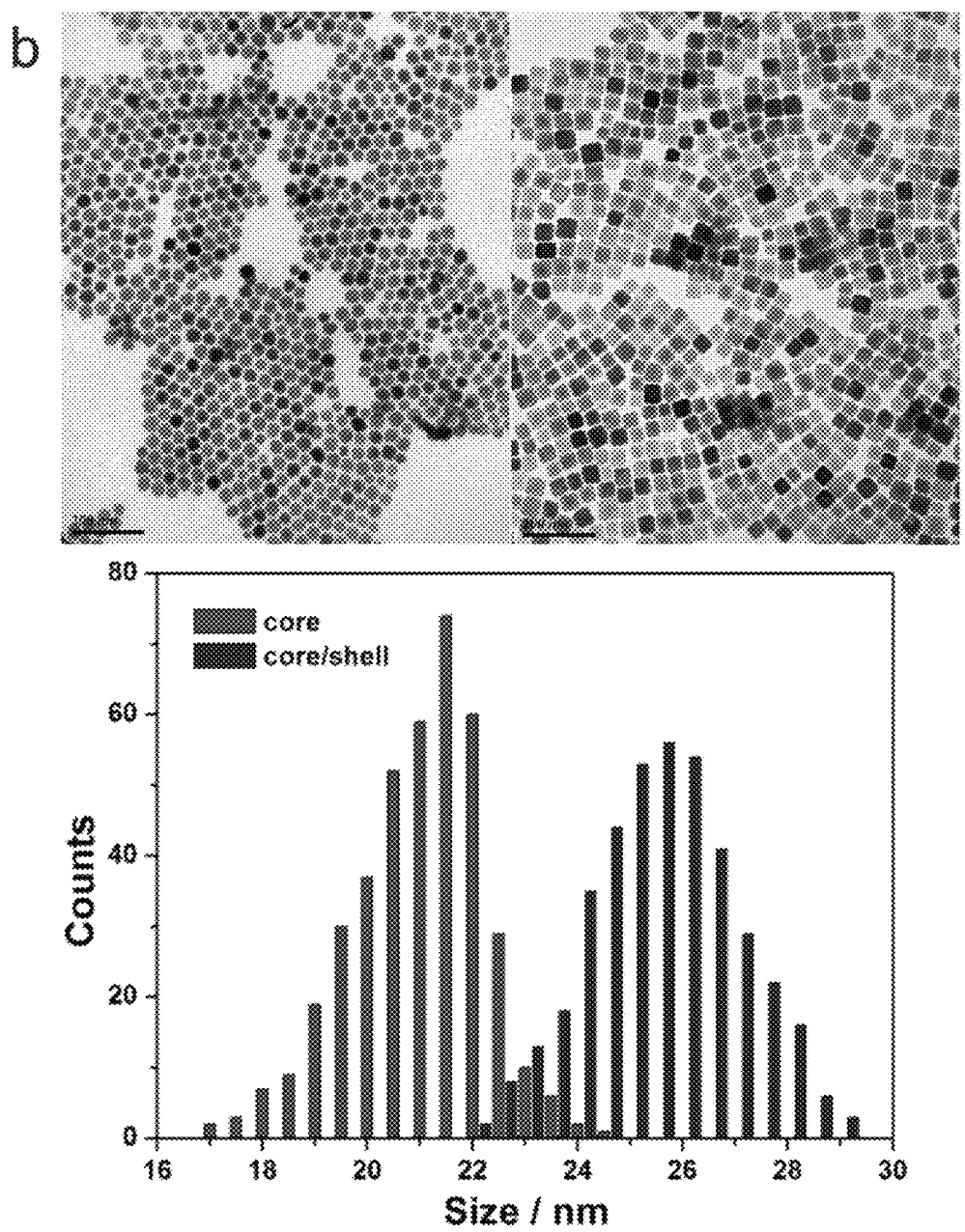
Figure 6C:
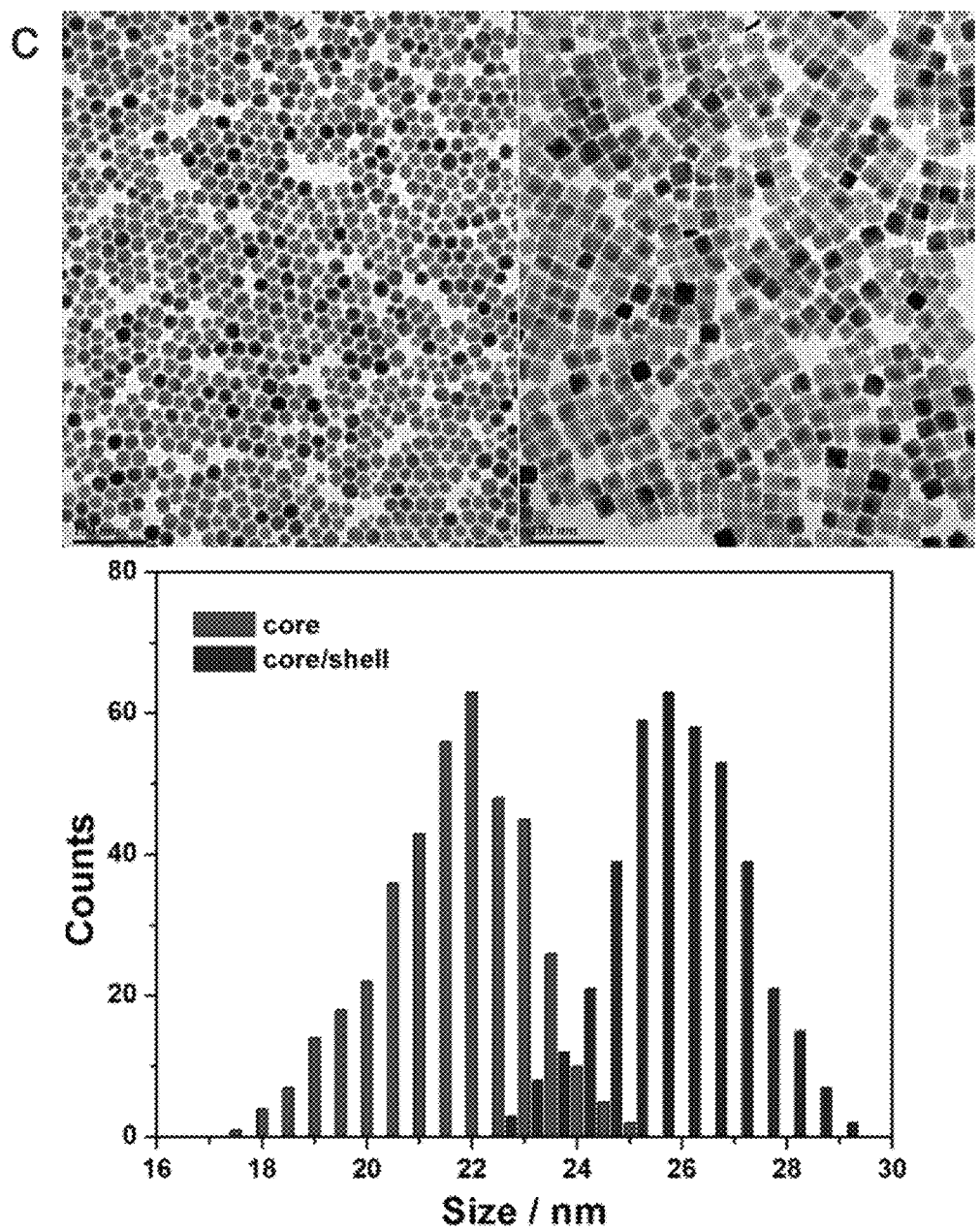
Figure 6D:
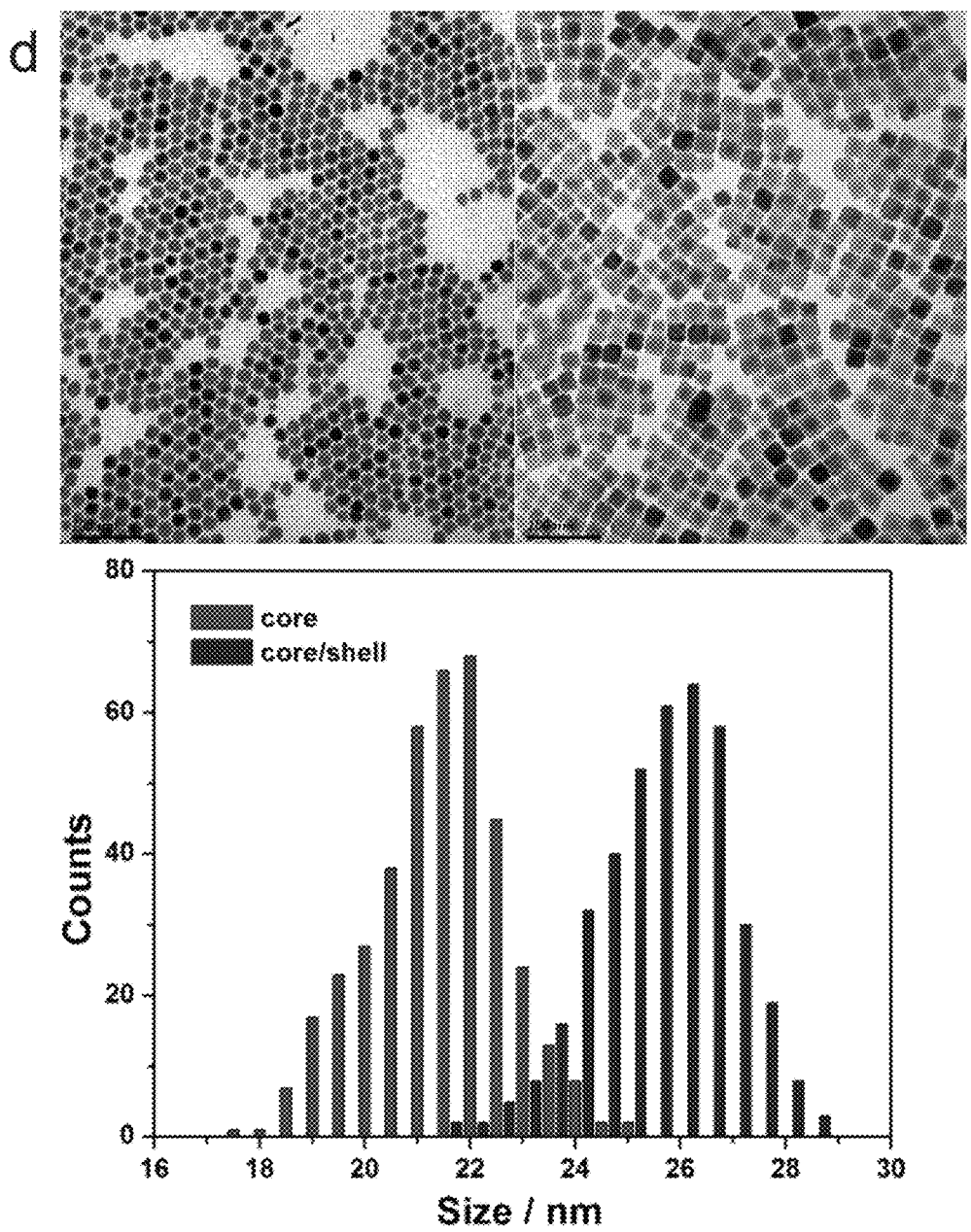
Figure 6E:
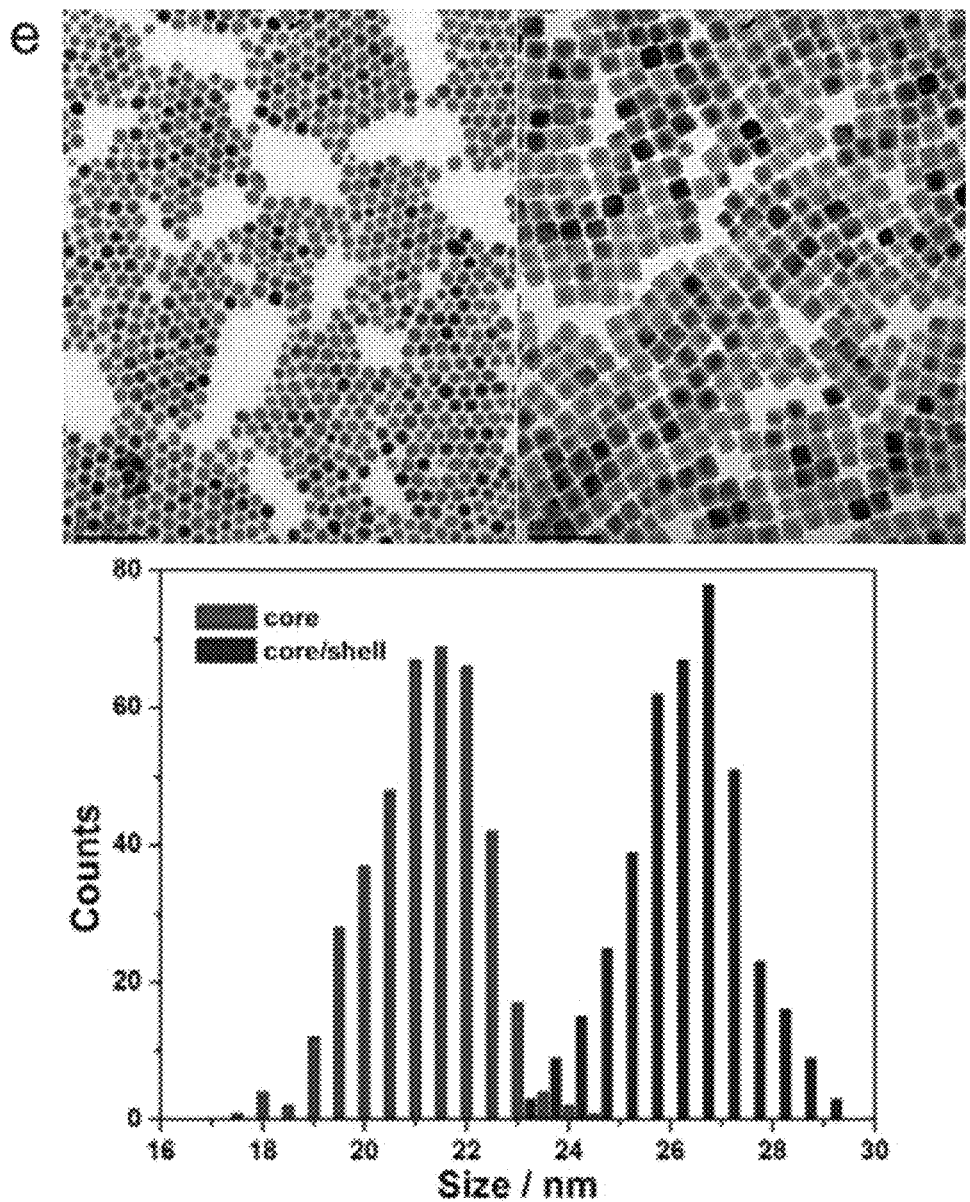
Figure 6F:
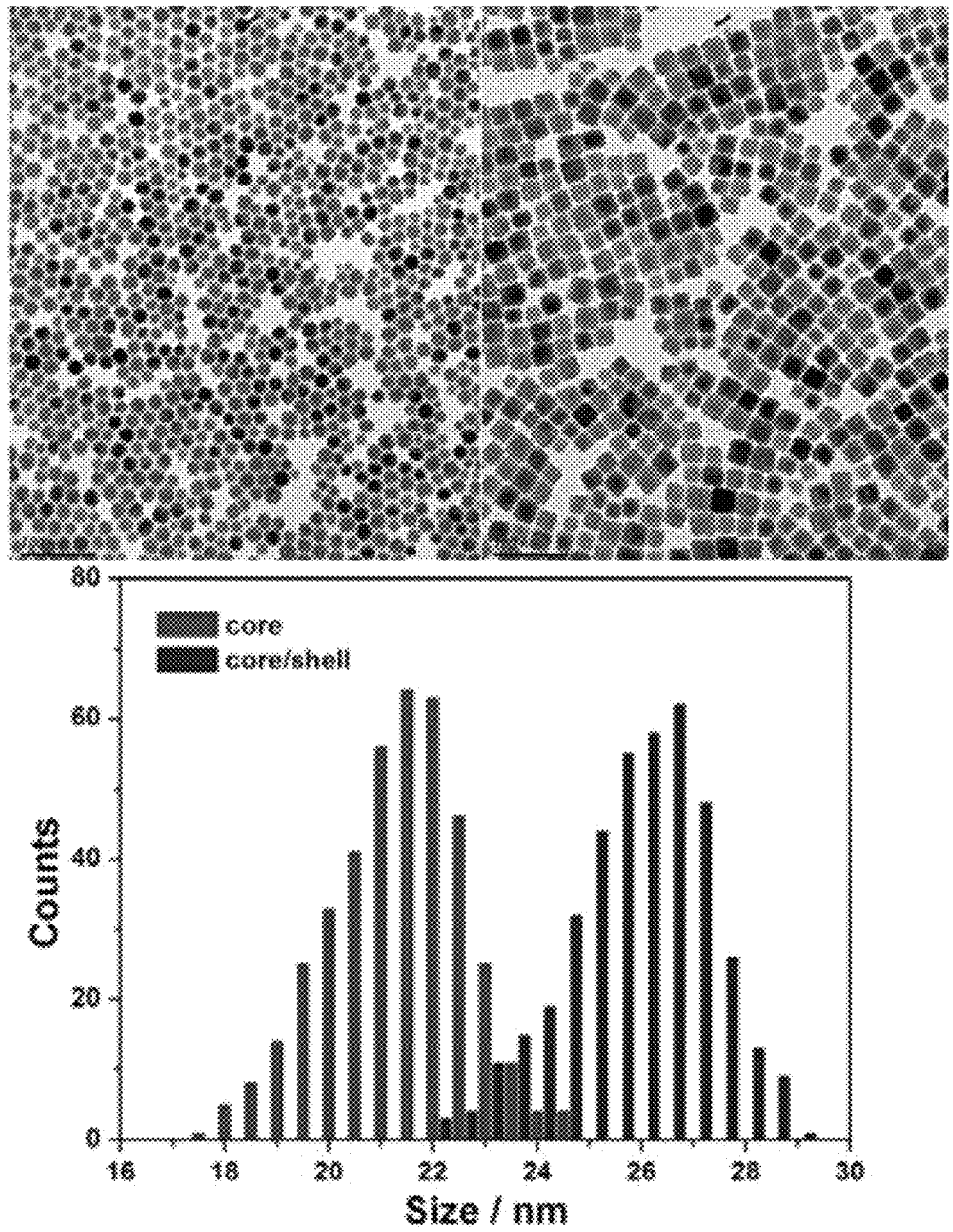
Figure 6G:
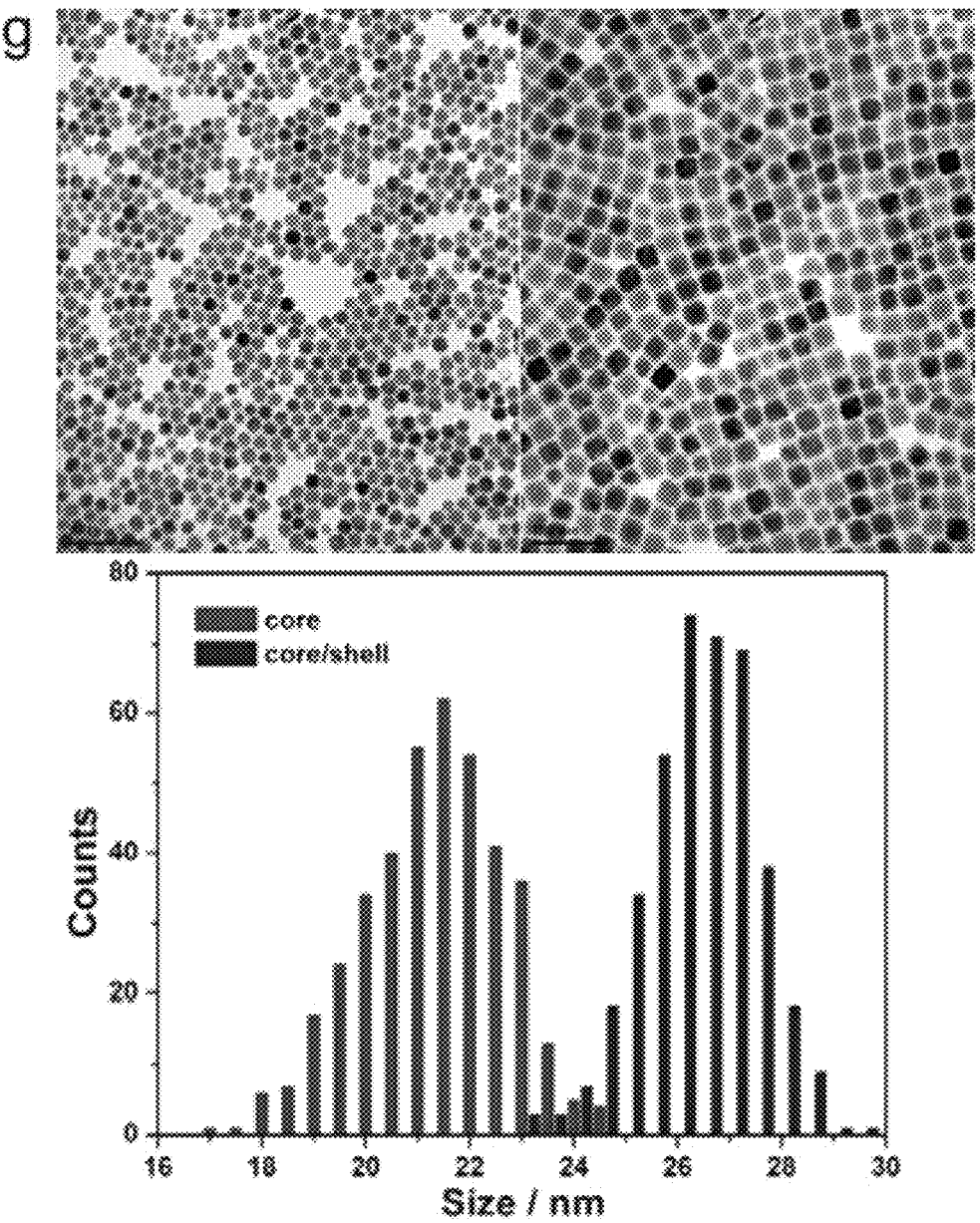
Figure 6H:
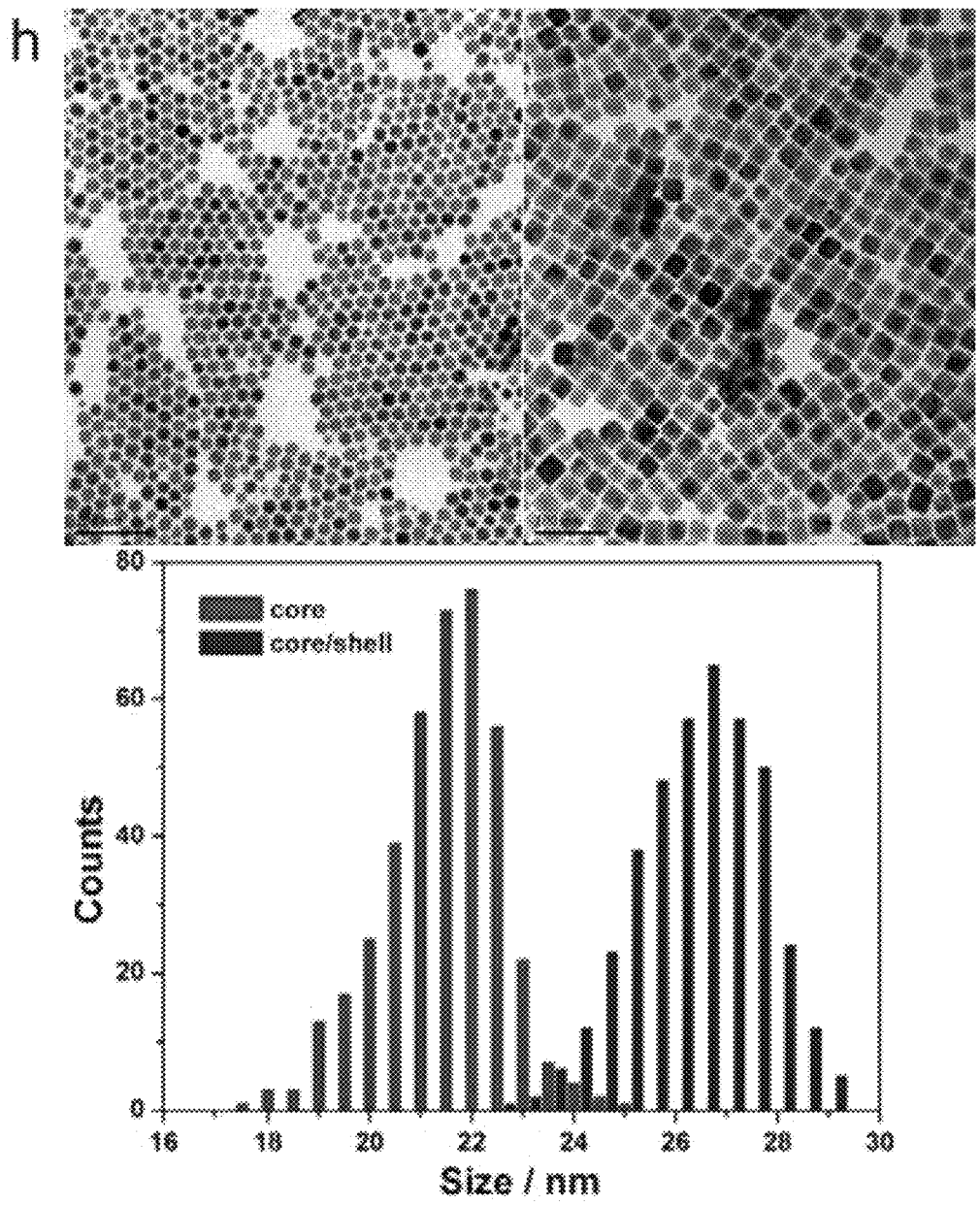
Figure 16:
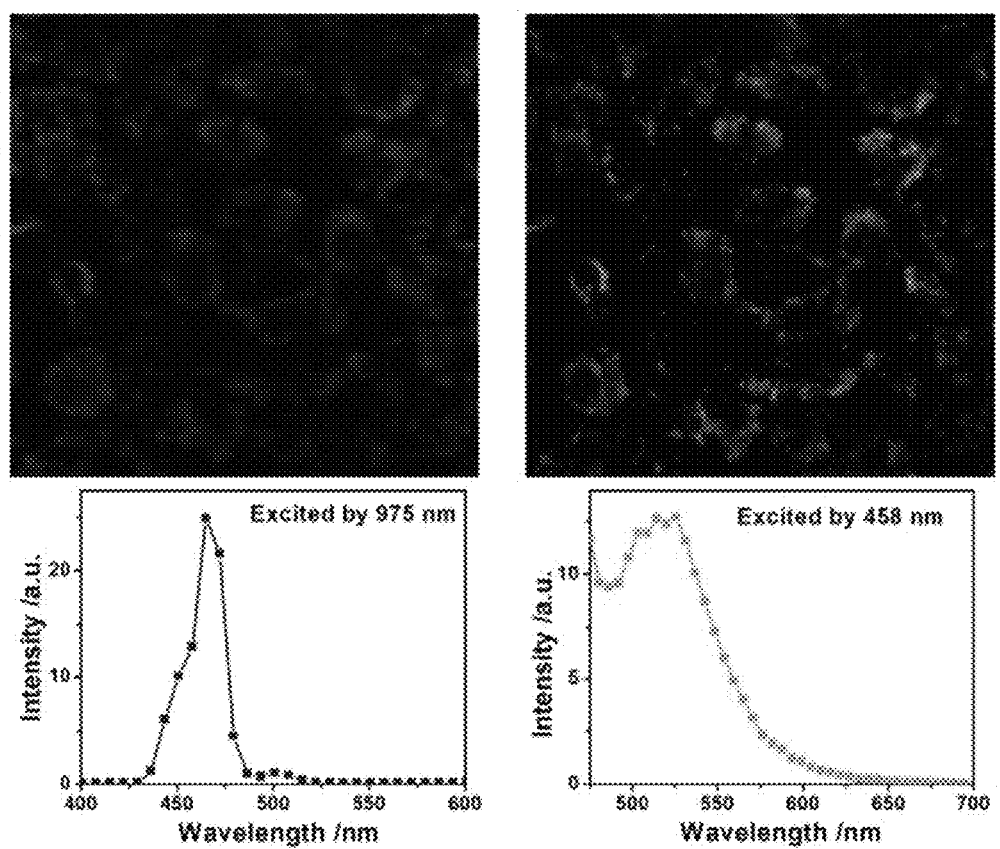
FIG. 16 shows exemplary microscopic images and in situ emission spectra of cF-UCNP-labeled HeLa cells obtained by confocal microscope. Blue signal indicates α-NaYbF$_4$:Tm@CaF$_2$ UCNPs, and green signal indicates uncaged fluorescein.
Figure 17:
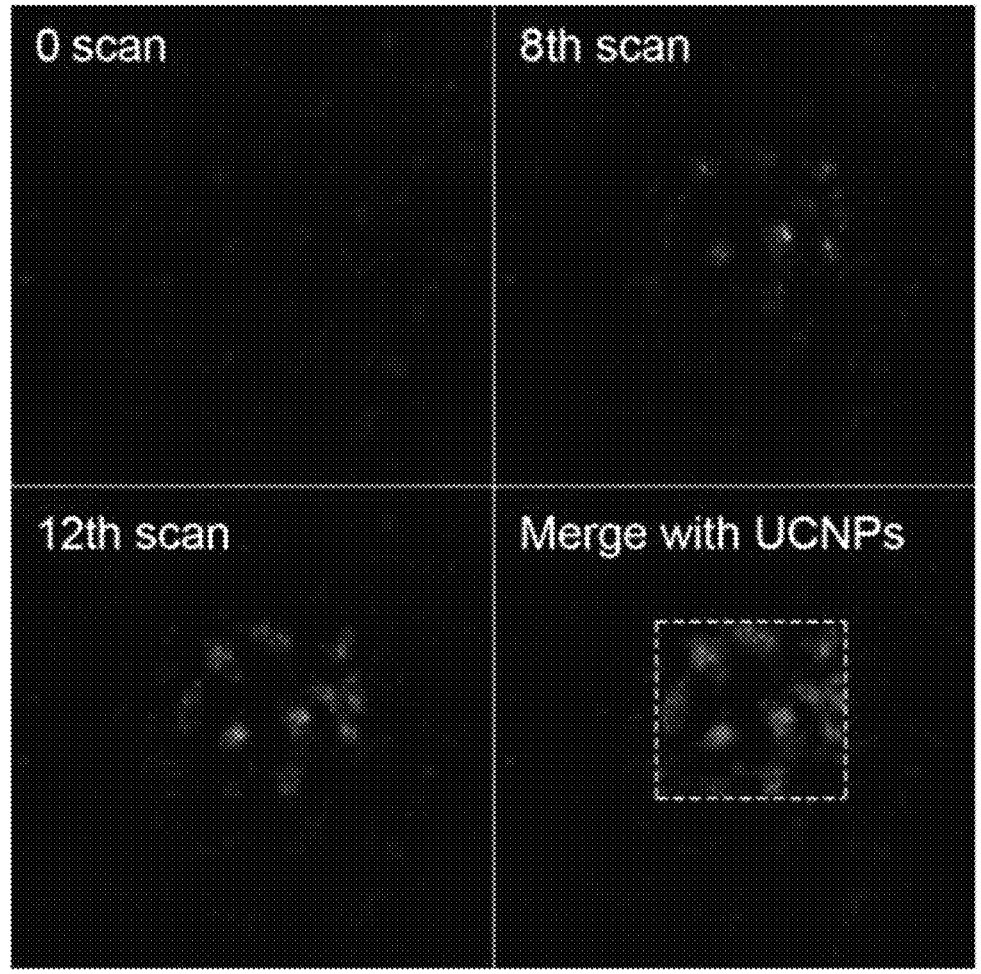
FIG. 17 shows exemplary photoactivation of cF-UCNPs inside HeLa cells by a two-photon microscope. The 975-nm pulsed laser was applied within the area bordered by red marks. The green signals from uncaged fluorescein matched the location of blue emission from UCNPs.
Figure 18:
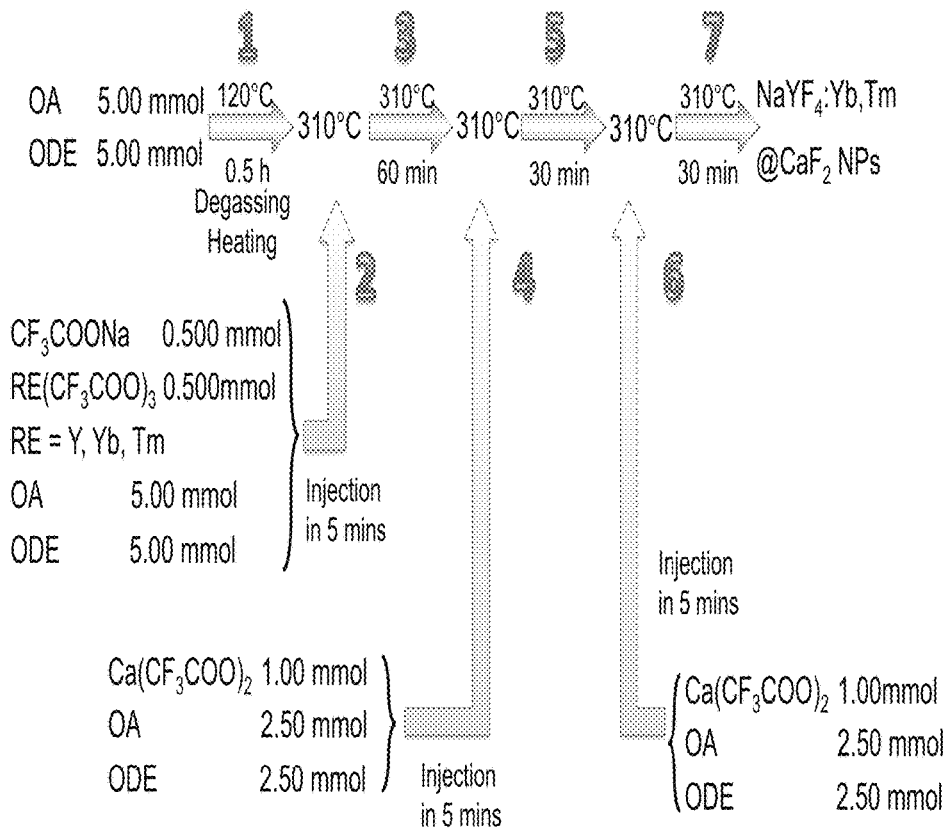
FIG. 18 illustrates synthesis of α-NaYF$_4$:Yb,Tm@CaF$_2$. In a three-neck reaction flask, a mixture of oleic acid (OA, 8 mmol) and 1-octadecene (ODE, 8 mmol) was heated to 120° C. to degas trace oxygen and water (step 1). It was subsequently heated to the thermolysis reaction temperature (310° C.) under argon protection. The precursor solution for α-NaYF$_4$:Yb,Tm core was prepared by dispersing $CF_3COONa$ (0.500 mmol) and $Ln(CF_3COO)_3$ (Ln=Y, Yb, Tm, 0.500 mmol in total) within oleic acid (5 mmol) and 1-octadecene (5 mmol). After vacuum degassing at 120° C., the core precursor solution was injected into the reaction flask at a rate of ca. 1 mL/min (step 2). Then the thermolysis reaction was kept at 310° C. for 1 h under dry argon flow (step 3). $Ca(CF_3COO)_2$ (2.000 mol), oleic acid (5 mmol), and 1-octadecene (5 mmol) was mixed and vacuum degassed at 120° C. to make the shell precursor solution. This solution was injected in twice with an equal volume (step 4, 6), followed by 30 min incubation at 310° C. after each injection (step 5, 7). The α-NaLnF$_4$@CaF$_2$ UCNPs were precipitated by adding ethanol to the cooled reaction flask, and centrifugal washing twice with hexane/ethanol. The resulting white powder can be re-dispersed in hexane or toluene.

Live HeLa cells labeled with cF-UCNPs were photoactivated under a confocal microscope equipped with a 975-nm CW laser diode. The fluorescence signal from fluorescein was recorded in real time. It showed that photo-activation was completed after 90 s of irradiation at 975 nm (FIG. 5). The colocalization of fluorescence from uncaged fluorescein and emissions from ca-NaYbF$_4$:Tm@CaF$_2$ UCNPs supports an in situ photoactivation mechanism (FIG. 16). A comparison of the cell morphology in the transmission microscopy images obtained at pre- and post-NIR laser irradiation showed nothing distinct. Indeed, such low-power NIR lasers have been shown to be harmless on cell samples. A similar live-cell photo-activation was achieved using a two-photon microscope with femtosecond pulsed laser excitation at 975 nm (FIG. 17).

Thus, the invention provides core/shell UCNPs that exhibited highly efficient and Yb$^{3+}$-dependent upconversion UV emission. By optimizing the Yb$^{3+}$ doping level, the UV emission of α-NaYF$_4$:Yb,Tm@CaF$_2$ UCNPs was dramatically improved. The UV emissions of such optimal 27 nm α-NaYF$_4$:Yb,Tm@CaF$_2$ UCNPs are much stronger than those of much larger β-phase counterparts. Furthermore, UV-emitting UCNPs can produce rapid in situ photo-activation in live cells under irradiation with a low power NIR (975 nm) CW laser. These biocompatible UCNPs offer an unprecedented opportunity to serve as UV nano-illuminators for various biomedical applications, such as tracing cell lineages and probing protein dynamics. The more efficient generation of enhanced high-order upconversion photoluminescence developed here provides a new tool for photonics and biophotonics.

UC Photoluminescence Imaging

Photoluminescence (PL) imaging plays an important role in biomedical research as well as in early detection, screening, and image-guided treatment of life-threatening diseases due to PL's rapid imaging process, high sensitivity, robust signal, and low biological toxicity. However, PL applications in deep tissue have been hindered until now due to non-ideal nanoprobes for high-contrast imaging in deep tissue. Ideal optical imaging agents for deep tissue must not only be non-toxic and non-photodamaging, but also have the following properties: (1) light excitation and PL emission capable of penetrating thick tissues, (2) negligible autofluorescence in the detection channel, (3) minimal background light scattering, and (4) efficient luminescence signal. These stringent criteria are mostly associated with the optical characteristics of excitation wavelength, emission wavelength, and their radiation efficiency. While PL imaging has widely used Stokes-shifted contrast agents such as organic fluorophores, semiconductor quantum dots and quantum rods due to their intense brightness, their imaging quality and imaging depth are unsatisfactory due to strong autofluorescence, severe light-scattering background, and low imaging depth induced by ultraviolet or visible light excitation. Although the signal-to-noise ratio (SNR) can be mathematically enhanced by complex spectral unmixing algorithms that isolate the PL signal from background images, the imaging depth cannot be improved. Other factors impeding the biomedical application of current nanoprobes are the photobleaching of organic dyes and the potential toxicity of quantum dots and quantum rods, which contain toxic elements such as selenium and lead. Although nontoxic one-photon optical probes with simultaneous near-infrared light excitation and efficient NIR emission are being investigated, their success remains limited. To remove the strong autofluorescence and light-scattering background generated by ultraviolet or visible light excitation and to improve imaging depth, NIR-to-visible nonlinear nanomaterials, e.g., two-photon-excited quantum rods and gold nanorods, and second harmonic-generation active nanoparticles, have been explored. Although nanoprobes have been developed for cellular imaging with high SNR, they remain unsuccessful for high-contrast in vivo bioimaging because of their low visible luminescent efficiency and the need for an expensive femtosecond laser to provide high excitation density of ~10$^6$-10$^9$ W/cm$^2$. Another challenge to using nonlinear nanoprobes in deep tissue imaging is the large scattering cross-section of photons in the visible range. Tissue is well known to have an NIR "optical transmission window" between 700 and 1000 nm, within which light excitation and emission not only allow deep light penetration and reduce photodamage effects, but also produce low autofluorescence and light scattering. Since endogenous fluorophores in tissue or skin emit via Stokes fluorescence, nanoprobes with anti-Stokes shifted PL have zero autofluorescence in the detection channel. Hence, developing biocompatible efficient anti-Stokes nanoprobes with NIR light excitation and NIR PL within the window of optical transmission is of great interest for high-contrast deep bioimaging.

An attractive alternative to nonlinear two-photon nanomaterials for bioimaging applications is small lanthanide-doped UCNPs. Lanthanide-doped UCNPs have demonstrated high photostability, nonblinking, and low toxicity, making them strong candidates for in vitro and in vivo imaging applications. Despite recent successes in UC PL bioimaging, in vivo imaging with high SNR and deep-tissue penetration has not been conclusively established due to the low efficiency of existing UCNPs. The highest quantum yields (QY) reported to date for upconverting PL are ~1.2% for 85-nm tetragonal LiYF$_4$:Er$^{3+}$ nanocrystals under 1490 nm excitation with a power density of 10-150 W/cm$^2$ and ~0.47% for sub-10-nm hexagonal NaLuF$_4$:Yb$^{3+}$/Er$^{3+}$ nanocrystals excited at 980 nm with a power density of ~18 W/cm$^2$. As the generation of UC PL involves multiphoton processes, the QY of a two-photon UC PL will be linearly related to the excitation density. Therefore, when the excitation density is decreased by an order of ~10$^{-1}$ W/cm$^2$ to implement in vivo optical imaging, the QY of UC PL becomes hundreds of times lower than those reported. Although weak UC PL (even a single photon) can be detected by expensive but highly sensitive electron-multiplied charge-coupled devices (EMCCD), it is preferable to construct efficient NIR$_{in}$-NIR$_{out}$ UC nanocrystals that can be detected by commercial imaging CCDs for high-contrast deep bioimaging.

High-contrast in vitro and in vivo bioimaging has been reported using NIR$_{in}$-NIR$_{out}$ UC NaYF$_4$:Yb,Tm nanocrystals where excitation at ~980 nm and the PL peak at 800 nm are both within the NIR optical transmission window of biological tissues. Since that report, NIR$_{in}$-NIR$_{out}$ UCNPs have been suggested as promising bioimaging probes with low background and deep tissue penetration, but their low efficiency, even with EMCCD detection, is still a formidable hindrance to improving SNR and imaging depth. To improve the QY or efficiency of existing UCNPs, various methods are being explored. Likewise, a novel strategy was developed that not only enhances the quantum yield of NIR UC PL 8 times, but also increases the extinction of every nanoparticle 5 times by elevating the Yb$^{3+}$ sensitizer concentration.

It is shown here that the PL of previously designed NIR$_{in}$-NIR$_{out}$ α-NaYbF$_4$:Tm UCNPs is enhanced 35 times by encapsulating them in a hetero-shell of CaF$_2$ that efficiently suppresses surface quenching, yielding a QY as high as 0.6% under low-energy excitation of ~0.3 W/cm$^2$. CaF$_2$ was chosen as the epitaxial shell material due to its low lattice mismatch with α-NaYbF$_4$, its good optical transparence, high crystallizability and stability. Furthermore, the CaF$_2$ shell enhances the biocompatibility of UCNPs, as CaF$_2$ is a common endogenous component of bone and teeth. Using this efficient NIR$_{in}$-NIR$_{out}$ core/shell NaYbF$_4$: Tm@CaF$_2$ nanoparticle, it is shown that whole-body imaging of a BALB/c mouse with a commercially available CCD camera can easily reach a SNR of 310, and that UC PL can be detected with low light-scattering background from a synthetic scaffold wrapped around a rat femur or through a 3.2-cm thick pork tissue.

Figure 7:
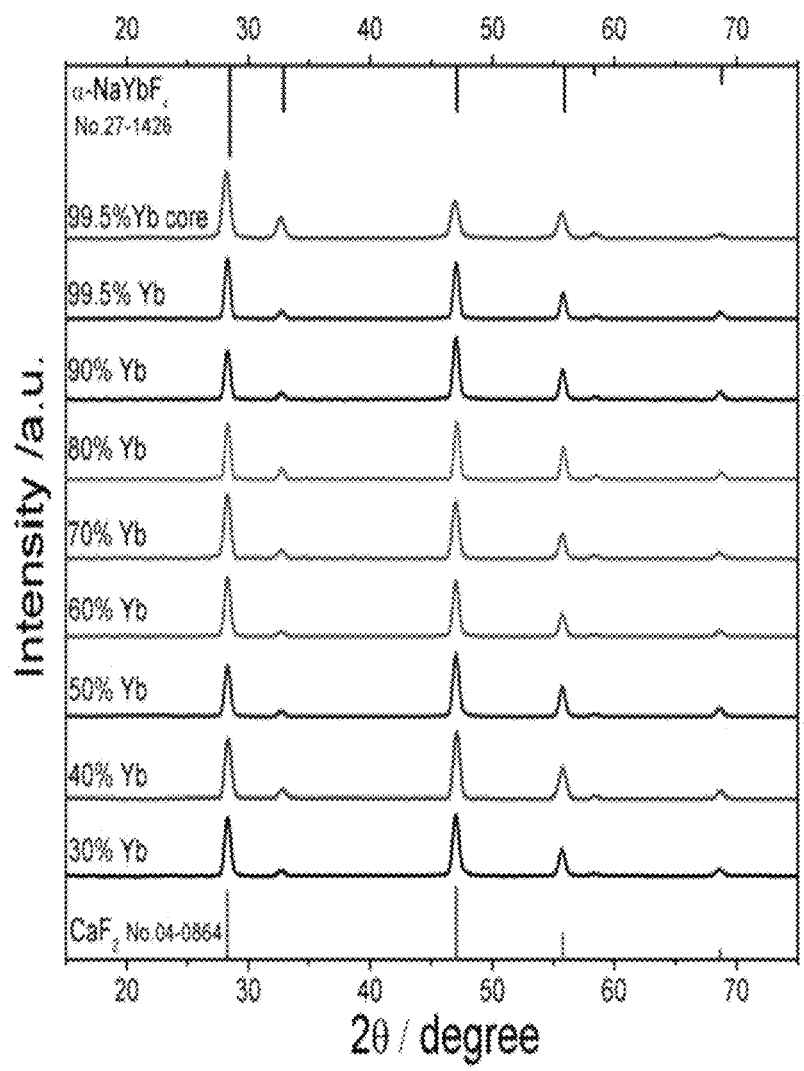
FIG. 7 shows exemplary X-ray diffraction (XRD) patterns of α-NaYbF$_4$:Tm core and α-NaYF$_4$:Yb,Er@CaF$_2$ core/shell UCNPs with different $Yb^{3+}$ doping levels.
Figures 8A, 8B:
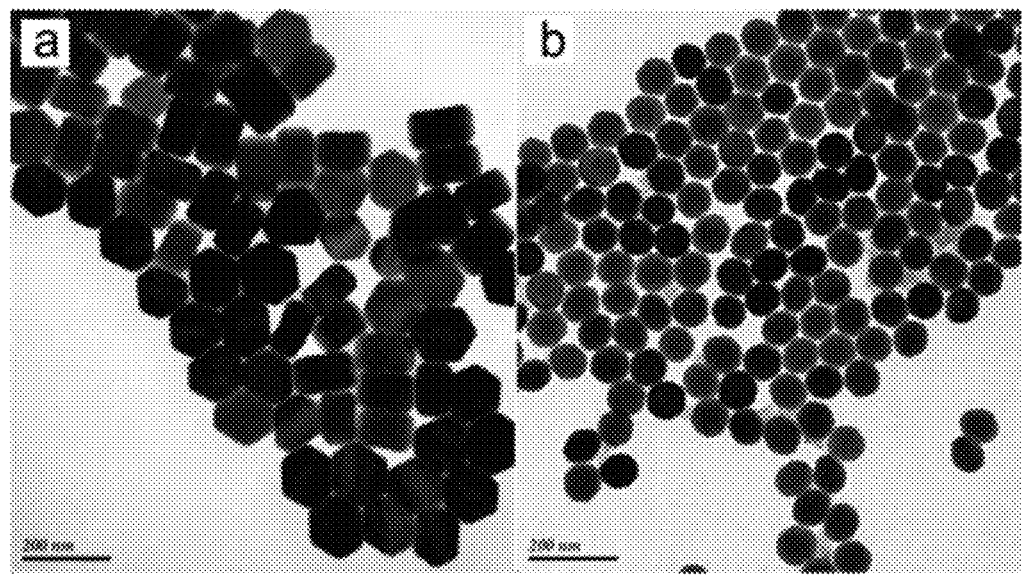
FIG. 8(a)-FIG. 8(c) show exemplary TEM images of β-NaYF$_4$:30% Yb, 0.5% Tm FIG. 8(a) and β-NaYbF$_4$:0.5% Tm FIG. 8(b) UCNPs.
Figure 8C:
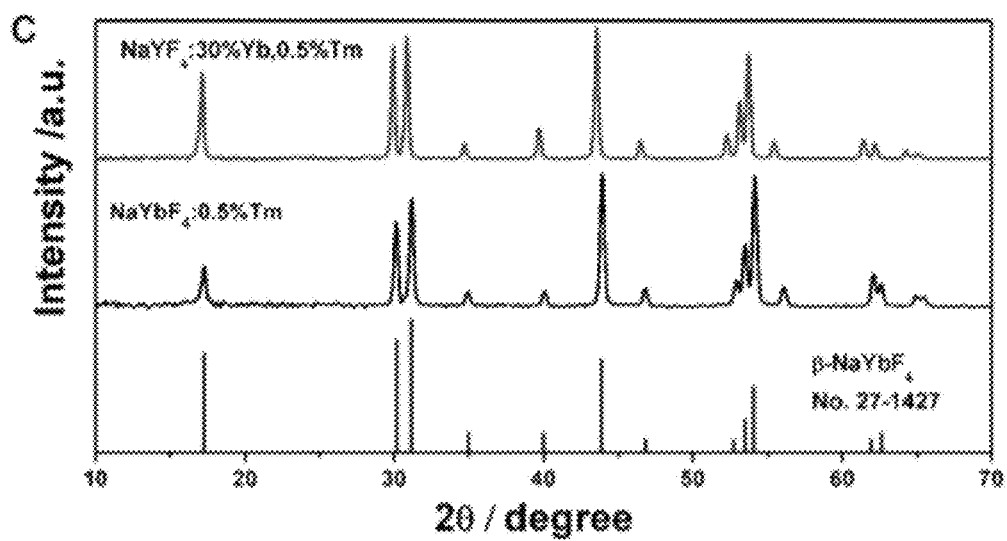
Figure 9A:
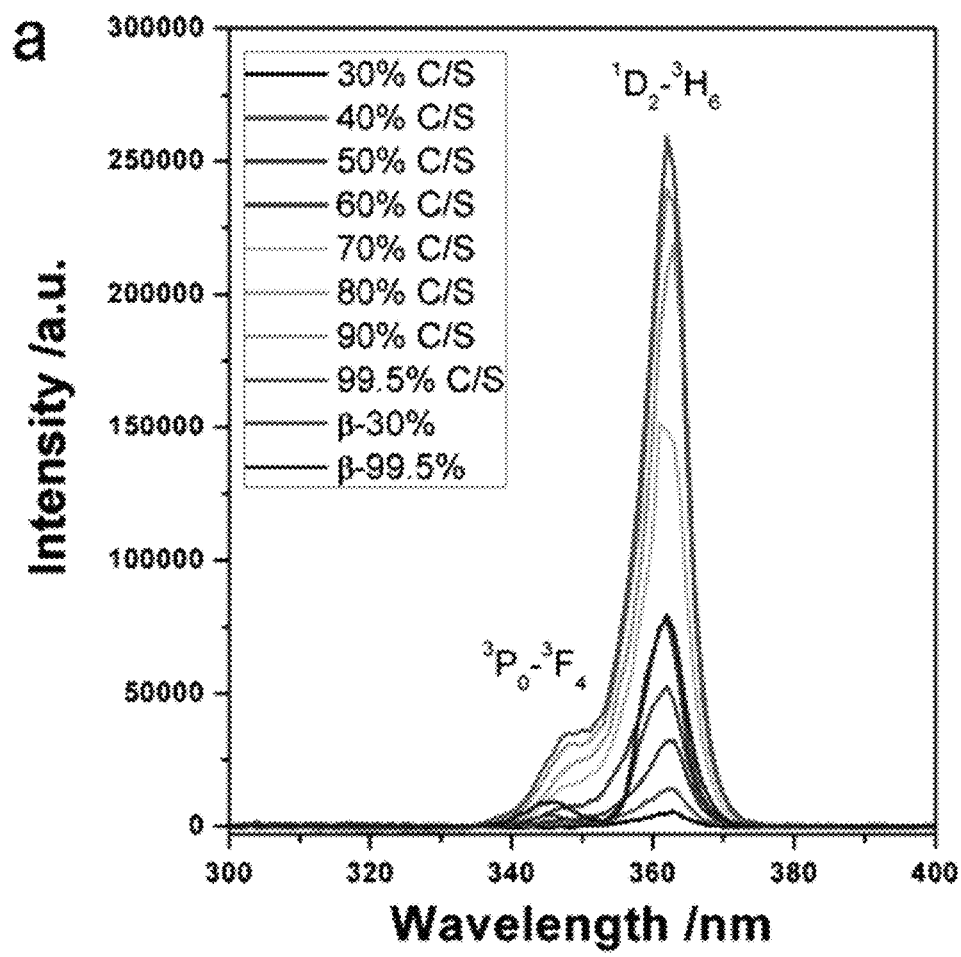
FIG. 9(a)-FIG. 9(f) show exemplary upconverting emission spectra and corresponding integral counts of α-NaYF$_4$:Yb,Tm@CaF$_2$, β-NaYF$_4$:30% Yb, 0.5% Tm, and β-NaYbF$_4$:0.59% Tm UCNPs, measured under 2.6 W/cm$^2$ of 975-nm excitation with a normalized $Ln^{3+}$ concentration.
Figure 9B:
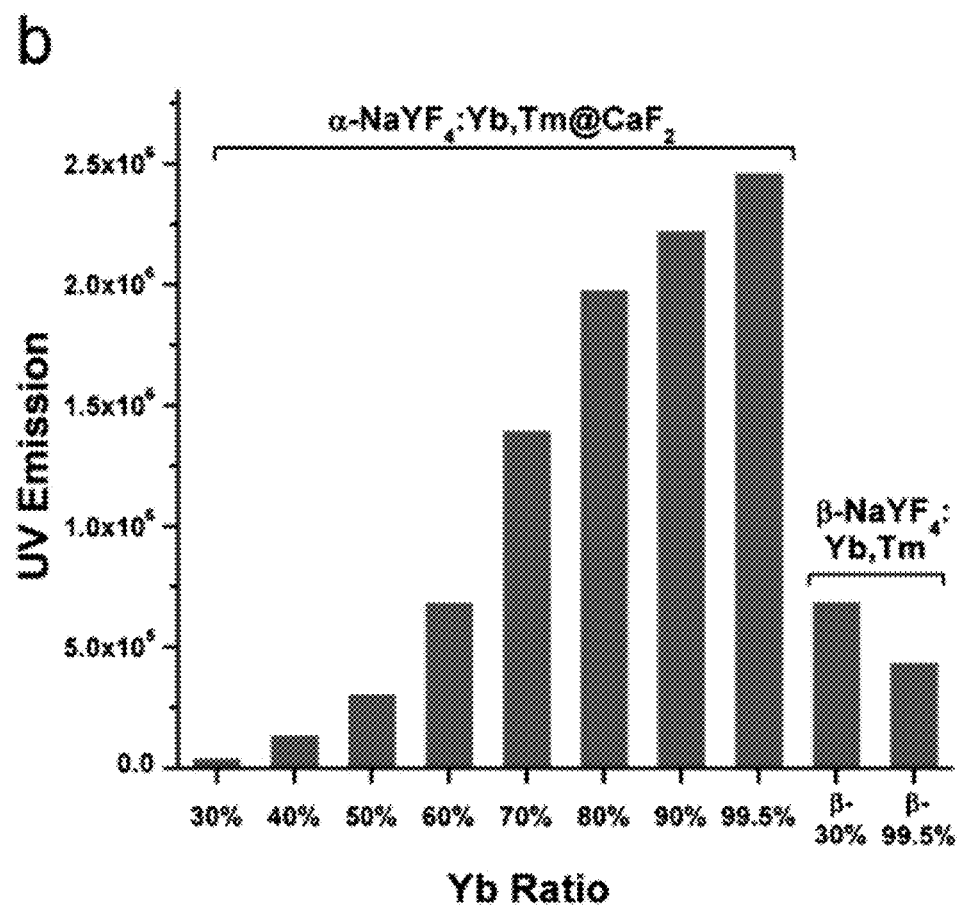
Figure 9C:
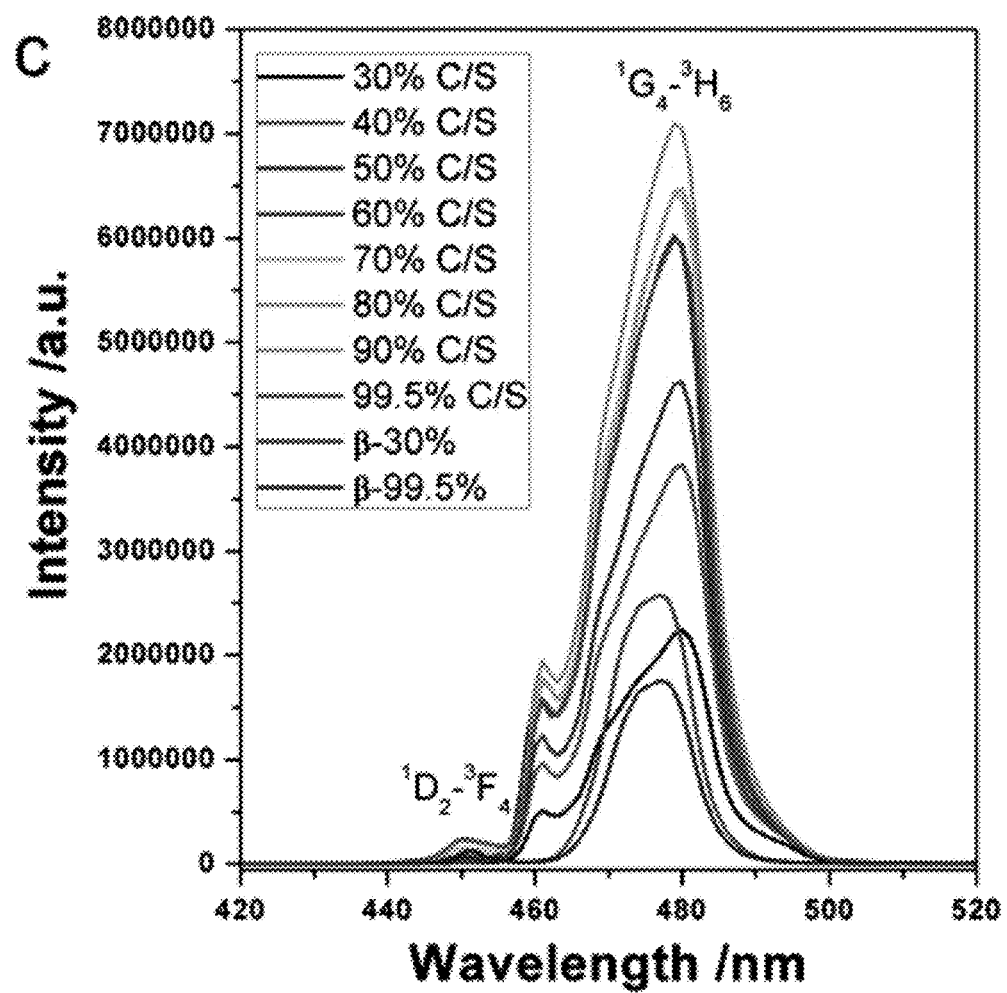
Figure 9D:
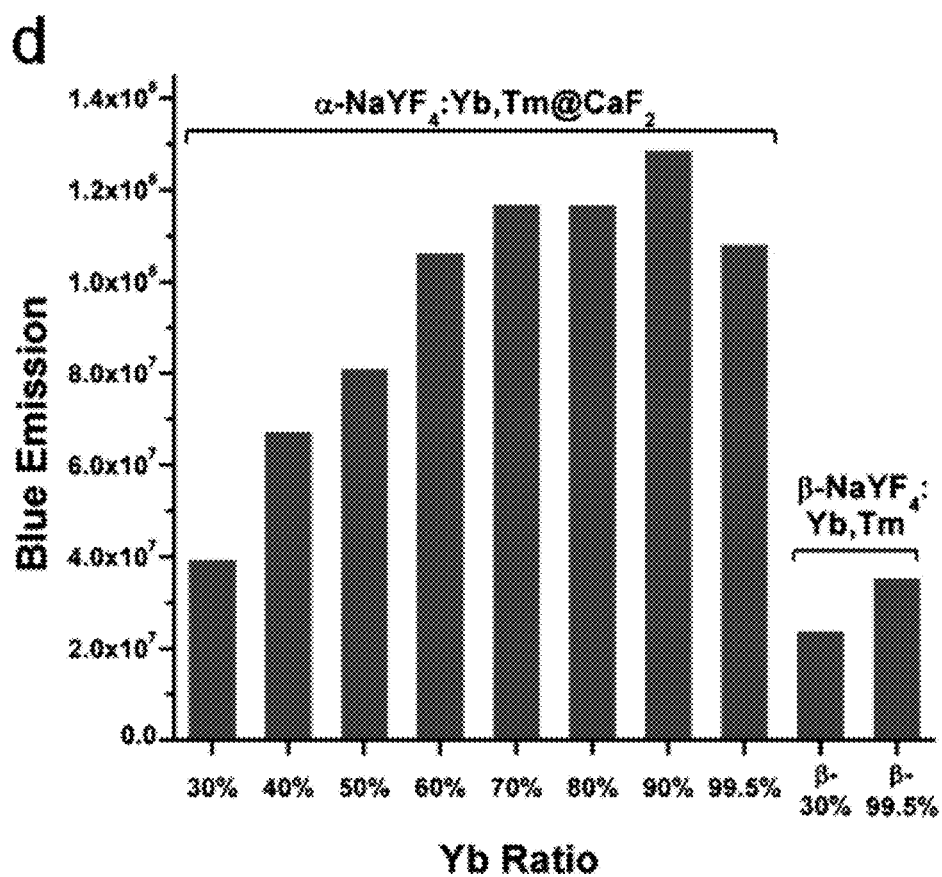
Figure 9E:
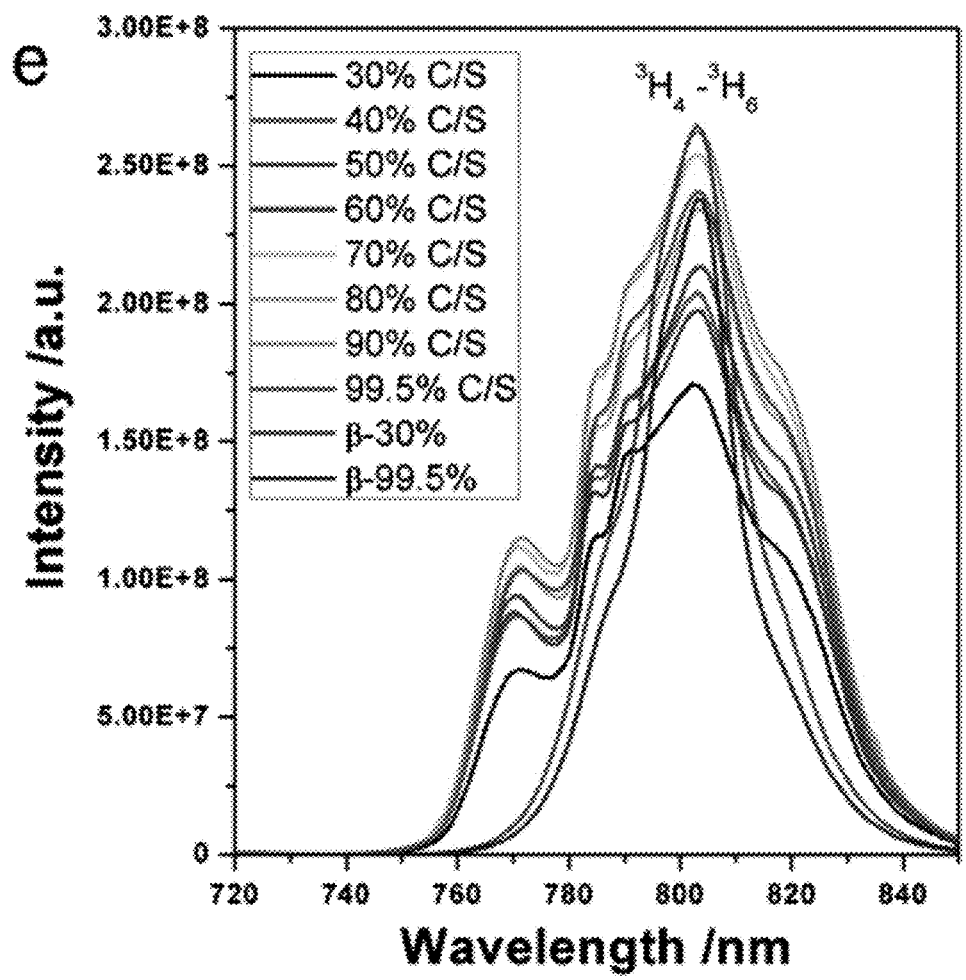
Figure 9F:
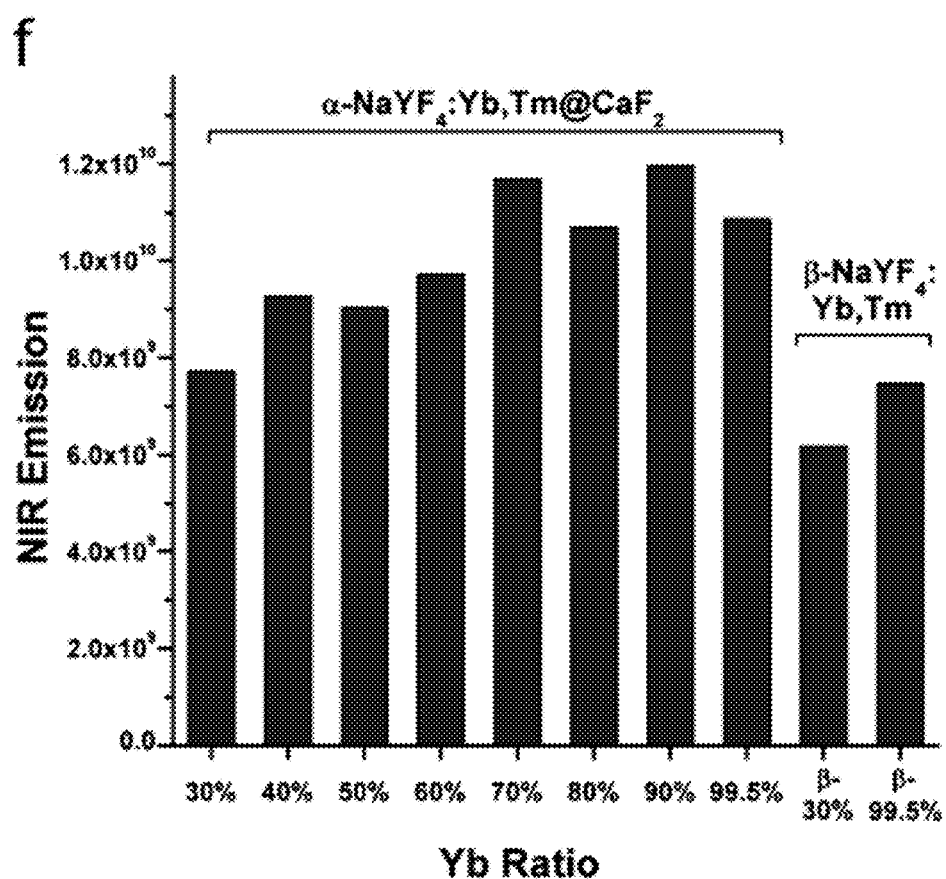

The synthesized NaYbF$_4$: 0.5% Tm core nanoparticles are monodisperse nanopolyhedras with an average diameter of about 20 nm (FIG. 2a). The resulting NaYbF$_4$: 0.5% Tm@CaF$_2$ core/shell nanoparticles are monodisperse nanocubes, with an average size of about 27.1 nm after growing a CaF$_2$ shell (FIG. 2b). The powder x-ray diffraction peaks of the NaYbF$_4$:0.5% Tm$^{3+}$ core and NaYbF$_4$:0.5% Tm@CaF$_2$ core/shell UCNPs in FIG. 7 has the identical positions at the standard JCPDS 06-0258 cubic NaYbF$_4$ (α-NaYbF$_4$) or JCPDS 77-2095 cubic CaF$_2$ structures. In addition, the relative intensity of the peak at 47° to that at 28° in core/shell nanoparticles is apparently higher than that of core nanoparticles, corresponding to the difference between the standard JCPDS 06-0258 α-NaYbF$_4$ and JCPDS 77-2095 CaF$_2$ structures. These results indicate successful epitaxial growth of CaF$_2$ shells on the α-NaYbF$_4$: 0.5% Tm core nanoparticles.

Figure 21A:
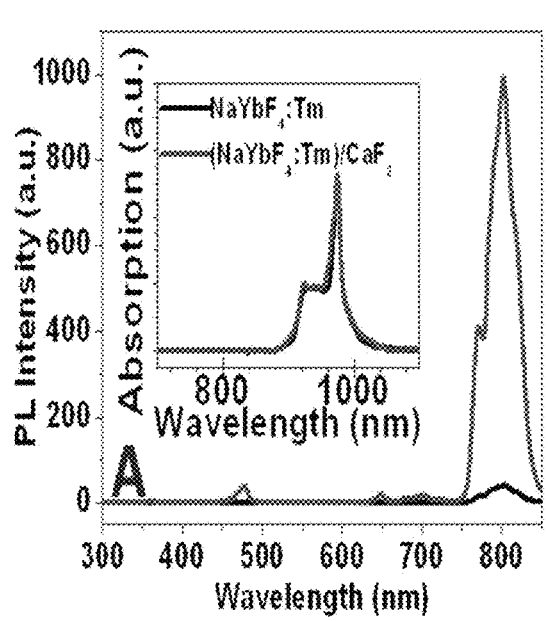
FIG. 21(a)-FIG. 21(d) show exemplary optical characterizations of $NaYbF_4$:0.5% Tm@$CaF_2$ core/shell UCNPs.
Figure 21B:
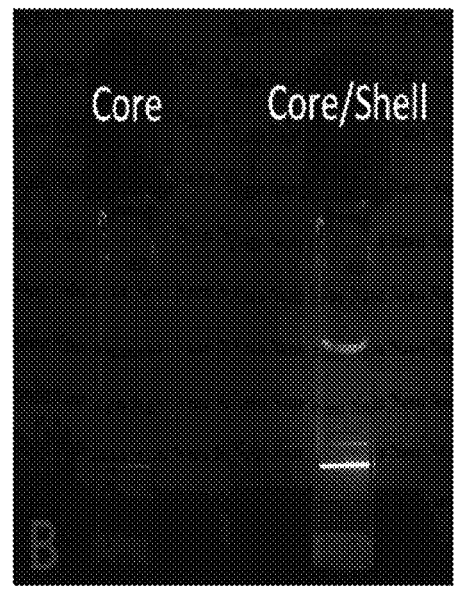
Figure 21C:
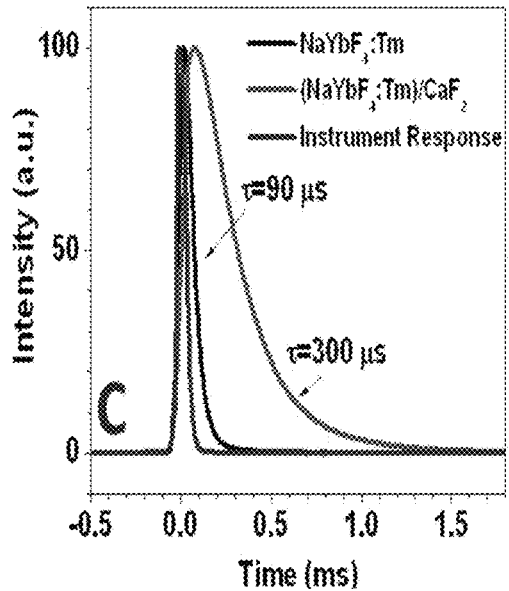
Figure 21D:
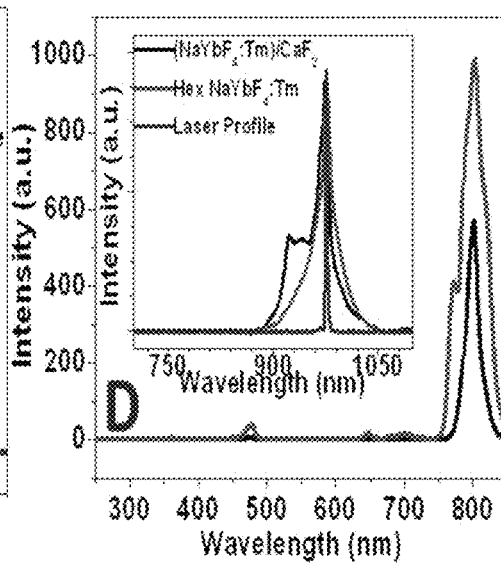

UC PL spectra of α-NaYbF$_4$: 0.5% Tm core and α-NaYbF$_4$:0.5% Tm@CaF$_2$ core/shell nanoparticles diluted in hexane were compared and displayed in FIG. 21a. Their absorption spectra are normalized to 975 nm for the $^2F_{7/2} \rightarrow {^2F_{5/2}}$ transition of Yb$^{3+}$ ions by adjusting the concentrations (see FIG. 21a inset). Four UC PL bands are clearly resolved; they have maxima at 476, 650, 700, and 802 nm, corresponding to $^1G_4 \rightarrow {^3H_6}$, $^1G_4 \rightarrow {^3F_4}$, $^3F_{2,3} \rightarrow {^3H_6}$ and $^3H_4 \rightarrow {^3H_6}$ transitions of Tm$^{3+}$ ions, respectively. The NIR UC PL peak at 802 nm represents a two-photon process, whose intensity is much more intense than that of the other UC PL peaks, favoring bioimaging applications. The intensity of NIR UC PL in core/shell nanoparticles is about 35 times higher than that of core nanoparticles. This difference in intensity is also illustrated in photographic images of UC PL from core and core/shell nanoparticles (FIG. 21b) where the visible blue emission at 476 nm in core/shell nanoparticles is much higher than that of core nanoparticles. Since pure CaF$_2$ shell nanoparticles do not exhibit UC PL, the higher intensity undoubtedly originates from the effect of the shell on the core α-NaYbF$_4$:Tm 0.5% nanocrystals. This enhancement likely arises from suppressing surface quenching due to decreased surface defects and alleviating ligand influence by the shell layer. To verify this assumption, the UC PL decays of core and core/shell nanoparticles at 805 nm were measured (FIG. 21c). The average lifetime of core/shell nanoparticles is 300 μs, significantly longer than the 90 μs lifetime of core nanoparticles, demonstrating that the significant enhancement of UC PL arises from efficient suppression of the surface-quenching effect. Larger nanoparticles with hexagonal structure are generally known to have high efficiency; for example, visible UC PL in β-NaYF$_4$:Yb,Er material is 4.4 times higher than that of α-NaYF$_4$:Yb,Er material, and the QY of 100-nm β-NaYF$_4$: Yb$^{3+}$/Er$^{3+}$ nanoparticles is 3 times higher than that of 30-nm β-NaYF$_4$:Yb,Er nanoparticles. Comparison of the emission spectra of small core/shell nanoparticles with those of larger β-NaYbF$_4$:0.5% Tm nanoparticles (FIG. 21d) shows that the integrated NIR UC PL intensity of 27-nm α-NaYbF$_4$:0.5% Tm@CaF$_2$ core/shell nanoparticles is about 2 times higher than that of 100-nm β-NaYbF$_4$:0.5% Tm$^{3+}$ nanoparticles, demonstrating their high efficiency. The quantum yield of NIR UC PL in 27-nm α-NaYbF$_4$: 0.5% Tm@CaF$_2$ core/shell nanoparticles was 0.60% under extremely low-energy excitation of 0.3 W/cm$^2$, using IR 26 as a standard reference (Examples). This quantum yield is the highest value to date for colloidal UCNPs under 975-nm excitation.

Figures 22A, 22B:
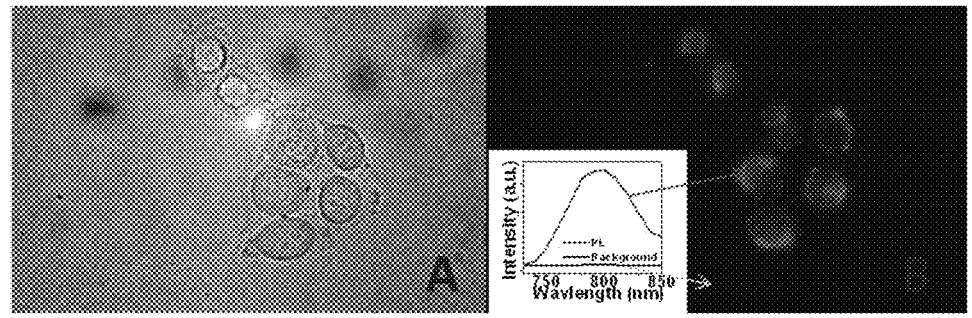
FIG. 22(a)-FIG. 22(b) show exemplary in vitro transmission (left) and PL (right) images of HeLa cells treated with α-$NaYbF_4$: 0.5% Tm@$CaF_2$ core/shell UCNPs coated with hyaluronic acid (HA).
Figures 23A, 23B, 23C:
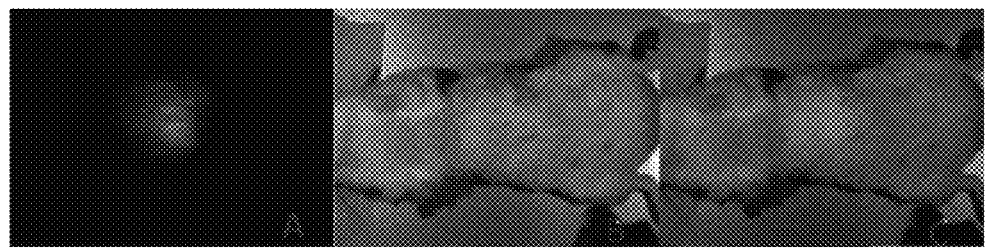
FIG. 23(a)-FIG. 23(f) show exemplary whole-animal NIR image of a mouse injected via tail vein with HA-coated α-$NaYbF_4$: 0.5% Tm@$CaF_2$ core/shell UCNPs.
Figures 23D, 23E:
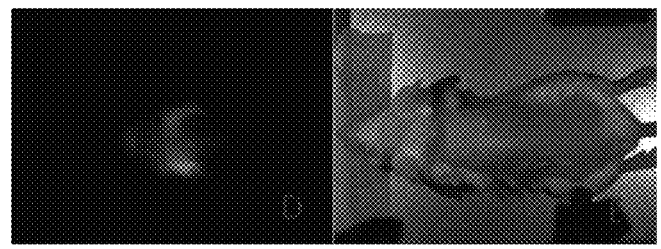
Figure 23F:
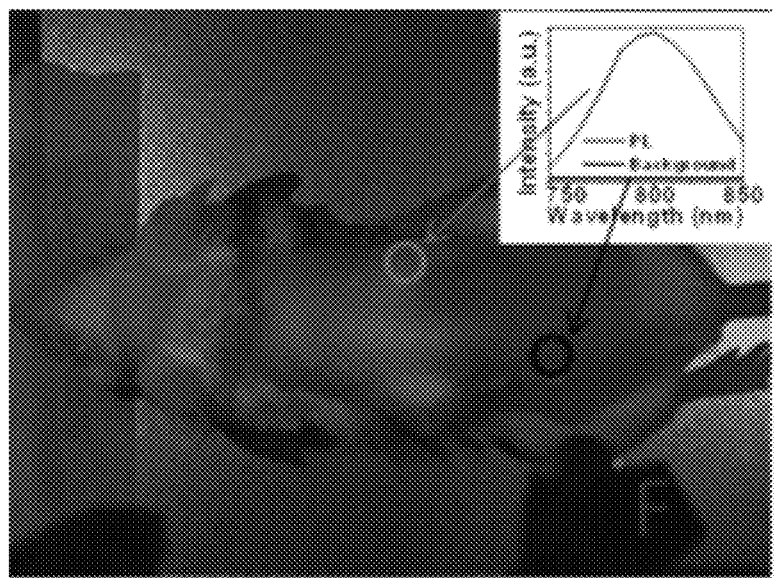

To determine the cellular imaging feasibility of $NIR_{in}$-$NIR_{out}$ α-NaYbF$_4$: 0.5% Tm@CaF$_2$ core/shell nanoparticles, they were coated with hyaluronic acid (HA, an anionic, nonsulfated glycosaminoglycan) and incubated the HA-coated nanoparticles with HeLa cells to allow particle endocytosis. Cells were imaged using a Nikon Eclipse TE 2000 microscope equipped with a Nuance CCD camera (Cambridge Research & Instrumentation Inc., CRi) capable of imaging within 500- to 950-nm. The light source was a fiber-coupled laser diode emitting at 980 nm, with the fiber introduced through the entrance port of the microscope. FIG. 22 shows the transmission and PL images of HeLa cells treated with UCNPs after excitation at 980 nm. The localized emission spectrum from the cells shows a characteristic PL Tm$^{3+}$ peak at ~800 nm (FIG. 22, right, inset). Complete absence of autofluorescence supports that UCNPs are uniquely suited for in vitro high-contrast PL imaging in cultured cells.

Figure 19:
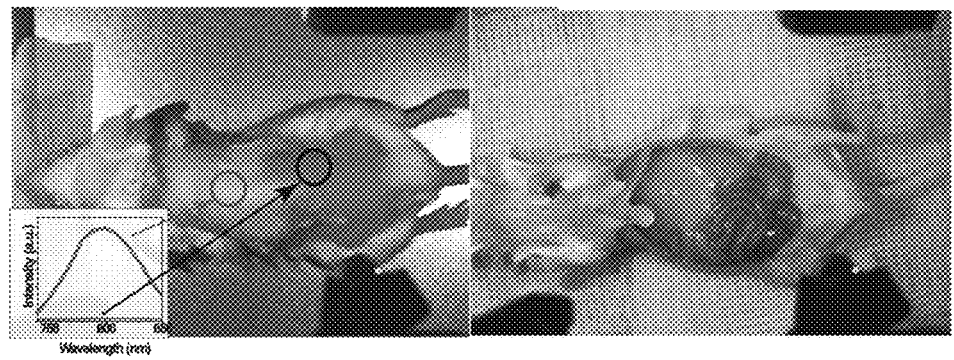
FIG. 19 shows exemplary whole-animal NIR image of a mouse injected via its tail vein with hyaluronic acid-coated UCNPs. (Left) Intact Mouse. (Right) Mouse with exposed thorax.
Figure 20A:
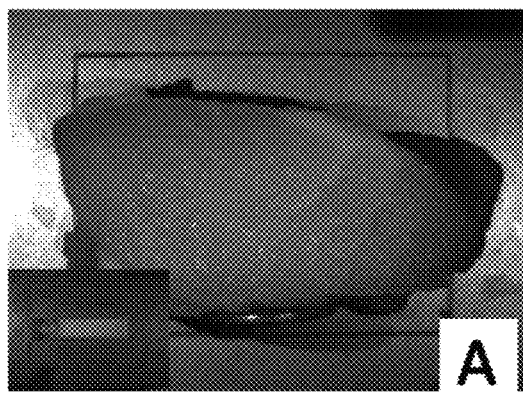
FIG. 20(a)-FIG. 20(d) show exemplary images of cuvette prefilled with core/shell UCNPs without FIG. 20(a) and with FIG. 20(c) thick pork covering, FIG. 20(b) top image and FIG. 20(d) dissection image of thick pork. The inset in FIG. 20(c) is the spectra of upconverting signals and background taken from the circled areas.
Figure 20B:
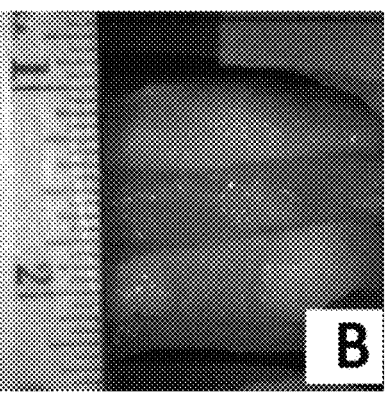
Figure 20C:
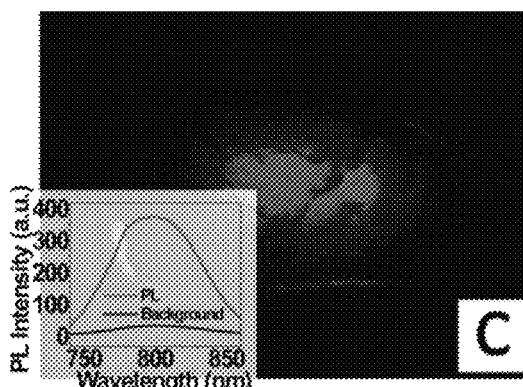
Figure 20D:
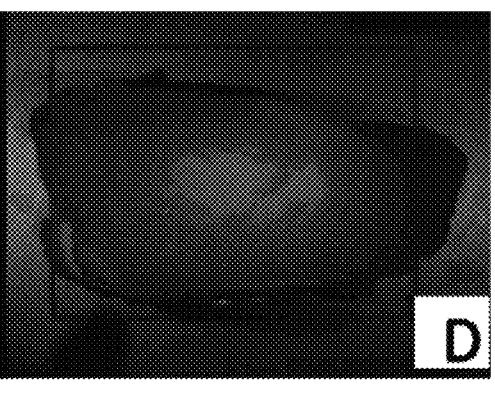

To examine the suitability of α-NaYbF$_4$: 0.5% Tm@CaF$_2$ core/shell nanoparticles for in vivo imaging, BALB/c mice were intravenously injected (via tail vein) with HA-coated core/shell nanoparticles (700 pmol/kg). The mice were imaged for in vivo PL at 3 h post-injection using the Maestro fluorescence imaging system (CRi). The core/shell nanoparticles were excited at 980 nm by defocused emission from the fiber-coupled laser diode introduced into the imaging chamber. Excitation light was blocked by an emission filter (850 SP) before the imaging CCD camera (Sony icx285, working range: 500- to 950-nm). High-contrast images of a mouse injected with the core/shell nanoparticles (FIG. 19) clearly show that it is feasible to image and spectrally distinguish their characteristic emissions using the Maestro imaging software. A scan from 700- to 950-nm showed an intense NIR luminescence peak at ~800 nm (shown in red in FIG. 19). The signal was readily detectable through the skin of shaved and unshaven mice. The SNR, defined by the ratio of the integrated PL intensity in the area of interest (red circle) to that in the same area of surrounding tissues (black circle), is 310, about 10-fold greater than that reported for in vivo imaging by UCNPs. The high contrast between the background and PL signal of UCNPs results from efficient NIR to NIR UC PL. The background noise arises mostly from the noise inherent in the CCD camera employed; it is expected a significant increase in SNR when using highly sensitive EMCCD. Another important point to mention is that the mice injected with HA-coated core/shell nanoparticles remained healthy at 270 days post-injection.

Figure 24A:
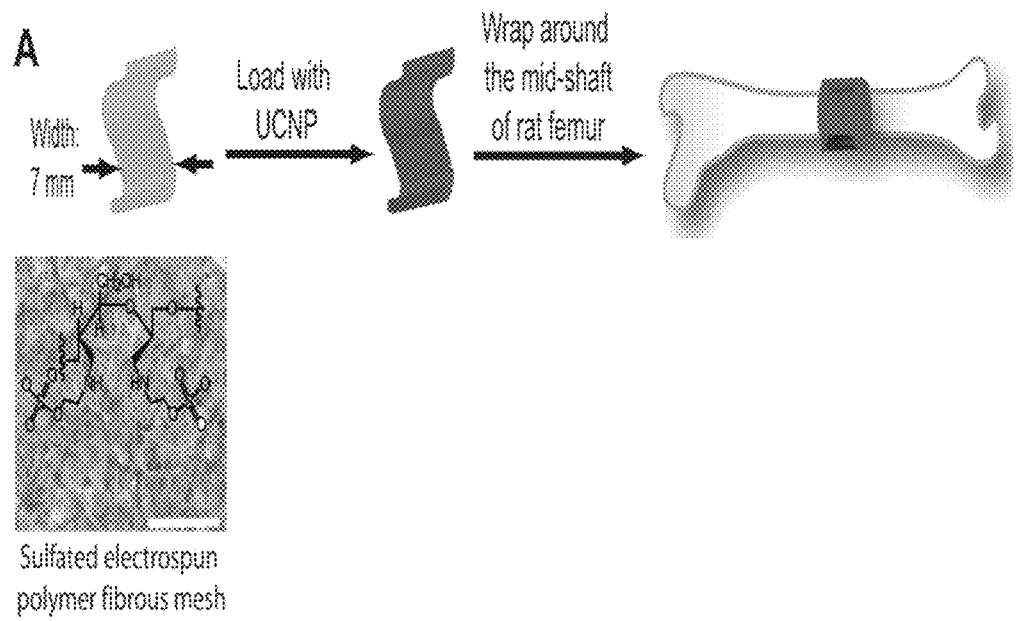
FIG. 24(a)-FIG. 24(b) show FIG. 24(a) UCNPs were loaded on a 7-mm sulfated polymer mesh and wrapped around a rat femur. Scale bar: 500 m.
Figure 24B:
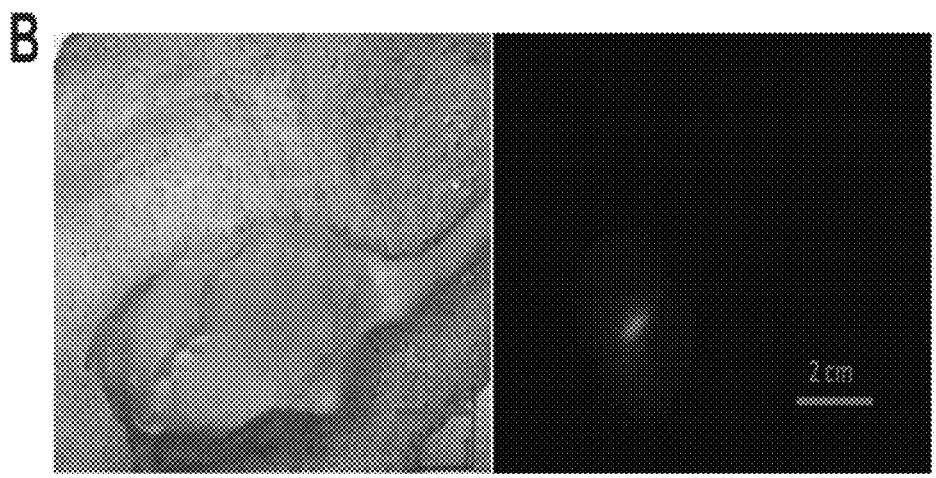

To examine the tissue penetration depth and possibility for local retention of α-NaYbF$_4$: 0.5% Tm@CaF$_2$ core/shell nanoparticles on synthetic scaffolds for tissue-engineering applications, polyethyleneimine-coated $NIR_{in}$-$NIR_{out}$ α-NaYbF$_4$:0.5% Tm@CaF$_2$ core/shell nanoparticles were absorbed on a sulfated polymeric fibrous mesh and wrapped it around rat femur for imaging. The sulfated mesh was chemically modified from thermal-mechanically annealed electrospun cellulose acetate fibrous mesh. The sulfated mesh (7 mm×10 mm×0.1 mm) was loaded with 4-g core/shell particles (400 μL of 10 μg/mL aqueous suspension) by repeated loading/drying (vacuum oven at room temperature). To implant the UCNP-loaded mesh, the hind leg of a freshly sacrificed adult male Sprague-Dawley rat (441 g) was shaved and its femur was exposed by a combination of sharp and blunt dissections. The periosteal tissue attached to the exposed femur was removed by a bone elevator, and the UCNP-loaded mesh was circumferentially wrapped around the exposed femur, the outer diameter of which was 4 mm. The muscle and skin was then suture-closed in layers (3.0 chromic gut suture). The thickness of the operated hind leg, including the femur and surrounding muscle and skin, was approximately 16 mm. Seven days after the UCNP-loaded mesh was implanted, the operated hind leg was imaged (FIG. 24). The UCNP-loaded mesh can be readily visualized around the femur with minimal background detected in the surrounding tissue, indicating that the positively charged UCNPs were stably retained on the sulfated mesh with their upconverting properties intact in the in vivo tissue environment. The intense emissions detected from the UCNP-loaded mesh embedded almost 1 centimeter deep and the minimal surrounding-tissue background confirms that these UCNPs are promising candidates for tissue engineering applications.

Finally, to explore the possibility of detecting UC PL at an even deeper tissue depth, a 1.25-inch (3.2-cm) slice of pork was placed between the laser source and a cuvette (1 cm×5 cm×0.5 cm) prefilled with α-NaYbF$_4$:0.5% Tm@CaF$_2$ UCNPs (225 nM). The NIR upconverted emissions can still be clearly detected from the light-scattering background with a SNR of about 3 (FIG. 20). This tissue-penetration depth exhibited by the $NIR_{in}$-$NIR_{out}$ UCNPs should satisfy the needs of both small and large animal in vivo imaging.

In Situ Real-Time Recorded Biocompatible Photoactivation

Figure 27:
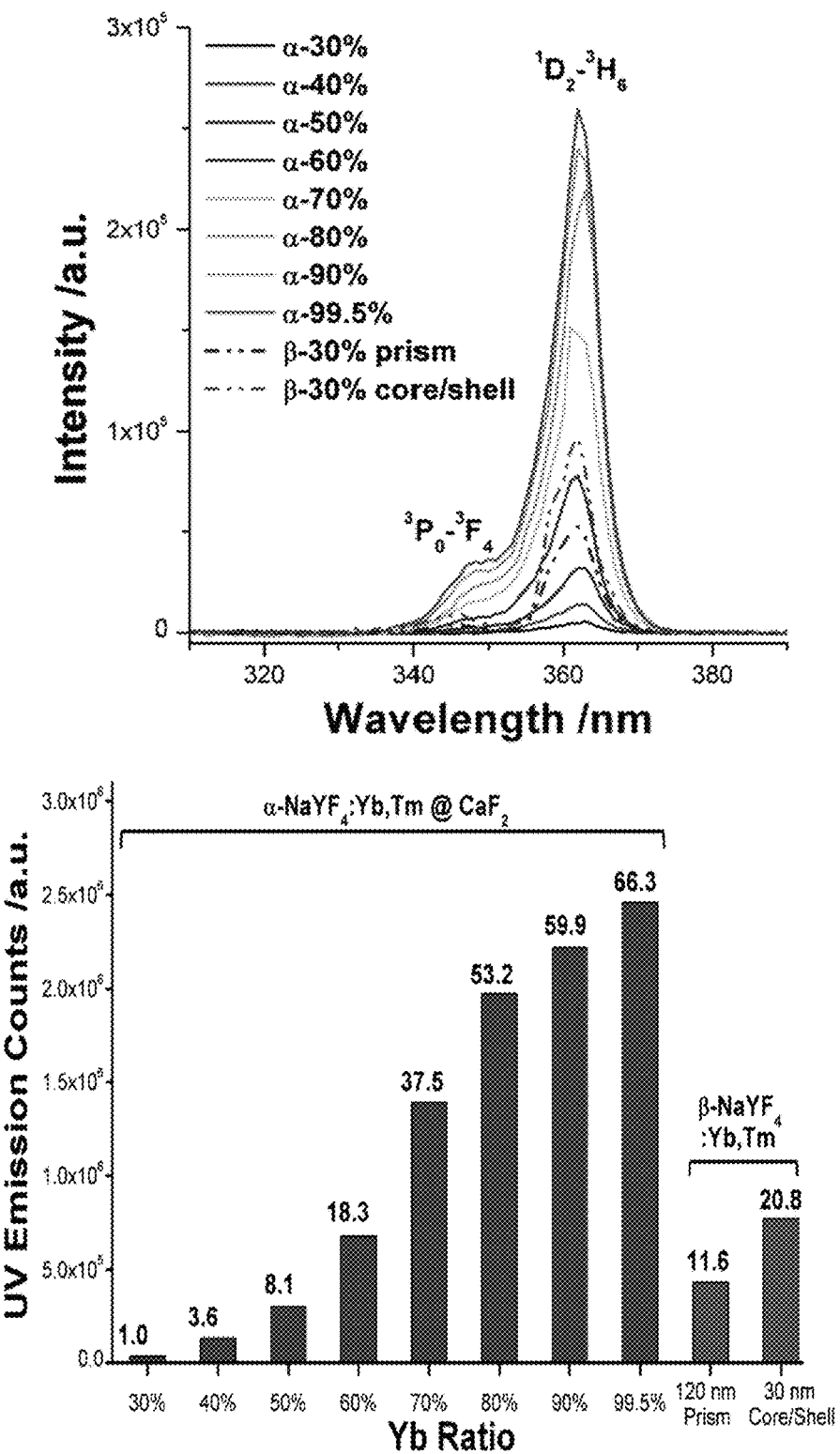
FIG. 27 shows exemplary upconverting emission spectra and corresponding integral counts of α-$NaYF_4$:Yb,Tm/$CaF_2$, 120 nm β-$NaYF_4$:30% Yb, 0.5% Tm prism, and β-$NaYF_4$:30% Yb, 0.5% Tm/β-$NaYF_4$ UCNPs, measured under 2.6 W·cm$^{-2}$ of 975-nm excitation with a normalized Tm$^{3+}$ concentration.
Figure 27:
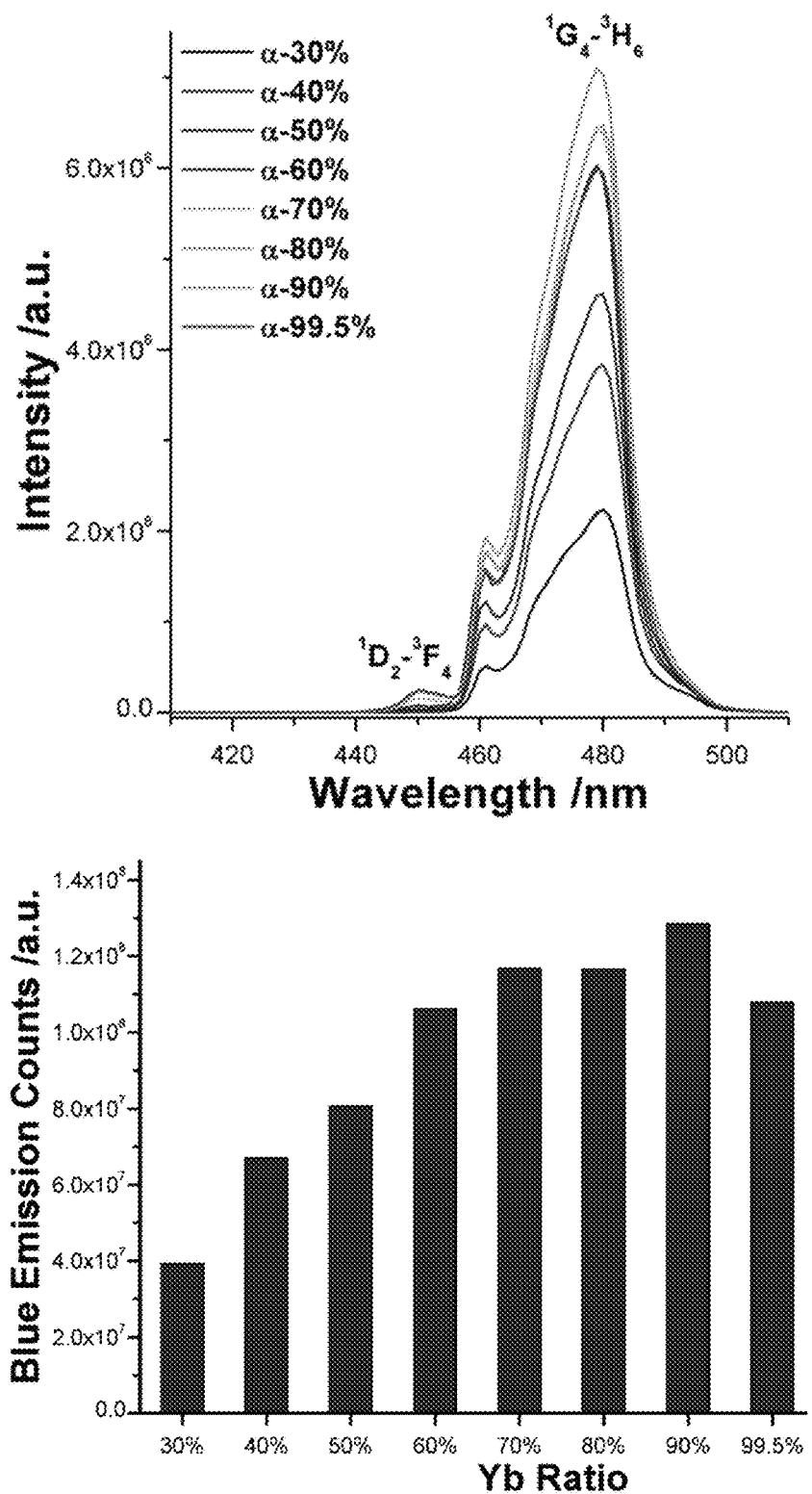
Figure 27:
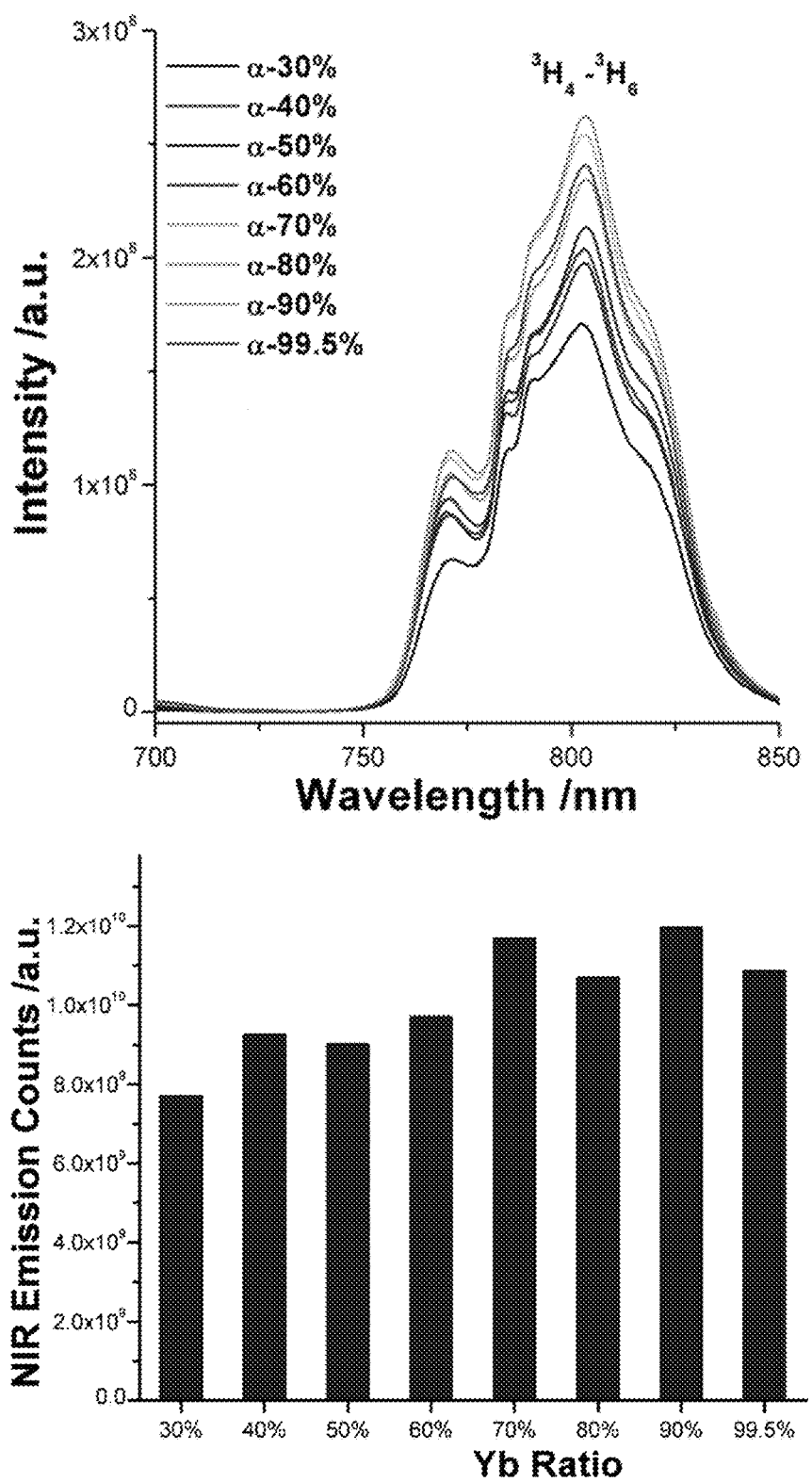
Figure 28:
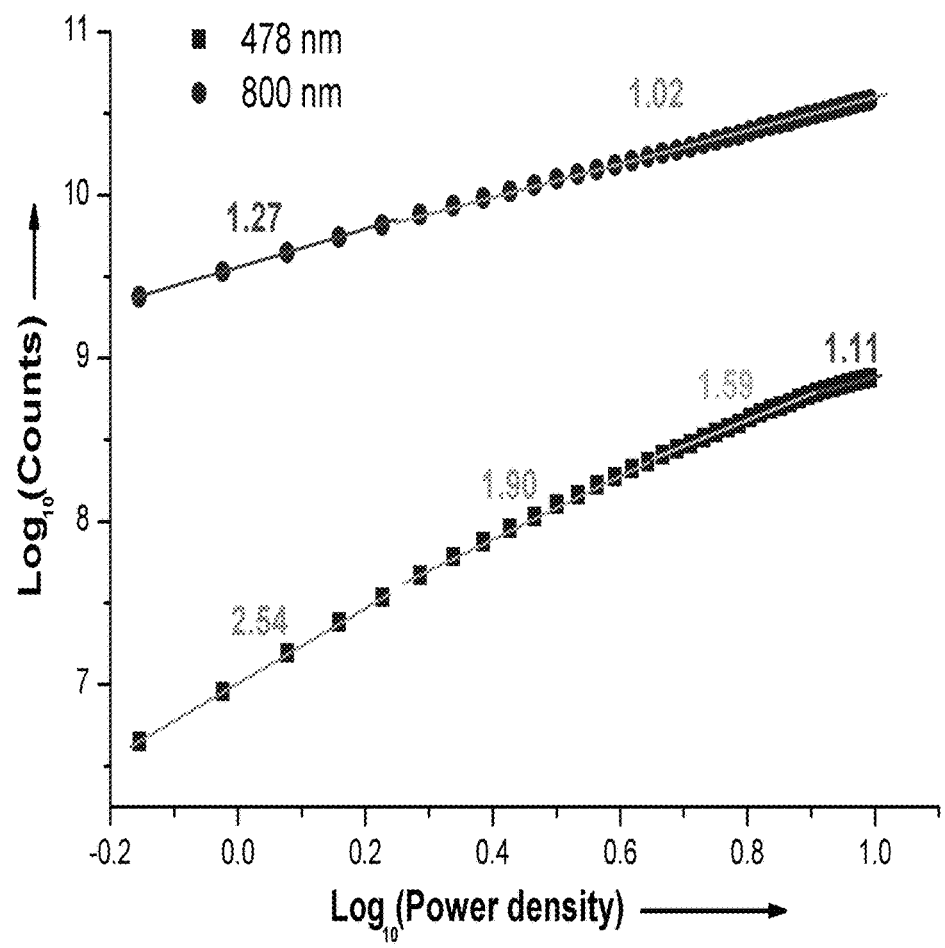
FIG. 28 shows exemplary emission power dependence measurement of α-$NaYbF_4$:Tm/$CaF_2$ UCNPs. With high efficiency Yb$^{3+}$ sensitizing in α-$NaYbF_4$:Tm/$CaF_2$, the blue (478 nm) and NIR (800 nm) emitting levels of Tm$^{3+}$ showed evident energy saturations even under 2.6 W·cm$^{-2}$ of excitation power.

The UV output in core/shell nanoparticles can be systematically tuned and increased monotonically with the increase of Yb$^{3+}$ doping without energy saturation via the increase of Yb$^{3+}$ doping up to 99.5% Yb doping ratio under 2.6 W/cm$^2$ (the lowest power density reported for UCNP-mediated photochemistry). However, the tunability in blue and NIR is much poorer, i.e. energy saturation of the blue and NIR are both obvious under the same power density, thus the increase in blue and NIR emission with elevated Yb$^{3+}$ ratios is significantly smaller than that of UV emission, approaching the maximum of about 70% of Yb$^{3+}$. (FIGS. 27 and 28). Optimization of the four-photon UV upconverting emission in this core/shell system leads the maximum quantum yield to be 0.1%, and over 9 times brighter than the known optimal β-NaYF4:30% Yb, 0.5% Tm/β-NaYF4 core/shell UCNPs in aqueous phase after ligand exchange. Due to the significantly enhanced NIR-UV efficiency, such UCNPs were used as dual imaging/photoactivation probes and reported a real-time recording of UCNP-mediated rapid photoactivation down to just a few cells.

The design disclosed herein led to a maximum 9-fold enhancement in comparison with known optimal β-phase core/shell UCNPs in water. A highly effective and rapid in situ real-time live-cell photoactivation was recorded for the first time with such nanoparticles.

In one aspect, the invention generally relates to a novel biocompatible upconversion cubic nanoparticle comprising: a core of cubic nanocrystals comprising α-Na Ln$_{(a)}$ Ln$_{(b)}$ Ln$_{(c)}$ F$_4$; and an epitaxial shell formed from CaF$_2$, wherein Ln$_{(b)}$ is Yb.

Preferably the molar ratio of Ln$_{(c)}$/(Ln$_{(a)}$+Ln$_{(b)}$+Ln$_{(c)}$) in the nanoparticle is a about 0.5±0.02%.

Preferably the molar ratio of Ln$_{(b)}$/(Ln$_{(a)}$+Ln$_{(b)}$+Ln$_{(c)}$) in the nanoparticle is greater than 30%. More preferably the ratio is greater than about greater than about 70%. Even more preferably, the ratio is greater than about 90%. Most preferably, the ratio is about 99.5%.

Ln$_{(a)}$ of NaLn$_{(a)}$F$_4$ may be a lanthanide selected from the group consisting of yttrium (Y) and gadolinium (Gd), scandium (Sc) and luthanium (Lu). Preferably, Ln(a) is yttrium (Y).

$Ln_{(c)}$ of $NaLn_{(c)}F_4$ can be a lanthanide selected from the group consisting of erbium (Er), holmium (Ho), and thulium (Tm). Preferably, $Ln_{(c)}$ is thulium (Tm).

Preferably, each side of the cubic nanoparticle has an average length of about 27±20 nm. More preferably, the nanoparticle has an average length of about 27±10 nm (e.g., the nanoparticle has an average length of about 27±2 nm).

The nanoparticle may have a core of greater than about 98% of cubic nanocrystals. Preferably, the core of the naonparticle comprises greater than about 99% of cubic nanocrystals. More preferably, the core of the nanoparticle comprises greater than about 99.5% of cubic nanocrystals.

The invention also provides for a plurality of nanoparticles, wherein about 98% of the nanoparticles are cubic nanoparticles with an average length of each side of the nanoparticle of about 27±20 nm. Preferably, at least 99% are cubic nanoparticles of with each side of the nanoparticle having an average length of about 27±10 nm. More preferably at least 99.5% of the nanoparticles are cubic nano particles wherein each side of the nanoparticle has an average length of about 27±2 nm.

In another aspect, the invention generally relates to a novel biocompatible UCNP comprising: a core of cubic nanocrystals comprising α-Na (Y, Yb, Tm)F₄; an epitaxial shell formed from CaF₂, wherein the molar ratio of Tm/(Y+Yb+Tm) is a about 0.5±0.02%; and, the molar ratio of Yb/(Y+Yb+Tm) is greater than about 30%.

In certain embodiments, the molar ratio of Yb/(Y+Yb+Tm) is greater than about greater than about 70%. Preferably, the ratio is greater than about 90%. More preferably, the ratio is about 99.5%.

Each side of the cubic nanoparticle may have an average length of about 27±20 nm. In certain embodiments, each side of the cubic nanoparticle has an average length of about 27±10 nm. Preferably, each side of the cubic nanoparticle has an average length of about 27±2 nm.

In yet another aspect, the invention generally relates to a biocompatible UCNP comprising: a core of cubic nanocrystals comprising α-Na (Y, Yb, Tm)F₄; an epitaxial shell formed from CaF₂; and an outer layer of an organic acid which covers the epitaxial shell, wherein the molar ratio of Tm/(Y+Yb+Tm) is a about 0.5±0.02%; and the molar ratio of Yb/(Y+Yb+Tm) is greater than about 30%.

The organic acid may be one or more selected from citric acid, hyaluronic acid, polyacrylic acid, and phosphonic acid.

The organic acid of the outer layer may be conjugated to an amine (e.g., polyethylenimmine) or on the protein surfaces (e.g., bovine serum albumin, protamine, antibody). The amine may be conjugated to amine reactive functional groups, e.g., N-hydroxysulfosuccinimide or aldehyde derivatives.

In yet another aspect, the invention generally relates to a process for synthesizing UCNPs in a single reaction vessel. The process includes: heating a solvent mixture comprising an organic acid and an organic alkene in the vessel to an elevated temperature; injecting a core precursor solution comprising a mixture of rare earths into the vessel and the solvent mixture; and injecting a shell precursor solution into the vessel; and collecting the UCNPs.

The organic acid and the organic alkene of the solvent mixture each may have a 16- to 20-carbon backbone (e.g., a 16-, 17-, 18-, 19-, 20-carbon backbone). Preferably, the organic acid and the organic alkene is a solvent pair, wherein each of the acid and the alkene has the same number of carbon atoms. The acid and the acid-alkene pair can be hexadecanoic acid/1-hexadecene, eicosenoic acid/eicosene and, oleic acid/l-octadecene. Preferably, the acid-alkene pair is oleic acid/l-octadecene.

The heating step may be performed in two steps. In a first step, the solvent mixture of oleic acid-octadecene is heated to about 120° C. to degas trace oxygen and water. This is followed by a second step of heating to the elevated temperature of from about 300° C. to about 320° C. Preferably, the elevated temperature is from about 305° C. to about 315° C. More preferably, the elevated temperature is about 310° C.

The step of heating to the elevated temperature may include a step of first heating to a temperature of about 120° C., followed by a second step of heating to a temperature of about 310° C.

The core precursor solution includes a mixture of sodium trifluoracetate and rare earth trifluoracetate in the solvent mixture, for example. The rare earths may be selected from the combination of rare earths consisting of: (i) yttrium (Y), ytterbium (Yb) and thulium (Tm); (ii) gadolinium (Gd), ytterbium (Yb) and thulium (Tm); (iii) yttrium (Y), ytterbium (Yb) and erbium (Er); and, (iv) gadolinium (Gd), ytterbium (Yb) and erbium (Er). Preferably, the rare earths are a combination of yttrium (Y), ytterbium (Yb) and thulium (Tm).

The shell precursor solution may include $Ca(CF_3COO)_2$ and the solvent mixture.

In yet another aspect, the invention generally relates to a method for synthesizing UCNPs in a single reaction vessel. The method includes: a first step of heating a solvent mixture of oleic acid-octadecene to about 120° C. to degas trace oxygen and water; a second step of heating the solvent mixture to about 310° C.; a third step of injecting a core precursor solution comprising sodium trifluoracetate and trifluoracetates of yttrium (Y), ytterbium (Yb) and thulium (Tm) in oleic acid-octadecene into the vessel; a fourth step of injecting a solution of $Ca(CF_3COO)_2$ in oleic acid-octadecene into the vessel; and followed by a step of collecting the UCNPs.

The invention also relates to upconversion nanoparticles made by methods of the invention.

In yet another aspect, the invention generally relates to a photochemical method that includes: administering to a cell an UCNP coated with a light sensitive molecule; exciting the UCNP with a laser having a wavelength from about 900 nm to about 1064 nm; causing the UCNP to emit a luminescence at a wavelength of from about 340 nm to about 380 nm; and activating the light sensitive molecule. In certain embodiments, the excitation wavelength is about 980 nm, and the emission luminescence of the UCNP is about 365 nm.

In certain embodiments, the light sensitive molecule is activated at from about 340 nm to about 380 nm.

In certain embodiments, the light sensitive molecule is selected from derivatives of the 2-nitrobenzyl groups 7-nitroindolinyl groups and the coumarin moieties and their protected biological active macromolecules (e.g., caged organic dyes, photoactivable AMP, photoactivable GMP, caged DNA, caged RNA, caged proteins, and caged peptides).

In yet another aspect, the invention generally relates to a method of whole body imaging of an animal. The method includes: injecting the animal with the UCNPs; exciting the UCNPs with a laser having a wavelength from about 900 nm to about 1064 nm; and recording the emission luminescence at a wavelength of from about 600 nm to about 1000 nm. In certain embodiments, the excitation wavelength is about 980 nm, and the emission luminescence is measured at about 800 nm.

Applications that can benefit from the invention can include light emitting diodes, upconversion lasers, infrared detectors, chemical sensors, temperature sensors and biological labels, all of which incorporate a UCL material.

The present inventions will be explained in detail by showing the Examples, however, the present inventions are not restricted only thereto.

EXAMPLES

Materials $Y_2O_3$, (99.9%), $Yb_2O_3$ (99.9%), $Tm_2O_3$ (99.9%), $CF_3COONa$ (99.9%), $CF_3COOH$, $CaCO_3$, 1-octadecene (90%), oleic acid (90%), diethylene glycol (99%), toluene, citric acid monohydrate, 1-Ethyl-3-(3-dimethylaminopropyl) carbodiimide hydrochloride (EDC.HCl), N-hydroxysulfosuccinimide sodium salt (sulfo-NHS), and branched polyethylenimine (PEI, $M_w$ 25,000) were all purchased from Sigma-Aldrich and used without further purification. The trifluoroacetates of Y, Yb, and Tm were prepared as described. 5-carboxyfluorescein-bis-(5-carboxymethoxy-2-nitrobenzyl) ether, 0-alanine-carboxamide, succinimidyl ester (CMNB-caged carboxyfluorescein, SE) were purchased from Invitrogen.

Preparation of Ln Trifluoroacetates $Ln_2O_3$ powder was mixed with a little of water to form a slurry in a single-neck flask, then trifluoroacetic acid with 150% stoichiometric ratio was added under stirring. When the exothermic process was finished, the single-neck flask was heated to reflux under water condenser. It usually takes several hours to totally dissolve $Ln_2O_3$ powder and result in a transparent solution. Dry Ln trifluoroacetate powder was obtained via dehydration in a vacuum oven at 120° C.

Synthesis of α-$NaLnF_4$@$CaF_2$

In a three-neck reaction flask, a mixture of oleic acid (8 mmol) and 1-octadecene (8 mmol) was heated to 120° C. to degas trace oxygen and water. It was subsequently heated to the thermolysis reaction temperature (310° C.) under argon protection. The precursor solution for α-$NaLnF_4$ core was prepared by dispersing $CF_3COONa$ (0.500 mmol) and $Ln(CF_3COO)_3$ (Ln=Y, Yb, Tm, 0.500 mmol in total) within oleic acid (5 mmol) and 1-octadecene (5 mmol). After vacuum degassing, the core precursor solution was injected into the reaction flask at a rate of ca. 1 mL/min. Then the thermolysis reaction was kept at 310° C. for 1 h under dry argon flow. $Ca(CF_3COO)_2$ (2.000 mmol), oleic acid (5 mmol), and 1-octadecene (5 mmol) was mixed and vacuum degassed to make the shell precursor solution. This solution was injected in twice with an equal volume, followed by 30 min incubation at 310° C. after each injection. The α-$NaLnF_4$@$CaF_2$ upconversion nanoparticles (UCNPs) were precipitated by adding ethanol to the cooled reaction flask, and centrifugal washing twice with hexane/ethanol. The resulting white powder can be re-dispersed in hexane or toluene. For ligand exchanging experiments, the product from a single reaction was dispersed in 20.0 ml toluene (ca. 15 mg/mL). For characterization, α-$NaLnF_4$ core intermediates could be drawn from the reactor before injecting $Ca(CF_3COO)_2$.

Water-Soluble α-($NaYbF_4$:0.5% $Tm^{3+}$) @$CaF_2$ UCNPs by Ligand Exchange

The ligand exchange was adapted from a literature method for iron oxide nanoparticle. (Tierui Zhang, Jianping Ge, Yongxing Hu, and Yadong Yin, Nano Lett. 2007, 7, 3203). Poly(acrylic acid) (PAA, Mw 1800, 0.500 g) in diethylene glycol (8.0 mL) was heated to 110° C. with vigorous stirring under argon flow. 2 mL toluene solution of UCNPs (0.03 g) was then injected, and the mixture was heated to reflux for 1 h (ca. 240° C.) to remove the toluene. After cooling the solution, excess deionized water was added and water-soluble UCNPs were collected by centrifugal precipitation. The UCNPs were further purified in DI water 3 times by high-speed centrifugation, and preserved in 5 mL DI water for further modification.

$NOBF_4$ Assisted Ligand-Exchange Protocol

Also developed was a new ligand exchange protocol. In this protocol, nitrosonium tetrafluoroborate ($NOBF_4$) was employed to replace the original ligand (oleic acid), thus stabilizing the UCNPs in polar solvent such as N,N-dimethylforrnamide (DMF). In a typical phase transfer ligand-exchange reaction, 10 mL UCNPs hexane dispersion was first combined with 10 mL DMF to form a two-phase mixture, into which an excessive amount of $NOBF_4$ (20 mg) was added. The resulting mixture was stirred at room temperature until NCs were transferred from the hexane layer to the DMF layer, typically within 5 min. The $NOBF_4$ modified UCNPs were then precipitated by adding ethanol, purified by centrifugation, and redispersed in DMF. To prepare hydrophilic UCNPs, the NOBF4 ligands were further replaced by poly-acrylic acid (PAA). Briefly, 20 mg of PAA (Mw 1800) powder were added into the UCNPs DMP dispersion and the mixture was stirred at room temperature overnight. Then the PAA modified UCNPs were purified by centrifugation washing with DI water, and redispersed in water.

PEI- and HA-Coated UCNPs Using Layer-by-Layer (LbL) Technique

UCNPs coated with functional polymer were prepared by a commonly used assembly technique for nanoparticles. Branched polyethylenimine (PEI, Mw~25,000, Aldrich) and Sodium hyaluronate (Mw~10,000, Lifecore Biomedical Inc.) were dissolved in DI water to prepare stock solutions at a concentration of 10 mg/mL, respectively. The pH value was adjusted to 7.4 by adding diluted hydrochloric acid. For LbL assembly, PAA-coated UCNPs solution was mixed vigorously with the same volume of PEI solution. After 4 h of reaction, the PEI-coated UCNPs were purified by three times of centrifugal washing. By similar method the PEI-coated UCNPs can be further assembled with HA to get HA-coated UCNPs. All size and zeta potential measurements were made using a Zeta Sizer analyzer (Malvern Co., Nano series).

Characterizations of UCNPs.

The size and morphology of the nanocrystals were characterized by transmission electron microscopy (TEM) using a JEM-2010 microscope at an acceleration voltage of 200 KV. The powder x-ray diffraction (XRD) patterns were recorded by a Siemens D500 diffractometer using Cu Kα radiation (λ=0.15418 nm). The 2θ angle of the XRD spectra was recorded at a scanning rate of 5°/minute. Absorption spectra of transparent colloidal nanocrystals were acquired using a Shimadzu UV-Visible-NIR scanning spectrophotometer. UC photoluminescence spectra were recorded using a Fluorolog-3.11 Jobin Yvon spectrofluorometer with a slit width defining spectral resolution of 1 nm. The PL was excited at 975 nm using a fiber-coupled laser diode (Q-Photonics). All UC PL spectra have been corrected for the spectral sensitivity of the system. Photographic images of UC nanocrystals colloidal were taken by a digital camera (Lumix DMC-Fx520, Japan) without adding any filter. The PL decays were acquired using an Infinium oscilloscope (Hewlett-Packard) coupled to the PMT of Fluorolog-3.11 Jobin Yvon spectrofluorometer. When measuring the PL decays, the laser diode was operated in a pulsed mode with a repetition of 200 Hz and a pulse width of 50 μs.

Characterization of the Ln:Ca Ratio in α-NaLnF$_4$@CaF$_2$ UCNPs

The approximate Ln:Ca ratio in α-NaLnF$_4$@CaF$_2$ UCNPs can be estimated based on information about the core/shell geometry. The crystallographic unit-cells of α-NaLnF$_4$ and CaF$_2$ have similar sizes, and their compositions can be denoted as Na$_2$Ln$_2$F$_8$ and Ca$_4$F$_8$. The volume of α-NaLnF$_4$ core, V(Na$_2$Ln$_2$F$_8$), can be calculated in spherical approximation with known radius (ca. 11 nm). The total volume of α-NaLnF$_4$@CaF$_2$ particles can be calculated in cubic approximation with known edge (ca. 27 nm), so the volume of CaF$_2$ shell, V(Ca$_4$F$_8$), can be calculated by subtraction. Therefore, the Ca:Ln ratio can be obtained by the following formulae:

$$\frac{n_{Ln}}{n_{Ca}} = \frac{2 \cdot V_{Na2Ln2F8}/V_0}{4 \cdot V_{Ca4F8}/V_0}$$

$$= \frac{V_{Na2Ln2F8}}{2V_{Ca4F8}}$$

$$= \frac{4\pi \cdot r^3/3}{2(d^3 - 4\pi \cdot r^3/3)}$$

where the core radius r is 11 nm, and UCNP edge d is 27 nm, resulting in the Ca:Ln ratio of 5.06. The actual Ca:Ln ratio was measured by Inductive Coupled Plasma-mass Spectrometer, with an average value of 4.55. The details are shown in the following table.

TABLE 1

| Sample | Designed Yb$^{3+}$ level | Ca:Ln ratio | Measured Yb$^{3+}$ level |
|---|---|---|---|
| 1 | 30% | 4.24 | 27.4% |
| 2 | 40% | 4.55 | 38.0% |
| 3 | 50% | 4.39 | 50.0% |
| 4 | 60% | 5.36 | 54.0% |
| 5 | 70% | 4.08 | 70.6% |
| 6 | 90% | 3.94 | 91.5% |
| 7 | 99.5% | 5.28 | 99.6% |

Synthesis of β-NaLnF$_4$@UCNPs

β-NaLnF$_4$ UCNPs, used as reference samples, were prepared as described [S2]. Briefly, CF$_3$COONa (1.000 mmol) and Ln(CF$_3$COO)$_3$ (Ln=Y, Yb, Tm, 0.500 mmol in total) were mixed with oleic acid (10 mmol) and 1-octadecene (10 mmol) in a three-neck reaction flask. The mixture was vacuum degassed at 120° C. for 30 minutes. Then, the reaction flask was slowly heated to 330° C. at a rate of 15° C./min under argon flow, and kept at 330° C. for 30 minutes. The product was collected by centrifugal precipitation and re-dispersed in hexane.

Theoretical Simulation of UV Emission-Enhancement Mechanism

The upconversion process in Yb$^{3+}$-Tm$^{3+}$ system can be described by the following steady-state approximation equations:

$$\frac{dN_1}{dt} = 0 \tag{1-1}$$

$$= W_0 N_0 N_{Yb1} - (R_1 + B_1)N_1 - W_1 N_1 N_{Yb1}$$

$$\frac{dN_2}{dt} = 0 \tag{1-2}$$

$$= W_1 N_1 N_{Yb1} - (R_2 + B_2)N_2 - W_2 N_2 N_{Yb1}$$

$$\frac{dN_3}{dt} = 0 \tag{1-3}$$

$$= W_2 N_2 N_{Yb1} - (R_3 + B_3)N_3 - W_3 N_3 N_{Yb1}$$

$$\frac{dN_4}{dt} = 0 \tag{1-4}$$

$$= W_3 N_3 N_{Yb1} - (R_4 + B_4)N_4 - W_4 N_4 N_{Yb1}$$

$$N_{Yb1} = \sigma I N_{Yb0} \tag{1-5}$$

where $N_i$, $R_i$ and $B_i$ (i=0, 1, 2, 3, 4) are the population densities, radiative rates, and non radiative rates of the $^3H_6$, $^3F_4$, $^3H_4$, $^1G_4$ and $^1D_2$ states of the Tm$^{3+}$ ions, respectively; $W_i$ (i=0, 1, 2, 3, 4) represents the energy-transfer rates from excited Yb$^{3+}$ ion to the $^3H_6$, $^3F_4$, $^3H_4$, $^1G_4$ and $^1D_2$ states, respectively. $N_{Yb0}$ and $N_{Yb1}$ are the population densities of the Yb$^{3+}$ ions in the ground and excited states, respectively; I is the laser photon number density; and σ denotes the absorption cross-section of the Yb$^{3+}$ ions. Diffusion among Yb$^{3+}$ sensitizers has been shown to be a thermally assisted, incoherent and fast hopping process, and energy transfer between Yb$^{3+}$ and Tm$^{3+}$ creates a weak perturbation. This result justifies the use of rate equations for energy transfer upconversion processes. Generally, the linear decay rates ($R_i$ and $B_i$) in the intermediate state are larger than the upconversion rate ($W_i$) in this state. Based on this assumption, equations (1-1) to (1-4) can be simplified to:

$$N_1 = \frac{W_0 N_{Yb0}}{R_1 + B_1} \sigma I N_0 \tag{2-1}$$

$$N_2 = \frac{W_1 W_0 (N_{Yb0})^2}{(R_2 + B_2)(R_1 + B_1)} (\sigma I)^2 N_0 \tag{2-2}$$

$$N_3 = \frac{W_2 W_1 W_0 (N_{Yb0})^3}{(R_3 + B_3)(R_2 + B_2)(R_1 + B_1)} (\sigma I)^3 N_0 \tag{2-3}$$

$$N_4 = \frac{W_3 W_2 W_1 W_0 (N_{Yb0})^4}{(R_4 + B_4)(R_3 + B_3)(R_2 + B_2)(R_1 + B_1)} (\sigma I)^4 N_0 \tag{2-4}$$

As the radiative rate generally is low due to the long lifetime of lanthanide ions, and the nonradiative rates in nanomaterials are generally high due to their large surface-to volume ratio, equations (2-1) to (2-4) can thus be simplified to:

$$N_1 = \frac{W_0 N_{Yb0}}{B_1} \sigma I N_0 \tag{3-1}$$

$$N_2 = \frac{W_1 W_0 (N_{Yb0})^2}{B_2 B_1} (\sigma I)^2 N_0 \tag{3-2}$$

$$N_3 = \frac{W_2 W_1 W_0 (N_{Yb0})^3}{B_3 B_2 B_1} (\sigma I)^3 N_0 \tag{3-3}$$

$$N_4 = \frac{W_3 W_2 W_1 W_0 (N_{Yb0})^4}{B_4 B_3 B_2 B_1} (\sigma I)^4 N_0 \tag{3-4}$$

According to equations (3-1) to (3-4), the upconversion emissions peaked at 802 nm, 478 nm, and 362 nm will have quadratic, cubic, and quartic dependence on the laser intensity, illustrating their two-, three- and four-photon processes. These predictions agree well with experiment results. It should be noted in equation (3-4) that the laser photon number density I, the absorption cross-section of $Yb^{3+}$ ion σ, and the $Tm^{3+}$ ion concentration $N_0$ are fixed parameters. To maximize the upconversion emission at 362 nm, the parameter needs to be maximized. Since the $CaF_2$ shell has effectively eliminated quenching sites of t-$NaLnF_4$, an increase in the $Yb^{3+}$ ion concentration can increase the energy transfer rates $W_i$ (i=0, 1, 2, 3) by decreasing the distance between the sensitizer $Yb^{3+}$ and the activator $Tm^{3+}$, thus increasing the efficiency of the upconversion process. Increase in the $Yb^{3+}$ concentration also increases the parameter value of ($N_{Yb0}$), which further amplifies the upconversion output. In addition, the difference between equations (3-4) and (3-3) indicates that the enhancement for UV emission is stronger than that for blue emissions due to the stronger dependence on the concentration of $Yb^{3+}$ ions at higher energy. (FIG. 9).

Lifetime and Quantum Yield Measurement

The upconversion emission decays were recorded by an oscilloscope (Infinium series, Hewlett-Packard) coupled to the output of photomultiplier tube of a spectrofluorimeter (Fluorolog 3.11, HORIBA Jobin Yvon), using excitation with laser diode (Q-Photonics) operating in pulsed mode. UCNPs were dispersed in hexane at ca. 10 mg/mL for the measurement. The emission lifetime was obtained by single-exponential fitting method. The quantum yield of UV emissions was measured by using core/shell β-UCNPs with a known quantum yield as reference (power density=$10^3$ W/cm$^2$). According to the following formula, QYR is defined as the quantum yield of 30 nm β-$NaYF_4$:20% Yb, 2% Er@β-$NaYF_4$ UCNPs (ca. 0.3%)[S4], ES and ER are integral intensities of upconversion emission peaks for sample and reference UCNPs, respectively, in hexane solution (10 mg/mL), and the absorbance value at 975 nm (AS and AR) was measured using a UV-visible-NIR spectrophotometer (Shimadzu 3600)

$$QY_s = QY_R \cdot (E_S/E_R) \cdot (A_R/A_S)$$

UCNP Surface Modifications and DLS, Zeta Potential Characterizations, Ligand Exchange for Water-Soluble UCNPs The ligand exchange for UCNPs was modified from a reported method. Citric acid monohydrate (0.300 g) in diethylene glycol (8.0 mL) was heated to 110° C. with vigorous stirring under argon flow. 2 mL toluene solution of UCNPs (0.03 g) was then injected, and the mixture was heated to reflux for 1 h (ca. 240° C.) to remove the toluene. After cooling the solution, excess deionized water was added and water-soluble UCNPs were collected by centrifugal precipitation. The UCNPs were further purified in DI water 3 times by high-speed centrifugation, and preserved in 5 mL DI water for further modification.

Modification of UCNPs with Caged Fluorescein

The citric acid-capped UCNPs were covalently grafted with branched polyethylenimine (PEI) to introduce primary amino groups, which could be subsequently conjugated to the succinimidyl ester derivate of caged fluorescein. The PEI layer also facilitated cellular uptake of the dye-labeled UCNPs. For PEI grafting, 30 mg hydrophilic UCNPs in 5 mL DI water were activated by 1-Ethyl-3-(3-dimethylaminopropyl) carbodiimide hydrochloride (EDC.HCl, 50 mg) and sulfo-NHS (5 mg) to form the succinimidyl ester. Then PEI (20 mg) in PBS buffer (2 mL) was added for amido linkage. After 2 h of incubation at room temperature, the PEI-UCNPs were purified by centrifugation and redispersed in DI water (5 mL). To prepare caged fluorescein-UCNPs (cF-UCNPs), 0.1 mg of caged-fluorescein succinimidyl ester was added to PEI-UCNPs in solution. The reaction was incubated in a dark room for 2 h and purified by three centrifugal washes in DI water. The product was preserved in 2 mL DI water.

Cytotoxicity Assay and Intracellular Photoactivation

The cytotoxicity of cF-UCNPs was tested by the standard MTT (3-(4,5-dimethylthiazol-2-yl)-2,5-diphenyltetrazolium bromide) assay. HeLa cells were grown in DMEM media supplemented with 10% fetal bovine serum and 50 units/mL penicillin. The cell suspension (100 μL, $2 \times 10^4$ cells per well) was dispensed into a 96-well plate and pre-incubated at 37° C. and 5% $CO_2$ for 12 h. After washing the cells with PBS, 100 μL of culture medium with various concentrations of cF-UCNPs was added to the wells in triplicate. For control wells, the same volume of pure culture medium was used. After 24 h of incubation, cell survival rate was measured by MTT cell proliferation assay (FIG. 15).

To test cellular photoactivation, HeLa cells were cultured in 35 mm glass bottom dishes for 12 h. Cell cultures were renewed with 2 mL of culture medium containing 20 g/mL of cF-UCNPs and incubated at 37° C. and 5% $CO_2$ for 2 h. After washing the cells with PBS, fresh medium was added. The photoactivation experiment was carried out on a confocal/multi-photon fluorescence microscope (Leica TCS-SP2/AOBS) equipped with 975 nm CW laser diode. Light stimulation was applied in a 110 m×110 μm area through a 60× oil immersion objective, with a laser scanning frequency of 200 Hz. The 975-nm CW laser output power was 11 mW. Fluorescence images of uncaged fluorescein inside cells were acquired using excitation at 458 nm and photoluminescence images of UCNPs, which show similar intracellular distribution pattern, were obtained using excitation with 975 nm laser diode. Blue upconversion emission from UCNP was imaged in this case (FIG. 16).

Photoactivation was also demonstrated under a two-photon microscope (Zeiss LSM 710) using excitation at 975 nm by a femto-second pulsed laser. Light stimulation was applied in a 150 μm×150 μm area through a 20× water immersion objective, with a scanning speed of 15 s/frame. The 975-nm pulsed laser output power was 120 mW. Two photon excited fluorescence images of uncaged fluorescein were acquired with 880-nm pulsed laser excitation (FIG. 17).

Synthesis of Hyaluronic Acid (HA) Cated α-$NaYbF_4$:TM@$CaF_2$ UCNPs

UCNPs coated with functional polymer were prepared by a commonly used layer-by-layer assembly technique for nanoparticles (S7). Hydrophobic UCNPs were first processed by ligand exchanging with polyacrylic acid) (PAA, M 1800) (S6). Brifely, PAA, 0.500 g) in diethylene glycol (8.0 mL) was heated to 110° C. with vigorous stirring under argon flow, then 2 mL toluene solution of UCNPs (0.03 g) was then injected, and the mixture was heated to reflux for 1 h (ca. 240° C.) to remove the toluene. After cooling the solution, excess deionized water was added and water-soluble UCNPs were collected by centrifugal precipitation. The UCNPs were further purified in DI water 3 times by high-speed centrifugation, and preserved in 5 mL DI water. For layer-by-layer assembly modification, branched polyethylenimine (PEI, Mw~25,000) and Sodium hyaluronate (Mw~10,000) were dissolved in DI water to prepare stock solutions at a concentration of 10 mg/mL, respectively. The pH value was adjusted to 7.4 by adding diluted hydrochloric acid. The PAA-coated UCNPs solution was mixed vigorously with the same volume of PEI solution. After 4 h of reaction, the PEI-coated UCNPs were obtained by three times of centrifugal washing. By similar method the PEI-coated UCNPs can be further assembled with HA to get HA-coated UCNPs. All size and zeta potential measurements were made using a Zeta Sizer analyzer (Malvern Co., Nano series).

In Vivo Imaging Using α-NaYbF$_4$: Tm@CaF$_2$ UCNPs

FIG. 20 shows the in vivo imaging of α-NaYbF$_4$: Tm@CaF$_2$ UCNPs in mouse. Balb-c mice intravenously were injected (tail vein) with UCNPs (700 pmols/kg) coated with hyaluronic acid (i.e., an anionic, nonsulfacted gylcosaminoglycan) and imaged at 3 h post-injection. In vivo photoluminescence imaging was accomplished using the Maestro fluorescence imaging system (Cri). The UCNPs were excited at 980 nm by defocused emission from the fiber coupled laser diode introduced into the imaging chamber. An emission filter (850 SP) before the imaging CCD camera (Sony icx285, working range: 500- to 950-nm) was used to block the excitation light. FIG. 2 shows the Maestro whole-body images of a Balb-c mouse injected with the UCNPs. These high contrast images clearly show that it is feasible to image and spectrally distinguish the characteristic emissions of UCNPs (shown in red), using the Maestro imaging software. A scan from 700 to 850 nm showed an intense NIR luminescence peaking at 800 nm. The signal was readily detectable both through the skin of shaved mice and after dissection. The signal-to-noise-ratio is 310, which is about a 10-fold increase when compared to that reported in literature for in vivo imaging by UCNP. The images show high levels of photoluminescence in the liver and spleen, indicating their high uptake of UCNPs. The high contrast between the background and photoluminescence signal of UCNPs results from NIR to NIR upconversion photoluminescence. It is worth noting that the mice injected with the UCNPs remained healthy at 270 days post injection.

To explore the possibility of upconverted luminescence detection from even deeper tissue depth, 1.25 inch (3.2 cm) thick pork was placed between the laser sources and a cuvette (1 cm×5 cm×0.5 cm) prefilled with UCNPs (225 nM). FIG. 20 shows that the NIR upconverted emissions can still be clearly detected from the scattering background. Such tissue penetration depth exhibited by the NIR$_{in}$-NIR$_{out}$ UCNPs should satisfy the needs of both small and large animal in vivo imaging.

Determination of Upconversion Quantum Yield of Photoluminescence

The quantum yield (QY) of photoluminescence is defined as the ratio of the number of the emitted photons to the number of the absorbed photons. QY can be measured either by absolute method or on a relative basis using standard with known QY as a reference. Here, it was determined the NIR UC PL QY of our core/shell nanocrystals by referencing to the standard: IR 26 dye dissolved in 1,2-dichloroethane (DCE) with a known QY of 0.05%. The QY of the nanoparticles, QY$_X$, was calculated according to the following equation:

$$QY_X = QY_R \cdot \frac{E_R}{E_X} \cdot \frac{A_R}{A_X} \cdot \frac{I_R}{I_X} \cdot \frac{N_X^2}{N_R^2} \tag{S1}$$

where QY$_R$ and QY$_X$ are the quantum yields of the referenced standard sample and the sample to be determined, respectively; E$_R$ and E$_X$ are the numbers of the emitted photons for referenced standard sample and measured sample, respectively; A$_R$ and A$_X$ are the numbers of the photons absorbed by referenced standard sample and measured sample, respectively, I$_R$ and I$_X$ indicate the relative intensity of the exciting light for referenced standard sample and measured sample, respectively; N$_R$ and N$_X$ are the average refractive index of the solvent used for dissolving referenced standard sample and measured sample, respectively. Subscripts R and X refer to the referenced standard sample and the sample to be measured, respectively.

Exactly the same geometry was used to excite the referenced standard sample (IR 26 dye, Exciton, Inc.) dissolved in 1,2-dichloroethane (DCE) and the α-NaYbF$_4$:0.5% Tm@CaF$_2$ UCNPs dispersed in hexane and to detect their commitment PL spectra. A calibrated SPEX 270M spectrometer (Jobin Yvon) equipped with an InGaAs TE-cooled photodiode (Electro-Optical Systems, Inc.) was utilized for recording NIR PL. During the QY measurement, the same laser at 975 nm is employed to perform the excitation; the absorbance of the referenced standard sample and the measured core/shell samples has been matched at 970 nm by adjusting the concentration of these two samples. To avoid the effect of reabsorption, an "optically thin" absorbance of 0.09 at 975 nm is utilized.

Since the laser excitation intensity and the absorbance are same, the parameter of A$_R$I$_R$/A$_X$I$_X$ in Equation (S1) equals 1. It is known that hexane has a refractive index of 1.38 while the DCE has a refractive index of 1.44. The parameter of N$_X^2$/N$_R^2$ in Equation (S1) was, therefore, determined to be 0.92, The equation (S1) can thus be simplified to, $$QY_X = QY_R \cdot \frac{E_R}{E_X} \cdot 0.92 \tag{S2}$$

Figure 25:
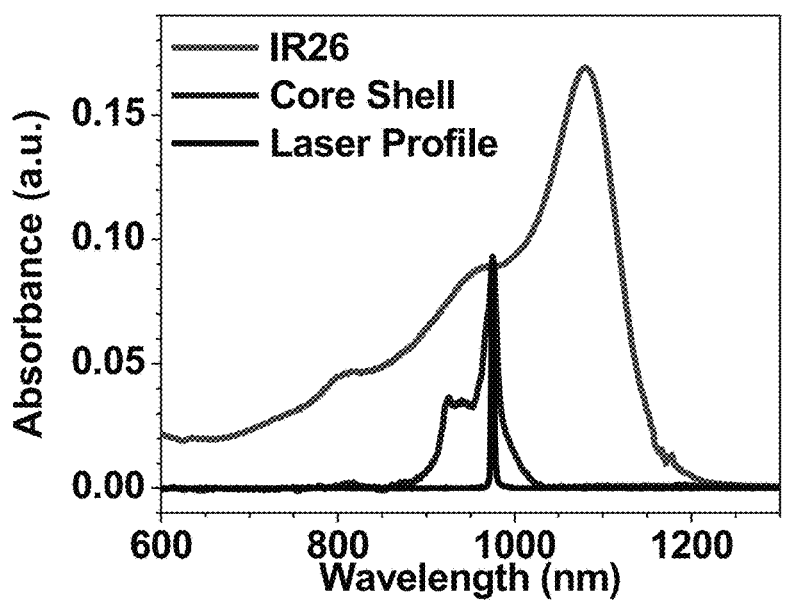
FIG. 25 shows exemplary absorbance of the referenced standard IR 26 dissolved in 1,2-dichloroethane (DCE) and the measured α-$NaYbF_4$:0.5% Tm@$CaF_2$ core/shell UCNPs dissolved in hexane; they have been matched at 975 nm by adjusting the concentration of these two samples.
Figure 26:
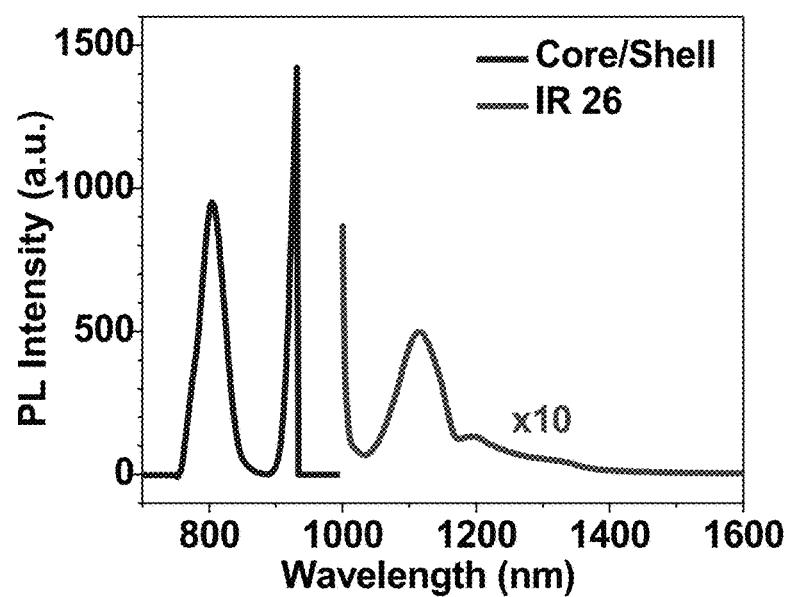
FIG. 26 shows exemplary anti-stokes NIR UC PL spectra of α-$NaYbF_4$:0.5% Tm@$CaF_2$ core/shell dispersed in hexane and stokes NIR PL of referenced standard IR 26 dye dissolved in DCE under 975 nm excitation of 0.3 W/cm$^2$. The PL intensity of IR 26 dye in DCE was magnified by 10 times.

As illustrated in FIG. 25, the integrated intensity of NIR UC PL in the wavelength range of 700-900 nm for α-NaYbF$_4$:0.5% Tm@CaF$_2$ core/shell nanoparitcles is about 12 times higher than the integrated NIR PL intensity of standard IR 26 dye in a spectroscopic range of 1050-1600 nm. According to Equation (S2), this intensity ratio corresponds to a QY of 0.6% for α-NaYbF$_4$:0.5% Tm@CaF$_2$ core/shell under low excitation density of 0.3 W/cm$^2$ at 975 nm.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

REFERENCES

1. Bratton, D.; Yang, D.; Dai, J. Y.; Ober, C. K., *Polym Advan Technol* 2006, 17, 94-103.
2. (a) Han, G.; Mokari, T.; Ajo-Franklin, C.; Cohen, B. E., Caged Quantum Dots. *J Am Chem Soc* 2008, 130, 15811-+; (b) Fernandez-Suarez, M.; Ting, A. Y., *Nat Rev Mol Cell Bio* 2008, 9, 929-943.
3. (a) Lee, H. M.; Larson, D. R.; Lawrence, D. S., *Acs Chem Biol* 2009, 4, 409-27; (b) Szacilowski, K.; Macyk, W.; Drzewiecka-Matuszek, A.; Brindell, M.; Stochel, G., *Chem Rev* 2005, 105 (6), 2647-94.

4. (a) Han, G.; You, C. C.; Kim, B. J.; Turingan, R. S.; Forbes, N. S.; Martin, C. T.; Rotello, V. M., *Angew Chem Int Edit* 2006, 45, 3165-3169; (b) Sortino, S., *J Mater Chem* 2012, 22 (2), 301-318.
5. Mayer, G.; Heckel, A., *Angew Chem Int Edit* 2006, 45, 4900-4921.
6. (a) Agasti, S. S.; Chompoosor, A.; You, C. C.; Ghosh, P.; Kim, C. K.; Rotello, V. M., *J Am Chem Soc* 2009, 131, 5728-+; (b) Shamay, Y.; Adar, L.; Ashkenasy, G.; David, A., *Biomaterials* 2011, 32, 1377-1386.
7. Meunier, J. R.; Sarasin, A.; Marrot, L., *Photochem Photobiol* 2002, 75, 437-447.
8. Zhou, J.; Liu, Z.; Li, F. Y., *Chem Soc Rev* 2012, 10.1039/c1cs15187 h.
9. Wang, C.; Tao, H. Q.; Cheng, L.; Liu, Z., *Biomaterials* 2011, 32, 6145-6154.
10. (a) Yue, S. H.; Slipchenko, M. N.; Cheng, J. X., *Laser Photonics Rev* 2011, 5, 496-512; (b) Bredas, J. L.; Adant, C.; Tackx, P.; Persoons, A.; Pierce, B. M., *Chem Rev* 1994, 94, 243-278.
11. Haase, M.; Schafer, H., *Angew Chem Int Edit* 2011, 50, 5808-5829.
12. (a) Mahalingam, V.; Vetrone, F.; Naccache, R.; Speghini, A.; Capobianco, J. A., *Adv Mater* 2009, 21, 4025-+; (b) Yanes, A. C.; Santana-Alonso, A.; Mendez-Ramos, J.; del-Castillo, J.; Rodriguez, V. D., *Adv Funct Mater* 2011, 21, 3136-3142.
13. Wang, F.; Liu, X. G., *Chem Soc Rev* 2009, 38, 976-989.
14. (a) Boyer, J. C.; Carling, C. J.; Gates, B. D.; Branda, N. R., *J Am Chem Soc* 2010, 132, 15766-15772; (b) Carling, C. J.; Nourmohammadian, F.; Boyer, J. C.; Branda, N. R., *Angew Chem Int Edit* 2010, 49, 3782-3785.
15. (a) Huignard, A.; V, B.; Franville, A. C.; Gacoin, T.; Boilot, J. P., *J Phys Chem B* 2003, 107, 6754-6759; (b) Wang, F.; Wang, J. A.; Liu, X. G., *Angew Chem Int Edit* 2010, 49, 7456-7460.
16. Pandozzi, F.; Vetrone, F.; Boyer, J. C.; Naccache, R.; Capobianco, J. A.; Speghini, A.; Bettinelli, M., *J Phys Chem B* 2005, 109, 17400-17405.
17. Yin, A. X.; Zhang, Y. W.; Sun, L. D.; Yan, C. H., *Nanoscale* 2010, 2, 953-959.
18. (a) Boyer, J. C.; Cuccia, L. A.; Capobianco, J. A., *Nano Lett* 2007, 7, 847-852; (b) Park, Y. I.; Kim, J. H.; Lee, K. T.; Jeon, K. S.; Bin Na, H.; Yu, J. H.; Kim, H. M.; Lee, N.; Choi, S. H.; Baik, S. I.; Kim, H.; Park, S. P.; Park, B. J.; Kim, Y. W.; Lee, S. H.; Yoon, S. Y.; Song, I. C.; Moon, W. K.; Suh, Y. D.; Hyeon, T., *Adv Mater* 2009, 21, 4467-+.
19. (a) Wang, G. F.; Peng, Q.; Li, Y. D., *J Am Chem Soc* 2009, 131, 14200-+; (b) Wang, Y. F.; Sun, L. D.; Xiao, J. W.; Feng, W.; Zhou, J. C.; Shen, J.; Yan, C. H., *Chem. Eur. J.* 2012. 10.1002/36hem.201103485.
20. Boyer, J. C.; van Veggel, F. C. J. M., *Nanoscale* 2010, 2, 1417-1419.
21. Shestopalov, I. A.; Chen, J. K., *Chem Soc Rev* 2008, 37, 1294-1307.
22. Kobayashi, T.; Urano, Y.; Kamiya, M.; Ueno, T.; Kojima, H.; Nagano, T., *J Am Chem Soc* 2007, 129, 6696-+.
23. Nam, S. H.; Bae, Y. M.; II Park, Y.; Kim, J. H.; Kim, H. M.; Choi, J. S.; Lee, K. T.; Hyeon, T.; Suh, Y. D., *Angew Chem Int Edit* 2011, 50, 6093-6097.
24. John E. Roberts, *J. Am. Chem. Soc.,* 1961, 83, 1087.
25. Hao-Xin Mai, Ya-Wen Zhang, Rui Si, Zheng-Guang Yan, Ling-dong Sun, Li-Ping, You, and Chun-Hua Yan, *J. Am. Chem. Soc.* 2006, 128, 6426.
26. John-Christopher Boyer, and Frank C. J. M. van Veggel, *Nanoscale,* 2010, 2, 1417.
27. Guanying Chen, Tymish Y. Ohulchanskyy, Aliaksandr Kachynski, Hans Ågren, and Paras N. Prasad, *ACS Nano,* 2011, 5, 4981.
28. Francois Auzel, *Chem. Rev.* 2004, 104, 139.
29. Tierui Zhang, Jianping Ge, Yongxing Hu, and Yadong Yin, *Nano Lett.* 2007, 7, 3203.
30. Schneider, G.; Decher, G.; *Langmuir* 2008, 24, 1778.
31. Prasad, P. N., *Introduction to Biophotonics*; Wiley-Interscience: New York, 2003; p 255-360.
32. Prasad, P. N., *Nanophotonics*; Wiley-Interscience: New York, 2004; p 355-381.
33. Hilderbrand, S.; Weissleder, R. Near-Infrared Fluorescence: Application to In Vivo Molecular Imaging. *Curr. Opin. Chem. Biol.* 2010, 14, 71-79.
34. Smith, A. M.; Mancini, M. C.; Nie, S. M. Second Window for In Vivo Imaging. *Nature Nanotechnol.* 2009, 4, 710-711.
35. Alivisatos, A. The Use of Nanocrystals in Biological Detection. *Nat. Biotechnol.* 2004, 22, 47-52.
36. Farkas, D. L.; Du, C.; Fisher, G. W.; Lau, C.; Niu, W.; Wachman, E.; Levenson, R. M. *Comput. Med. Imaging Graph.* 1998, 22, 89-102.
37. Sharma, P.; Brown, S.; Walter, G.; Santra, S.; Moudgil, B. Nanoparticles for Bioimaging. *Adv. Colloid Interface Sci.* 2006, 123-126, 471-485.
38. Welsher, K.; Liu, Z.; Sherlock, S.; Robinson, J.; Chen, Z.; Daranciang, D.; Dai, H. J. A Route to Brightly Fluorescent Carbon Nanotubes for Near-Infrared Imaging in Mice. *Nature Nanotechnol.* 2009, 4, 773-780.
39. Gao, J.; Chen, K.; Xie, R.; Xie, J; Lee, S.; Cheng, Z.; Peng, X.; Chen, X. Y. Ultrasmall Near-Infrared Non-cadmium Quantum Dots for in vivo Tumor Imaging. *Small* 2009, 6, 256-261.
40. Chen, G. Y.; Ohulchanskyy, T. Y.; Liu, S.; Law, W. C.; Wu, F.; Swihart, M. T.; Ågren, H.; Prasad, P. N. Core/Shell NaGdF$_4$:Nd$^{3+}$/NaGdF$_4$ Nanocrystals with Efficient Near-Infrared to Near-Infrared Downconversion Photoluminescence for Bioimaging Applications. *ACS Nano* 2012, 6, 2969-2977.
41. Yong, K.-T.; Qian, J.; Roy, I.; Lee, H. H.; Bergey, E. J.; Tramposch, K. M.; He, S.; Swihart, M. T.; Maitra, A.; Prasad, P. N. Quantum Rod Bioconjugates as Targeted Probes for Confocal and Two-Photon Fluorescence Imaging of Cancer Cells. *Nano Lett.* 2007, 7, 761-765.
42. Wang, H.; Huff, T. B.; Zweifel, D. A.; He, W.; Low, P.; Wei, A.; Cheng, J. X. In Vitro and In Vivo Two-Photon Luminescence Imaging of Single Gold Nanorods. *Proc. Natl. Acad. Sci. U.S.A.* 2005, 102, 15752-15756.
43. Pantazis, P.; Maloney, J.; Wu, D.; Fraser, S. E. Second Harmonic Generating (SHG) Nanoprobes for In Vivo Imaging. *Proc. Natl. Acad. Sci.* U.S.A. 2010, 107, 14535-14540.
44. Ohulchanskyy, T. Y.; Roy, I.; Yong, K. T.; Pudavar, H. E.; Prasad, P. N. High-Resolution Light Microscopy Using Luminescent Nanoparticles. *Wiley Interdiscip. Rev. Nanomed. Nanobiotechnol.* 2010, 2, 162-175.
45. Wang, F.; Deng, R.; Wang, J.; Wang, Q.; Han, Y.; Zhu, H.; Chen, X.; Liu, X. *Nature Mater.* 2011, 10, 968-973.
46. Wang, F.; Banerjee, D.; Liu, Y. S.; Chen, X. Y.; Liu, X. G. Upconversion Nanoparticles in Biological Labeling, Imaging, and Therapy. *Analyst* 2010, 135, 1839-1854.
47. Mader, H.; Kele, P.; Saleh, S.; Wolfbeis, O. Upconverting Luminescent Nanoparticles for Use in Bioconjugation and Bioimaging. *Curr. Opin. Chem. Biol.* 2010, 14, 582-596.

48. Chatterjee, D. K.; Gnanasammandhan, M. K.; Zhang, Y. Small Upconverting Fluorescent Nanoparticles for Biomedical Applications. *Small* 2010, 6, 2781-2795.
49. Zhou, J.; Liu, Z.; Li, F. Upconversion Nanophosphors for Small-Animal Imaging. *Chem. Soc. Rev.* 2012, 41, 1323-1349.
50. Bogdan, N.; Vetrone, F.; Ozin, G. A.; Capobianco, J. A. Synthesis of Ligand-Free Colloidally Stable Water Dispersible Brightly Luminescent Lanthanide-Doped Upconverting Nanoparticles *Nano Lett.* 2011, 11, 835-840.
51. Haase, M.; Schafer, H. Upconverting Nanoparticles. *Angew. Chem. Int. Ed.* 2011, 50, 5808-5829.
52. Heer, S.; Kompe, K.; Gidel, H. U.; Haase, M. Highly Efficient Multicolour Upconversion Emission in Transparent Colloids of Lanthanide-Doped $NaYF_4$ Nanocrystals. *Adv. Mater.* 2004, 16, 2102-2105.
53. Chatterjee, D. K.; Rufaihah, A. J.; Zhang, Y. Upconversion fluorescence imaging of cells and small animals using lanthanide doped nanocrystals. *Biomaterials.* 2008, 29, 937-943.
54. Wu, S. W.; Han, G.; Milliron, D. J.; Aloni, S.; Altoe, V.; Talapin, D. V.; Cohen, B. E.; Schuck, P. J. Non-blinking and Photostable Upconverted Luminescence from Single Lanthanide-doped Nanocrystals. *Proc. Natl. Acad. Sci. U.S.A.* 2009, 106, 10917-10921.
55. Nam, S.; Bae, Y.; Park, Y.; Kim, J.; Kim, H.; Choi, J.; Lee, K.; Hyeon, T.; Suh, Y. Long-Term Real-Time Tracking of Lanthanide Ion Doped Upconverting Nanoparticles in Living Cells. *Angew. Chem. Int. Ed.* 2011, 50, 6093-6097.
56. Chen, G. Y.; Ohulchanskyy, T. Y.; Kachynski, A.; Ågren, H.; Prasad, P. N. Intense Visible and Near-Infrared Upconversion Photoluminescence in Colloidal $LiYF_4$:$Er^{3+}$ Nanocrystals under Excitation at 1490 nm. *ACS Nano* 2011, 5, 4981-4986.
57. Liu, Q.; Sun, Y.; Yang, T. S.; Feng, W.; Li, C. G.; Li, F. Y. Sub-10 nm Hexagonal Lanthanide-Doped NaLuF4 Upconversion Nanocrystals for Sensitive Bioimaging In Vivo. *J. Am. Chem. Soc.* 2011, 133, 17122-17125.
58. Xiong, L.; Chen, Z.; Tian, Q.; Cao, T.; Xu, C.; Li, F. *Anal. Chem.* 2009, 81, 8687-8694.
59. Nyk, M.; Kumar, R.; Ohulchanskyy, T. Y.; Bergey, E. J.; Prasad, P. N. High Contrast in Vitro and in Vivo Photoluminescence Bioimaging Using Near Infrared to Near Infrared Upconversion in $Tm^{3+}$ and $Yb^{3+}$ Doped Fluoride Nanophosphors. *Nano Lett.* 2008, 8, 3834-3838.
60. Zhang, F.; Braun, G., Shi, Y. F.; Zhang, Y. C.; Sun, X. H.; Reich, N. O.; Zhao, D. Y.; Stucky, G. Fabrication of $Ag@SiO_2@Y_2O_3$:$Er^{3+}$ Nanostructures for Bioimaging: Tuning of the Upconversion Fluorescence with Silver Nanoparticles. *J. Am. Chem. Soc.* 2010, 132, 2850-2851.
61. Zhang, H.; Li, Y.; Ivanov, I. A.; Qu, Y.; Huang, Y.; Duan, X. Plasmonic Modulation of the Upconversion Fluorescence in $NaYF_4$:Yb/Tm Hexaplate Nanocrystals Using Gold Nanoparticles or Nanoshells. *Angew. Chem. Int. Ed.* 2010, 49, 2865-2868.
62. Yi, G. S.; Chow, G. M. Water-Soluble $NaYF_4$:Yb,Er©/$NaYF_4$/Polymer Core/Shell/Shell Nanoparticles with Significant Enhancement of Upconversion Fluorescence. *Chem. Mater.* 2007, 19, 341-343.
63. Chen, G. Y.; Ohulchanskyy, T. Y.; Law. W. C.; Ågren, H.; Prasad, P. N. Monodisperse $NaYbF_4$:$Tm^{3+}$/$NaGdF_4$ Core/Shell Nanocrystals with Near-Infrared to Near-Infrared Upconversion Photoluminescence and Magnetic Resonance Properties. *Nanoscale* 2011, 3, 2003-2008.
64. Chen, G. Y.; Ohulchanskyy, T. Y.; Kumar, R.; Ågren, H.; Prasad, P. N. Ultrasmall Monodisperse $NaYF_4$:$Yb^{3+}$/$Tm^{3+}$ Nanocrystals with Enhanced Near-Infrared to Near-Infrared Upconversion Photoluminescence. *ACS Nano* 2010, 4, 3163-3168.
65. Wang, G.; Peng, Q.; Li, Y. Upconversion Luminescence of Monodisperse $CaF_2$:$Yb^{3+}$/$Er^{3+}$ Nanocrystals. *J. Am. Chem. Soc.* 2009, 131, 14200-14201.
66. Wang, Y. F.; Sun, L.; Xiao, J. W.; Feng, W.; Zhou, J. C.; Shen, J.; Yan, C. H. Rare-Earth Nanoparticles with Enhanced Upconversion Emission and Suppressed Rare-Earth-Ion Leakage. *Chem. Eur. J.* 2012, 18, 5558-5564.
67. Dong, N.; Pedroi, M.; Piccine, F.; Conti, G.; Sbarbati; Enrique, J.; Ramirez-Hernádez J.; Maestro, L. M.; Cruz, M. C.; SanzRodriguez, F.; Juarranz, A.; Chen, F.; Vetrone, F.; Capobianco, J. A.; Sole G.; Bettinelli, M.; Jaque, D.; Speghini, A. NIR-to-NIR Two-Photon Excited $CaF_2$:$Tm^{3+}$, $Yb^{3+}$ Nanoparticles: Multifunctional Nanoprobes for Highly Penerating Fluorescence Bioimaging. *ACS Nano* 2011, 5, 8665-8671.
68. Shan, J. N.; Uddi, M.; Yao, N.; Ju, Y. G. Anomalous Raman Scattering of Colloidal $Yb^{3+}$, $Er^{3+}$ Codoped $NaYF_4$ Nanophosphors and Dynamic Probing of the Upconversion Luminescence. *Adv. Funct. Mater.* 2010, 20, 3530-3537.
69. Kramer, K.; Biner, D.; Frei, G.; Giidel, Hehlen, M.; Lüthi, S. Hexagonal Sodium Yttrium Fluoride Based Green and Blue Emitting Upconversion Phosphors. *Chem. Mater.* 2004, 16, 1244-1251.
70. Boyer, J.; Veggel, F. Absolute Quantum Yield Measurements of Colloidal NaYF4:$Er^{3+}$, $Yb^{3+}$ Upconverting Nanoparticles. *Nanoscale* 2010, 2, 1417-1419.
71. Filion, T. M.; Kutikov A.; Song J. Chemically Modified Cellulose Fibrous Meshes for Use as Tissue Engineering Scaffolds. *Bioorg. Med. Chem. Lett.* 2011, 21, 5067-5070.
72. Schneider, G.; Decher, G.; Langmuir 2008, 24, 1778-1789.
73. Rhys Williams, A. T.; Winfield, S. A.; Miller, J. N. Analyst, 1983, 108, 1067-1071.
74. Semonin, O. E.; Johnson, J. C.; Luther, J. M.; Midgett, A. G.; Nozik, A. J.; Beard, M. C. *J. Phys. Chem. Lett.* 2010, 1, 2445-2450

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for synthesizing upconversion nanoparticle in a single reaction vessel, comprising:
    heating a solvent mixture comprising an organic acid and an organic alkene in the vessel to an elevated temperature from about 300° C. to about 320° C., wherein the organic acid and an organic alkene are selected from the group of solvent pairs consisting of hexadecanoic acid-1-hexadecene, eicosenoic acid-eicosene, and oleic acid-1-octadecene;
    injecting a core precursor solution comprising a mixture of sodium trifluoracetate and rare earth trifluoracetates into the vessel, wherein the rare earth trifluoracetates are a combination of yttrium (Y), ytterbium (Yb) and thulium (Tm) trifluoracetates;
    injecting a shell precursor solution into the vessel, wherein the shell precursor solution comprises $Ca(CF_3COO)_2$ and the solvent mixture; and
    collecting the upconversion nanoparticles,
wherein the above steps are carried out in a single reaction vessel.

2. The method of claim 1, wherein the acid-alkene pair is oleic acid-1-octadecene.

3. The method of claim 2, wherein the step of heating to the elevated temperature comprises a step of first heating to a temperature of about 120° C., followed by a step of heating to a temperature of about 310° C.

4. A method for synthesizing modified upconversion nanoparticle (UCNPs) in a single reaction vessel, comprising:
    combining an upconversion nanoparticle (UCNPs) dispersed in hexane and dimethylformamide (DMF) to form a two-phase mixture, wherein the UCNPs comprise a core of cubic nanocrystals comprising α-Na (Y, Yb, Tm)$F_4$ and an epitaxial shell of $CaF_2$;
    adding a molar excess of Nitrosonium tetrafluoroborate ($NOBF_4$) over the upconversion nanoparticles, wherein the molar excess of $NOBF_4$ over the UCNPs is about 300%;
    the mixture comprising ($NOBF_4$) was stirred at a room temperature for a time required to transfer modified UCNPs from the hexane layer to the DMF layer;
    precipitating the modified UCNPs with an anti-solvent;
    purifying the modified UCNPs by centrifugation; and
    redispersing the modified UCNPs in the polar solvent,
wherein
    the above steps are carried out in a single reaction vessel.

5. The method of claim 4, wherein room temperature is from about 17 to about 23° C.

6. The method of claim 4, wherein the time required to transfer modified UCNPs from the hexane layer to the DMF layer is from about 3 to about 10 minutes.

7. The method of claim 6, wherein the time required about 5 minutes.

8. The method of claim 4, further comprising:
    reacting the modified UCNPs with poly-acrylic acid (PAA); and
    purifying the PAA modified UCNPs by centrifugation.

9. The method of claim 4, further comprising a step of washing the PAA modified UCNPs with water.

* * * * *